United States Patent
Takaishi et al.

(10) Patent No.: US 6,444,617 B1
(45) Date of Patent: Sep. 3, 2002

(54) FUSED-HETEROCYCLE DICARBOXYLIC ACID DIAMIDE DERIVATIVES OR SALTS THEREOF, HERBICIDE AND USAGE THEREOF

(75) Inventors: Hideo Takaishi, Nishinomiya; Takeshi Katsuhira; Hiroshi Yamaguchi, both of Kawachinagano; Youichi Kawabata, Yao; Hiroto Harayama; Yoshiki Oda, both of Kawachinagano; Masahiko Murai, Muko, all of (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 0 days.

(21) Appl. No.: 09/744,579

(22) PCT Filed: Jul. 27, 1999

(86) PCT No.: PCT/JP99/04009
§ 371 (c)(1),
(2), (4) Date: Jan. 26, 2001

(87) PCT Pub. No.: WO00/06549
PCT Pub. Date: Feb. 10, 2000

(30) Foreign Application Priority Data

Jul. 28, 1998 (JP) ............................................. 10-212817

(51) Int. Cl.[7] .................. A01N 43/56; A01N 43/40; C07D 471/04; C07D 491/048; C07D 495/04
(52) U.S. Cl. ................. 504/246; 546/112; 546/113; 546/114; 546/115; 546/116; 546/118; 546/120
(58) Field of Search ................. 504/246; 546/112, 546/113, 114, 115, 116, 118, 120

(56) References Cited

U.S. PATENT DOCUMENTS 5,843,868 A 12/1998 Tonishi et al. ............... 504/260

FOREIGN PATENT DOCUMENTS

JP  A-6-25190   2/1994
JP  9-323974   12/1997

OTHER PUBLICATIONS

MOHAMED: "A Facile Synthesis and Reaction of 6, 7–Dimethylquinoxaline–2, 3–dicarboxyimides.", AFINIDAD,50(444), 123–6 (1985).
Chem. Abstr., vol. 117, (1992), the abstract No. 171375, Ammar,Y.A., "Synthesis and reactions of 6–methylquinoxaline–2, 3–dicarboxyimides," Delta J. Sci., 14 (2), 528–39 (1990).
Chem. Abstr., Vol. 124, (1996) the abstract No. 289449, Zahran, M.A., "Synthesis and reactions of 6,7–dimethyl–N–(carboxyphenyl)quinoxaline–2,3–dicarboxyimide," Al–Azhar J. Pharm. Sci., 13, 60–5 (1994).

Taylor et al., The Reaction of Anthranil with N–phenylmaleimide, J.Org.Chem, 32, 1967, 1899.

Primary Examiner—Bernard Dentz
(74) Attorney, Agent, or Firm—Manelli Denison & Selter PLLC; Paul E. White, Jr.

(57) ABSTRACT

A fused heterocyclic dicarboxylic acid diamide derivative represented by formula (I):

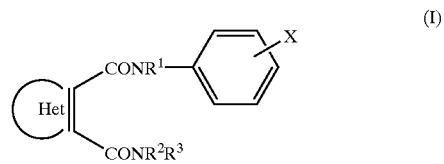

wherein $R^1$ is H, $(C_1-C_6)$ alkyl; $R^2$ and $R^3$ are H, (halo) $(C_1-C_6)$ alkyl, $(C_3-C_8)$ cycloalkyl, substituted amino $(C_1-C_6)$ alkyl, (substituted) phenyl $(C_1-C_6)$ alkyl, (substituted) phenyl $(C_1-C_6)$ alkoxy or the like or $R^2$ and $R^3$, taken conjointly, represent a (substituted) 5- or 6-membered heterocycle having at least one of O, S and N; X is H, halogen, $NO_2$, CN, $(C_1-C_6)$ alkyl, (substituted) phenyl, (substituted) phenoxy or the like;

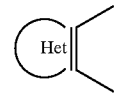

is

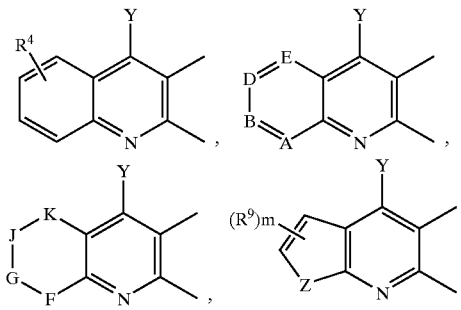

or the like wherein Y, $R^4$ and $R^9$ are H, halogen, $NO_2$, CN, $(C_1-C_6)$ alkyl or the like, and A, B, D, E, F, G, J and K are O, S, N, sulfinyl or the like; and a herbicide containing said derivative as active ingredient.

5 Claims, No Drawings

FUSED-HETEROCYCLE DICARBOXYLIC ACID DIAMIDE DERIVATIVES OR SALTS THEREOF, HERBICIDE AND USAGE THEREOF

This application is the national phase of international application PCT/JP99/03009 filed Jul. 27, 1999 which designated the U.S.

TECHNICAL FIELD

The present invention relates to novel fused heterocyclic dicarboxylic acid diamide derivatives or salts thereof, a herbicide containing said compound or salt thereof as an active ingredient, and a method for using said herbicide.

BACKGROUND ART

In JP-A-6-25190, there is mentioned that pyrazinedicarboxylic acid diamide derivatives are useful as herbicide. In JP-A-9-323974, there is mentioned that pyridinedicarboxylic acid diamide derivatives are useful as herbicide.

DISCLOSURE OF THE INVENTION

The present inventors have conducted extensive studies with the aim of developing a novel herbicide. As a result, it has been found that the fused heterocyclic dicarboxylic acid diamide derivatives represented by general formula (I) of the present invention or salts thereof are novel compounds not found in literature and having an excellent herbicidal activity. Based on this finding, the present invention has been accomplished.

The present invention relates to fused heterocyclic dicarboxylic acid diamide derivatives represented by the following general formula (I):

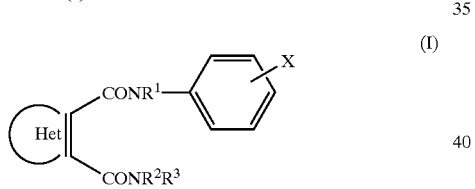

(I)

wherein $R^1$ represents hydrogen atom or $(C_1-C_6)$ alkyl group;

$R^2$ and $R^3$ may be same or different and each represents hydrogen atom, $(C_1-C_8)$ alkyl group, halo $(C_1-C_6)$ alkyl group, $(C_3-C_8)$ cycloalkyl group, $(C_3-C_6)$ cycloalkyl $(C_1-C_6)$ alkyl group, $(C_3-C_6)$ cycloalkyl group having, on the ring thereof, at least one, same or different halogen atoms, $(C_1-C_6)$ alkoxy group, $(C_1-C_6)$ alkoxy $(C_1-C_6)$ alkyl group, $(C_1-C_6)$ alkylthio group, alkylthio $(C_1-C_6)$ alkyl group, cyano $(C_1-C_6)$ alkyl group, $(C_1-C_6)$ alkoxycarbonyl $(C_1-C_6)$ alkyl group, amino $(C_1-C_6)$ alkyl group, substituted amino $(C_1-C_6)$ alkyl group substituted with one or two, same or different $(C_1-C_6)$ alkyl groups, phenyl $(C_1-C_6)$ alkyl group, substituted phenyl $(C_1-C_6)$ alkyl group having, on the ring thereof, at least one, same or different substituents selected from the group consisting of halogen atoms and $(C_1-C_6)$ alkyl groups, phenyl $(C_1-C_6)$ alkoxy group or substituted phenyl $(C_1-C_6)$ alkoxy group having, on the ring thereof, at least one, same or different substituents selected from the group consisting of halogen atoms and $(C_1-C_6)$ alkyl groups; or $R^2$ and $R^3$, taken conjointly, represent a 5- to 6-membered heterocycle having at least one, same or different heteroatoms selected from the group consisting of oxygen atom, sulfur atom and nitrogen atom, further, the carbon atom or nitrogen atom on said heterocycle may have at least one, same or different substituents selected from the group consisting of halogen atom, $(C_1-C_6)$ alkyl group, halo $(C_1-C_6)$ alkyl group, $(C_1-C_6)$ alkoxy group, halo $(C_1-C_6)$ alkoxy group, $(C_1-C_6)$ alkylthio group and halo $(C_1-C_6)$ alkylthio group;

X represents 0 to 5, same or different substituents selected from the group consisting of halogen atom, nitro group, cyano group, $(C_1-C_6)$ alkyl group, halo $(C_1-C_6)$ alkyl group, $(C_3-C_6)$ cycloalkyl group, $(C_3-C_6)$ cycloalkyl $(C_1-C_6)$ alkyl group, $(C_3-C_6)$ cycloalkyl group having, on the ring thereof, at least one, same or different halogen atoms, $(C_1-C_6)$ alkoxy group, halo $(C_1-C_6)$ alkoxy group, $(C_1-C_6)$ alkylthio group, halo $(C_1-C_6)$ alkylthio group, $(C_1-C_6)$ alkyl-sulfinyl group, halo $(C_1-C_6)$ alkylsulfinyl group, $(C_1-C_6)$ alkylsulfonyl group, halo $(C_1-C_6)$ alkylsulfonyl group, $(C_1-C_6)$ alkoxy $(C_1-C_6)$ alkyl group, $(C_1-C_6)$ alkylthio $(C_1-C_6)$ alkyl group, $(C_1-C_6)$ alkoxycarbonyl group, amino group, substituted amino group substituted with same or different $(C_1-C_6)$ alkyl groups, cyano $(C_1-C_6)$ alkyl groups, phenyl $(C_1-C_6)$ alkyl groups, $(C_1-C_6)$ alkoxycarbonyl $(C_1-C_6)$ alkyl groups, $(C_1-C_6)$ alkoxycarbonyl groups, $(C_1-C_6)$ acyl groups, $(C_1-C_6)$ alkylsulfonyl groups or halo $(C_1-C_6)$ alkylsulfonyl groups, phenyl group, substituted phenyl group having at least one, same or different substituents selected from the group consisting of halogen atom, $(C_1-C_6)$ alkyl group, halo $(C_1-C_6)$ alkyl group, $(C_1-C_6)$ alkoxy group, halo $(C_1-C_6)$ alkoxy group, $(C_1-C_6)$ alkylthio group, halo $(C_1-C_6)$ alkylthio group, $(C_1-C_6)$ alkylsulfinyl group, halo $(C_1-C_6)$ alkylsulfinyl group, $(C_1-C_6)$ alkylsulfonyl group, halo $(C_1-C_6)$ alkylsulfonyl group and phenyl group, phenoxy group, substituted phenoxy group having at least one, same or different substituents selected from the group consisting of halogen atom, $(C_1-C_6)$ alkyl group, halo $(C_1-C_6)$ alkyl group, $(C_1-C_6)$ alkoxy group, halo $(C_1-C_6)$ alkoxy group, $(C_1-C_6)$ alkylthio group, halo $(C_1-C_6)$ alkylthio group and phenyl group, phenylthio group, substituted phenylthio group having at least one, same or different substituents selected from the group consisting of halogen atom, $(C_1-C_6)$ alkyl group, halo $(C_1-C_6)$ alkyl group, $(C_1-C_6)$ alkoxy group, halo $(C_1-C_6)$ alkoxy group, $(C_1-C_6)$ alkylthio group, halo $(C_1-C_6)$ alkylthio group and phenyl group, phenyl $(C_1-C_6)$ alkyl group or substituted phenyl $(C_1-C_6)$ alkyl group having, on the ring thereof, at least one, same or different substituents selected from the group consisting of halogen atom, $(C_1-C_6)$ alkyl group, halo $(C_1-C_6)$ alkyl group, $(C_1-C_6)$ alkoxy group, halo $(C_1-C_6)$ alkoxy group, $(C_1-C_6)$ alkylthio group, halo $(C_1-C_6)$ alkylthio group and phenyl group; and

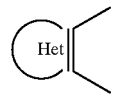

represents $Q^1$, $Q^2$, $Q^3$, $Q^4$, $Q^5$, $Q^6$, $Q^7$, $Q^8$, $Q^9$, $Q^{10}$, $Q^{11}$, $Q^{12}$, $Q^{13}$, or $Q^{14}$, wherein:

$Q^1$ is a group of the following formula:

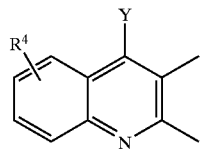

wherein Y represents hydrogen atom, halogen atom, nitro group, cyano group, $(C_1-C_6)$ alkyl group, halo $(C_1-C_6)$ alkyl group, $(C_3-C_6)$ cycloalkyl group, $(C_3-C_6)$ cycloalkyl $(C_1-C_6)$ alkyl group, $(C_1-C_6)$ alkoxy group, halo $(C_1-C_6)$ alkoxy group, $(C_1-C_6)$ alkoxy $(C_1-C_6)$ alkyl group, $(C_1-C_6)$ alkylthio group, halo $(C_1-C_6)$ alkylthio group, $(C_1-C_6)$ alkylsulfinyl group, halo $(C_1-C_6)$ alkylsulfinyl group, $(C_1-C_6)$ alkylsulfonyl group, halo $(C_1-C_6)$ alkylsulfonyl group, $(C_1-C_6)$ alkylthio $(C_1-C_6)$ alkyl group, $(C_1-C_6)$ alkoxycarbonyl group, phenyl group, substituted phenyl group having at least one, same or different substituents selected from the group consisting of halogen atom, $(C_1-C_6)$ alkyl group, halo $(C_1-C_6)$ alkyl group, $(C_1-C_6)$ alkoxy group, halo $(C_1-C_6)$ alkoxy group, $(C_1-C_6)$ alkylthio group, halo $(C_1-C_6)$ alkylthio group, $(C_1-C_6)$ alkylsulfinyl group, halo $(C_1-C_6)$ alkylsulfinyl group, $(C_1-C_6)$ alkylsulfonyl group, halo $(C_1-C_6)$ alkylsulfonyl group and phenyl group, phenoxy group, substituted phenoxy group having at least one, same or different substituents selected from the group consisting of halogen atom, $(C_1-C_6)$ alkyl group, halo $(C_1-C_6)$ alkyl group, $(C_1-C_6)$ alkoxy group, halo $(C_1-C_6)$ alkoxy group, $(C_1-C_6)$ alkylthio group, halo $(C_1-C_6)$ alkylthio group and phenyl group, phenylthio group, substituted phenylthio group having at least one, same or different substituents selected from the group consisting of halogen atom, $(C_1-C_6)$ alkyl group, halo $(C_1-C_6)$ alkyl group, $(C_1-C_6)$ alkoxy group, halo $(C_1-C_6)$ alkoxy group, $(C_1-C_6)$ alkylthio group, halo $(C_1-C_6)$ alkylthio group and phenyl group, amino group, substituted amino group having at least one, same or different substituents selected from the group consisting of $(C_1-C_6)$ alkyl group, cyano $(C_1-C_6)$ alkyl group, $(C_1-C_6)$ alkoxycarbonyl $(C_1-C_6)$ alkyl group, $(C_1-C_6)$ alkoxycarbonyl group, $(C_1-C_6)$ alkoxyamino-carbonyl group, $(C_1-C_6)$ acyl group, $(C_1-C_6)$ alkylsulfonyl group, halo $(C_1-C_6)$ alkylsulfonyl group and phenyl $(C_1-C_6)$ alkyl group, $(C_3-C_6)$ alkyleneimino group, hydrazino group or substituted hydrazino group substituted with same or different $(C_1-C_6)$ alkyl groups; and $R^4$ represents 0 to 4, same or different substituents selected from the group consisting of halogen atom, nitro group, cyano group, hydroxyl group, $(C_1-C_6)$ alkyl group, halo $(C_1-C_6)$ alkyl group, $(C_3-C_6)$ cycloalkyl group, $(C_3-C_6)$ cycloalkyl $(C_1-C_6)$ alkyl group, $(C_1-C_6)$ alkoxy group, halo $(C_1-C_6)$ alkoxy group, $(C_1-C_6)$ alkoxy $(C_1-C_6)$ alkyl group, $(C_1-C_6)$ alkylthio group, halo $(C_1-C_6)$ alkylthio group, $(C_1-C_6)$ alkylsulfinyl group, halo $(C_1-C_6)$ alkylsulfinyl group, $(C_1-C_6)$ alkylsulfonyl group, halo $(C_1-C_6)$ alkylsulfonyl group, $(C_1-C_6)$ alkylthio $(C_1-C_6)$ alkyl group, $(C_1-C_6)$ alkoxycarbonyl group, methylenedioxy group, amino group and substituted amino group substituted with at least one, same or different $(C_1-C_6)$ alkyl groups, cyano $(C_1-C_6)$ alkyl groups, $(C_1-C_6)$ alkoxycarbonyl $(C_1-C_6)$ alkyl groups, $(C_1-C_6)$ alkoxycarbonyl groups, $(C_1-C_6)$ alkoxyaminocarbonyl groups, $(C_1-C_6)$ acyl groups, $(C_1-C_6)$ alkylsulfonyl groups, halo $(C_1-C_6)$ alkylsulfonyl groups or phenyl $(C_1-C_6)$ alkyl groups;

$Q^2$ is a group of the following formula:

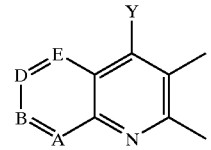

wherein at least one of A, B, D and E represent a nitrogen atom, and the others of A, B, D and E represent C—$R^5$ wherein $R^5$ represents hydrogen atom, halogen atom, nitro group, cyano group, hydroxyl group, $(C_1-C_6)$ alkyl group, halo $(C_1-C_6)$ alkyl group, $(C_3-C_6)$ cycloalkyl group, $(C_3-C_6)$ cycloalkyl $(C_1-C_6)$ alkyl group, $(C_1-C_6)$ alkoxy group, halo $(C_1-C_6)$ alkoxy group, $(C_1-C_6)$ alkoxy $(C_1-C_6)$ alkyl group, $(C_1-C_6)$ alkylthio group, halo $(C_1-C_6)$ alkylthio group, $(C_1-C_6)$ alkylsulfinyl group, halo $(C_1-C_6)$ alkylsulfinyl group, $(C_1-C_6)$ alkylsulfonyl group, halo $(C_1-C_6)$ alkylsulfonyl group, $(C_1-C_6)$ alkylthio $(C_1-C_6)$ alkyl group, $(C_1-C_6)$ alkoxycarbonyl group, amino group or substituted amino group having at least one, same or different substituents selected from the group consisting of $(C_1-C_6)$ alkyl group, cyano $(C_1-C_6)$ alkyl group, $(C_1-C_6)$ alkoxycarbonyl $(C_1-C_6)$ alkyl group, $(C_1-C_6)$ alkoxycarbonyl group, $(C_1-C_6)$ alkoxyaminocarbonyl group, $(C_1-C_6)$ acyl group, $(C_1-C_6)$ alkylsulfonyl group, halo $(C_1-C_6)$ alkylsulfonyl group and phenyl $(C_1-C_6)$ alkyl group; and Y is as defined above;

$Q^3$ is a group of the following formula:

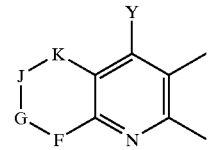

wherein at least one of F, G, J and K represent oxygen atom, sulfur atom, sulfinyl group, sulfonyl group, carbonyl group or N—$R^6$ wherein $R^6$ represents hydrogen atom, hydroxyl group, $(C_1-C_6)$ alkyl group, halo $(C_1-C_6)$ alkyl group, $(C_1-C_6)$ cycloalkyl group, $(C_3-C_6)$ cycloalkyl $(C_1-C_6)$ alkyl group, $(C_1-C_6)$ alkoxy group, $(C_1-C_6)$ alkoxy $(C_1-C_6)$ alkyl group, $(C_1-C_6)$ alkylthio $(C_1-C_6)$ alkyl group, $(C_1-C_6)$ alkoxycarbonyl group, $(C_1-C_6)$ alkyl-sulfonyl group or halo $(C_1-C_6)$ alkylsulfonyl group, and the others of F, G, J and K each represents C—($R_7$) $R^8$ wherein $R^7$ and $R^8$ may be same or different and represent hydrogen atom, $(C_1-C_6)$ alkyl group, halo $(C_1-C_6)$ alkyl group, $(C_3-C_6)$ cycloalkyl group, ($C_3$–$C_6$) cycloalkyl ($C_1$–$C_6$) alkyl group, ($C_3$–$C_6$) cycloalkyl group having at least one, same or different halogen atoms on the ring thereof, ($C_1$–$C_6$) alkoxy group, ($C_1$–$C_6$) alkoxy ($C_1$–$C_6$) alkyl group, ($C_1$–$C_6$) alkylthio ($C_1$–$C_6$) alkyl group, ($C_1$–$C_6$) alkoxycarbonyl ($C_1$–$C_6$) alkyl group, phenyl ($C_1$–$C_6$) alkyl group, substituted phenyl ($C_1$–$C_6$) alkyl group substituted with at least one, same or different halogen atoms or ($C_1$–$C_6$) alkyl groups, amino ($C_1$–$C_6$) alkyl group, substituted amino ($C_1$–$C_6$) alkyl group substituted with at least one, same or different ($C_1$–$C_6$) alkyl groups or phenyl ($C_1$–$C_6$) alkoxy group; and Y is as defined above; and G and J may be taken conjointly to represent CH=CH;

$Q^4$ is a group of the following formula:

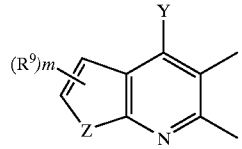

wherein $R^9$ is same or different and represents halogen atom, nitro group, cyano group, ($C_1$–$C_6$) alkyl group, halo ($C_1$–$C_6$) alkyl group, ($C_3$–$C_6$) cycloalkyl group, ($C_3$–$C_6$) cycloalkyl ($C_1$–$C_6$) alkyl group, ($C_1$–$C_6$) alkoxy group, halo ($C_1$–$C_6$) alkoxy group, ($C_1$–$C_6$) alkoxy ($C_1$–$C_6$) alkyl group, ($C_1$–$C_6$) alkoxycarbonyl group, ($C_1$–$C_6$) alkylthio group, halo ($C_1$–$C_6$) alkylthio group, ($C_1$–$C_6$) alkylsulfinyl group, halo ($C_1$–$C_6$) alkylsulfinyl group, ($C_1$–$C_6$) alkylsulfonyl group, halo ($C_1$–$C_6$) alkylsulfonyl group, ($C_1$–$C_6$) alkylthio ($C_1$–$C_6$) alkyl group, phenyl group, substituted phenyl group having at least one, same or different substituents selected from the group consisting of halogen atom, ($C_1$–$C_6$) alkyl group, halo ($C_1$–$C_6$) alkyl group, ($C_1$–$C_6$) alkoxy group, halo ($C_1$–$C_6$) alkoxy group, ($C_1$–$C_6$) alkylthio group, halo ($C_1$–$C_6$) alkylthio group, ($C_1$–$C_6$) alkylsulfinyl group, halo ($C_1$–$C_6$) alkylsulfinyl group, ($C_1$–$C_6$) alkylsulfonyl group, halo ($C_1$–$C_6$) alkylsulfonyl group and phenyl group, phenoxy group, substituted phenoxy group having at least one or different substituents selected from the group consisting of halogen atom, ($C_1$–$C_6$) alkyl group, halo ($C_1$–$C_6$) alkyl group, ($C_1$–$C_6$) alkoxy group, halo ($C_1$–$C_6$) alkoxy group, ($C_1$–$C_6$) alkylthio group, halo ($C_1$–$C_6$) alkylthio group and phenyl group, phenylthio group, substituted phenylthio group having at least one, same or different substituents selected from the group consisting of halogen atom, ($C_1$–$C_6$) alkyl group, halo ($C_1$–$C_6$) alkyl group, ($C_1$–$C_6$) alkoxy group, halo ($C_1$–$C_6$) alkoxy group, ($C_1$–$C_6$) alkylthio group, halo ($C_1$–$C_6$) alkylthio group and phenyl group, amino group, substituted amino group substituted with at least one, same or different substituents selected from the group consisting of ($C_1$–$C_6$) alkyl group, cyano ($C_1$–$C_6$) alkyl group, ($C_1$–$C_6$) alkoxycarbonyl ($C_1$–$C_6$) alkyl group, ($C_1$–$C_6$) alkoxycarbonyl group, ($C_1$–$C_6$) alkoxyaminocarbonyl group, ($C_1$–$C_6$) acyl group, ($C_1$–$C_6$) alkylsulfonyl group, halo ($C_1$–$C_6$) alkylsulfonyl group and phenyl ($C_1$–$C_6$) alkyl group, ($C_3$–$C_6$) alkyleneimino group, hydrazino group or substituted hydrazino group substituted with same or different ($C_1$–$C_6$) alkyl groups; m represents an integer of 0 to 2;

Z represents oxygen atom, sulfur atom or N—$R^{10}$ wherein $R^{10}$ represents hydrogen atom, hydroxyl group, ($C_1$–$C_6$) alkyl group, halo ($C_1$–$C_6$) alkyl group, ($C_3$–$C_6$) cycloalkyl group, ($C_3$–$C_6$) cycloalkyl ($C_1$–$C_6$) alkyl group, ($C_1$–$C_6$) alkoxy group, ($C_1$–$C_6$) alkoxy ($C_1$–$C_6$) alkyl group, ($C_1$–$C_6$) alkoxycarbonyl group, ($C_1$–$C_6$) alkylsulfonyl group, halo ($C_1$–$C_6$) alkylsulfonyl group or ($C_1$–$C_6$) alkylthio ($C_1$–$C_6$) alkyl group; and Y is as defined above;

$Q^5$ is a group of the following formula:

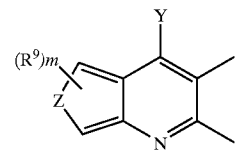

wherein $R^9$, Y, Z and m are as defined above;

$Q^6$ is a group of the following formula:

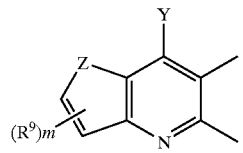

wherein $R^9$, Y, Z and m are as defined above;

$Q^7$ is a group of the following formula:

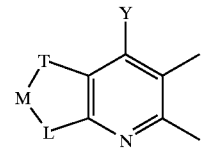

wherein at least one of L, M and T represent oxygen atom, sulfur atom, sulfinyl group, sulfonyl group, carbonyl group or N—$R^{11}$ wherein $R^{11}$ represents hydrogen atom, hydroxyl group, ($C_1$–$C_6$) alkyl group, halo ($C_1$–$C_6$) alkyl group, ($C_3$–$C_6$) cycloalkyl group, ($C_3$–$C_6$) cycloalkyl ($C_1$–$C_6$) alkyl group, ($C_1$–$C_6$) alkoxy group, ($C_1$–$C_6$) alkoxy ($C_1$–$C_6$) alkyl group, ($C_1$–$C_6$) alkoxycarbonyl group, ($C_1$–$C_6$ alkylsulfonyl group, halo ($C_1$–$C_6$) alkylsulfonyl group or ($C_1$–$C_6$) alkylthio ($C_1$–$C_6$) alkyl group, and the others of L, M and T each represents C-($R^{12}$)$R^{13}$ wherein $R^{12}$ and $R^{13}$ may be same or different and each represents hydrogen atom, ($C_1$–$C_6$) alkyl group, halo ($C_1$–$C_6$) alkyl group, ($C_3$–$C_6$) cycloalkyl group, ($C_3$–$C_6$) cycloalkyl ($C_1$–$C_6$) alkyl group, ($C_3$–$C_6$) cycloalkyl group having at least one, same or different halogen atoms on the ring thereof, ($C_1$–$C_6$) alkoxy group, ($C_1$–$C_6$) alkoxy ($C_1$–$C_6$) alkyl group, ($C_1$–$C_6$) alkylthio ($C_1$–$C_6$) alkyl group, ($C_1$–$C_6$) alkoxy-carbonyl ($C_1$–$C_6$) alkyl group, phenyl ($C_1$–$C_6$) alkyl group, substituted phenyl ($C_1$–$C_6$) alkyl group having, on the ring thereof, at least one, same or different substituents selected from the group consisting of halogen atoms and $(C_1-C_6)$ alkyl groups, phenyl $(C_1-C_6)$ alkoxy group, substituted phenyl $(C_1-C_6)$ alkoxy group having, on the ring thereof, at least one, same or different substituents selected from the group consisting of halogen atoms and $(C_1-C_6)$ alkyl groups, amino $(C_1-C_6)$ alkyl group or substituted amino $(C_1-C_6)$ alkyl group substituted with at least one, same or different $(C_1-C_6)$ alkyl groups;

$Q^8$ is a group of the following formula:

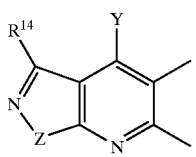

wherein $R^{14}$ represents hydrogen atom or is the same as $R^9$, and Y and Z are as defined above;

$Q^9$ is a group of the following formula:

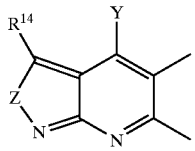

wherein $R^{14}$, Y and Z are as defined above;

$Q^{10}$ is a group of the following formula:

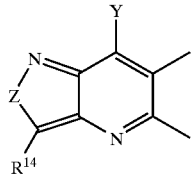

wherein $R^{14}$, Y and Z are as defined above;

$Q^{11}$ is a group of the following formula:

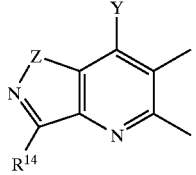

wherein $R^{14}$, Y and Z are as defined above;

$Q^{12}$ is a group of the following formula:

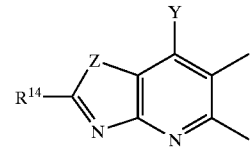

wherein $R^{14}$, Y and Z are as defined above;

$Q^{13}$ is a group of the following formula:

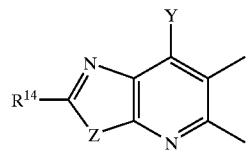

wherein $R^{14}$, Y and Z are as defined above; and $Q^{14}$ is a group of the following formula:

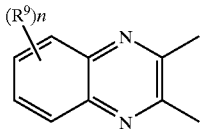

wherein $R^9$ is as defined above and n represents an integer of 0 to 4; and salts of said compounds, a herbicide containing said compound as an active ingredient, and a method for using said herbicide.

In the definitions of the substituents in the fused heterocyclic dicarboxylic acid diamide derivatives represented by general formula (I) or salts thereof, the term "halogen atom" means chlorine atom, bromine atom, iodine atom or fluorine atom; the term $(C_1-C_8)$ means that the number of carbon atoms is 1 to 8; the term $(C_1-C_8)$ alkyl group, for example, means a straight chain or branched chain alkyl group having 1 to 8 carbon atoms; and the term "halo $(C_1-C_6)$ alkyl group" means a straight chain or branched chain alkyl group having 1 to 6 carbon atoms and substituted with at least one, same or different halogen atoms.

As examples of the salt, inorganic acid salts such as hydrochloride, sulfate, nitrate, phosphate and the like; organic acid salts such as acetate, fumarate, maleate, oxalate, methanesulfonate, benzenesulfonate, p-toluenesulfonate and the like; and salts of metal ions such as sodium ion, potassium ion, calcium ion and the like can be referred to.

As a preferable embodiment of the fused heterocyclic dicarboxylic acid diamide derivative represented by general formula (I), a case where $R^1$ and $R^2$ are both hydrogen atom, $R^3$ is $(C_1-C_6)$ alkyl group or $(C_3-C_6)$ cycloalkyl group, X is halogen atom or $(C_1-C_6)$ alkyl group, and

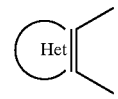

is $Q^2$, $Q^3$, $Q^4$, $Q^6$, $Q^7$, $Q^8$, $Q^{11}$ or the like can be referred to. As a further preferable embodiment, cases where X is substituted at the 2- and 3-positions or at the 2-, 3- and 6-positions can be referred to.

The fused heterocyclic dicarboxylic acid diamide derivatives represented by general formula (I) can be produced, for example, according to the production process schematically shown below.

PRODUCTION PROCESS

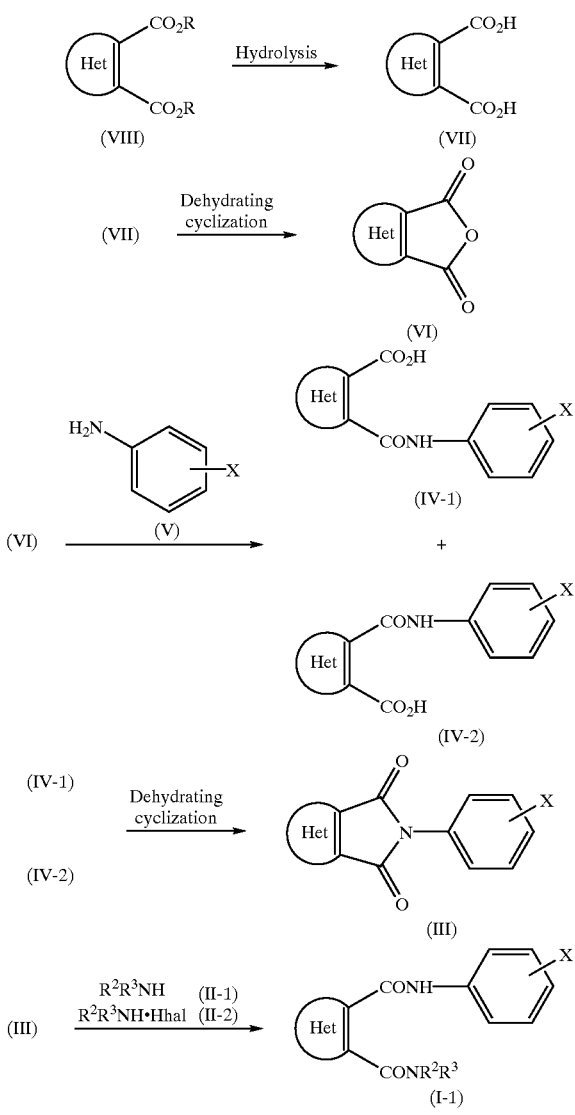

wherein $R^2$, $R^3$, X and

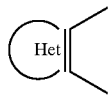

are as defined above, and hal represents a halogen atom.

A fused heterocyclic dicarboxylic acid diamide derivative represented by general formula (I-1) can be produced by hydrolyzing a compound represented by general formula (VIII) in the presence of an acid or an alkali to form a dicarboxylic acid represented by general formula (VII), converting it into an acid anhydride (VI) in the presence of a dehydrating agent, reacting the acid anhydride with a substituted aniline (V) in the presence or absence of an inert solvent to form anilides (IV-1) and (IV-2), and then after isolating or without isolating them, reacting them with a dehydrating agent in the presence or absence of an inert solvent to form imides represented by general formula (III), and after isolating or without isolating the imides (III), reacting them with an amine or a salt thereof represented by general formula (II-1) or (II-2) in the presence or absence of an inert solvent.

A. General Formula (VIII)→General Formula (VII)

As the inert solvents which can be used in this reaction, for example, water, water-soluble solvents such as methanol, ethanol, propanol and the like and mixtures of the water-soluble solvents can be referred to.

As the base which can be used for the hydrolysis, for example, alkali metal hydroxides such as sodium hydroxide, potassium hydroxide and the like can be referred to. The amount of the base may be appropriately selected from a range of 2 to 10 equivalents per equivalent of the diester of general formula (VIII).

The reaction can be carried out at a temperature ranging from ambient temperature to the reflux temperature of the used inert solvent. The reaction time may vary with scale and temperature of the reaction, and it may be appropriately selected from a range of several minutes to 48 hours.

After completion of the reaction, the objective product is isolated from the reaction mixture containing it according to a conventional method, and then the product is purified by recrystallization, distillation, column chromatography or the like according to the need, whereby the objective product can be obtained.

It is also possible to use the product obtained in this step in the subsequent reaction without isolation.

B. General Formula (VII)→General Formula (VI)

The inert solvent used in this reaction may be any inert solvent so far as its use does not obstruct the progress of this reaction greatly. Examples of the inert solvent include halogenated hydrocarbons such as dichloromethane, chloroform, carbon tetrachloride and the like; aromatic hydrocarbons such as benzene, toluene, xylene, chlorobenzene and the like; acyclic and cyclic ethers such as methyl cellosolve, diethyl ether, diisopropyl ether, dioxane, tetrahydrofuran and the like; and organic acids such as acetic acid, trifluoroacetic acid and the like. These inert solvents may be used either alone or in the form of a mixture.

It is also possible to replace the inert solvent with an excessive quantity of the dehydrating agent.

As the dehydrating agent, for example, acetic anhydride, trifluoroacetic anhydride and the like can be used. The amount of these dehydrating agents may be appropriately selected from a range of from equi-molar quantity to excessive molar quantity per mol of the compound of general formula (VII). Preferably the dehydrating agent is used in an equimolar quantity.

The reaction temperature may be appropriately selected in a range of from ambient temperature to the boiling point range of the used inert solvent. When no inert solvent is used, the reaction may be carried out in the boiling point range of the used dehydrating agent.

The reaction time may vary with scale and temperature of the reaction, and it ranges from several minutes to 48 hours.

After completion of the reaction, the objective product is isolated from the reaction mixture containing it according to a conventional method, and then the product is purified by recrystallization, distillation, column chromatography or the like according to the need, whereby the objective product can be obtained.

This reaction can be carried out according to the description of J. Org. Chem. Soc., 52, 129 (1987); J. Am. Chem. Soc., 51, 1865 (1929); ibid., 63, 1542 (1941); etc.

It is also possible to use the objective product in the subsequent reaction without isolation.

C. General Formula (VI)→General Formula (IV-1)+General Formula (IV-2)

As the inert solvent used in this reaction, any inert solvent may be used so far as it does not obstruct progress of the reaction greatly. Examples of the inert solvent include aromatic hydrocarbons such as benzene, toluene, xylene and the like; halogenated hydrocarbons such as methylene chloride, chloroform, carbon tetrachloride, chlorobenzene, dichlorobenzene and the like; acyclic and cyclic ethers such as diethyl ether, dioxane, tetrahydrofuran and the like; esters such as ethyl acetate and the like; amides such as dimethylformamide, dimethylacetamide and the like; acids such as acetic acid and the like; dimethyl sulfoxide; 1,3-dimethyl-2-imidazolidinone; water and the like. These inert solvents may be used either alone or in the form of a mixture of two or more.

Since this reaction is an equimolar reaction, the reactants may be used in equimolar amounts. It is also possible, however, to use any of the reactants in an excessive amount. If desired, this reaction may be carried out under a dehydrating condition.

The reaction temperature may be appropriately selected in a range of from ambient temperature to the boiling point range of the used inert solvent. When no inert solvent is used, the reaction may be carried out in the boiling point range of the used dehydrating agent.

The reaction time may vary with scale and temperature of the reaction, and it ranges from several minutes to 48 hours.

After completion of the reaction, the objective product is isolated from the reaction mixture containing it according to a conventional method, and then the product is purified by recrystallization, distillation, column chromatography or the like according to the need, whereby the objective product can be obtained.

It is also possible to use the objective product in the subsequent reaction without isolation.

D. General Formula (IV-1)+General Formula (IV-2)
—General Formula (III)

This reaction can be carried out in the same manner as B, whereby the objective product can be obtained. It is also possible to use the objective product in the subsequent reaction without isolation.

Hereunder are shown typical examples of the imide represented by general formula (III).

(1). N-(3-Chloro-2,6-diethylphenyl)-1,3-dimethyl-pyrazolo[5,4-b]pyridine-5,6-dicarboximide $^1$H-NMR [TMS/CDCl$_3$, δ (ppm)]; 1.09(3H,t,J=7.5 Hz), 1.13(3H,t,J=7.5 Hz), 2.43(2H,q,J=7.5 Hz), 2.61(2H,q,J=7.5 Hz), 2.69(3H,s), 4.26(3H,s), 7.21(1H,d,J=8.4 Hz), 7.47(1H,d,J=8.4 Hz), 8.61(1H,s).

(2). N-(3-Chloro-2,6-diethylphenyl)thieno[3,2-b]pyridine-5,6-dicarboximide $^1$H-NMR [TMS/CDCl$_3$, δ (ppm)]; 1.09(3H,t,J=7.5 Hz), 1.14(3H,t,J=7.5 Hz), 2.44 (2H,q,J=7.5 Hz), 2.63(2H,q,J=7.5 Hz), 7.20(1H,d,J=8.4 Hz), 7.47(1H,d,J=8.4 Hz), 7.90(1H,d,J=5.7 Hz), 8.17(1H,d,J=5.7 Hz), 8.79(1H,s).

(3). N-(3-Chloro-2,6-diethylphenyl)-2,3-dihydrothieno-[3,2-b]pyridine-5,6-dicarboximide $^1$H-NMR [TMS/CDCl$_3$, δ (ppm)]; 1.06(3H,t,J=7.5 Hz), 1.12(3H,t,J=7.5 Hz), 2.39(2H,q,J=7.5 Hz), 2.58(2H,q,J=7.5 Hz), 3.51–3.68(4H,m), 7.17(1H,d,J=8.4 Hz), 7.44(1H,d,J=8.4 Hz), 7.95(1H,s).

(4). N-(3-Chloro-2,6-diethylphenyl)-2,3-dihydrothieno-[2,3-b]pyridine-5,6-dicarboximide $^1$H-NMR [TMS/CDCl$_3$, δ (ppm)]; 1.05(3H,t,J=7.5 Hz), 1.11(3H,t,J=7.5 Hz), 2.38(2H,q,J=7.5 Hz), 2.57(2H,q,J=7.5 Hz), 3.47–3.61(4H,m), 7.16(1H,d,J=8.4 Hz), 7.43(1H,d,J=8.4 Hz), 7.85(1H,s).

(5). N-(3-chloro-2,6-diethylphenyl)-furo[2,3-b]pyridine-5,6-dicarboximide $^1$H-NMR [TMS/CDCl$_3$, δ (ppm)]; 1.08(3H,t,J=7.5 Hz), 1.13(3H,t,J=7.5 Hz), 2.43(2H,q,J=7.5 Hz), 2.61(2H,q,J=7.5 Hz), 7.11(1H,d,J=2.6 Hz), 7.24(1H,d,J=8.4 Hz), 7.47(1H,d,J=8.4 Hz), 8.05(1H,d,J=2.6 Hz), 8.53(1H,s).

(6). N-(3-Chloro-2,6-diethylphenyl)-1-methyl-pyrrolo-[3,2-b]pyridine-5,6-dicarboximide $^1$H-NMR [TMS/CDCl$_3$, δ (ppm)]; 1.04(3H,t,J=7.5 Hz), 1.08(3H,t,J=7.5 Hz), 2.45(2H,q,J=7.5 Hz), 2.65(2H,q,J=7.5 Hz), 3.93(3H,s), 6.95(1H,d,J=0.6 Hz), 7.15(1H,d,J=8.0 Hz), 7.38(1H,d,J=8.0 Hz), 7.61(1H,d,J=0.6 Hz), 8.17(1H,s).

(7). N-(3-Chloro-2,6-diethylphenyl)-1-methoxy-pyrrolo-[3,2-b]pyridine-5,6-dicarboximide $^1$H-NMR [TMS/CDCl$_3$, δ (ppm)]; 1.06(3H,t,J=7.5 Hz), 1.11(3H,t,J=7.5 Hz), 2.42(2H,q,J=7.5 Hz), 2.65(2H,q,J=7.5 Hz), 4.21(3H,s), 6.90(1H,d,J=0.6 Hz), 7.15(1H,d,J=8.0 Hz), 7.38(1H,d,J=8.0 Hz), 7.81(1H,d,J=0.6 Hz), 8.32(1H,s).

(8). N-(3-Chloro-2,6-diethylphenyl)-1,8-naphthylidine-2,3-dicarboximide $^1$H-NMR [TMS/CDCl$_3$, δ (ppm)]; 1.09(3H,t,J=7.5 Hz), 1.14(3H,t,J=7.5 Hz), 2.43(2H,q,J=7.5 Hz), 2.61(2H,q,J=7.5 Hz), 7.24(1H,d,J=8.4 Hz), 7.52(1H,d,J=8.4 Hz), 8.05(1H,dd,J=2.9 and 7.9 Hz), 8.81(1H,d,J=7.9 Hz), 9.04(1H,s), 9.62(1H,d,J=2.9 Hz).

(9). N-(3-Chloro-2,6-diethylphenyl)-5-oxo-5,6,7,8-tetrahydroquinoline-2,3-dicarboximide $^1$H-NMR [TMS/CDCl$_3$, δ (ppm)]; 1.09(3H,t,J=7.5 Hz), 1.14(3H,t,J=7.5 Hz), 2.30(2H,m), 2.43(2H,q,J=7.5 Hz), 2.48(2H,m), 2.61(2H,q,J=7.5 Hz), 2.85(2H,m), 7.19(1H,d,J=8.4 Hz), 7.42(1H,d,J=8.4 Hz), 8.89(1H,s).

(10). N-(3-Chloro-2,6-diethylphenyl)-6-methyl-5,6,7,8-tetrahydro-1,6-naphthylidine-2,3-dicarboximide $^1$H-NMR [TMS/CDCl$_3$, δ (ppm)]; 1.09(3H,t,J=7.5 Hz), 1.14(3H,t,J=7.5 Hz), 2.33(2H,q,J=7.5 Hz), 2.52(2H,q,J=7.5 Hz), 2.95(3H,s), 3.00–3.12(4H,m), 3.54(2H,m), 7.15(1H,d,J=8.4 Hz), 7.42(1H,d,J=8.4 Hz), 8.02(1H,s).

(11). N-(3-Chloro-2,6-diethylphenyl)-7,8-dihydro-5H-thiopyrano[4,3-b]pyridine-2,3-dicarboximide $^1$H-NMR [TMS/CDCl$_3$, δ (ppm)]; 1.08(3H,t,J=7.5 Hz), 1.13(3H,t,J=7.5 Hz), 2.39(2H,q,J=7.5 Hz), 2.58(2H,q,J=7.5 Hz), 3.11(2H,t,J=5.8 Hz), 3.52(2H,t,J=5.8 Hz), 3.97(2H,s), 7.19(1H,d,J=8.4 Hz), 7.46(1H,d,J=8.4 Hz), 8.08(1H,s).

(12). N-(3-Chloro-2,6-diethylphenyl)-7,8-dihydro-5H-pyrano[4,3-b]pyridine-2,3-dicarboximide $^1$H-NMR [TMS/CDCl$_3$, δ (ppm)]; 1.07(3H,t,J=7.5 Hz), 1.13(3H,t,J=7.5 Hz), 2.39(2H,q,J=7.5 Hz), 2.58(2H,q,J=7.5

Hz), 3.31(2H,t,J=6.2 Hz), 4.15(2H,t,J=6.2 Hz), 4.96(2H,s), 7.18(1H,d,J=8.4 Hz), 7.46(1H,d,J=8.4 Hz), 7.90(1H,s).

(13). N-(3-Chloro-2,6-diethylphenyl)-2,3-quinoxaline-dicarboximide $^1$H-NMR [TMS/CDCl$_3$, δ (ppm)]; 1.11(3H,t,J=7.5 Hz), 1.16(3H,t,J=7.5 Hz), 2.46(2H,q,J=7.5 Hz), 2.64(2H,q,J=7.5 Hz), 7.24(1H,d,J=8.4 Hz), 7.51(1H,d,J=8.4 Hz), 8.07–8.13 (2H,m), 8.48–8.54(2H,m).

(14). N-(3-Chloro-2-methylphenyl)-2,3-quinoxaline-dicarboximide $^1$H-NMR [TMS/CDCl$_3$, δ (ppm)]; 2.29(3H,s), 7.24(1H,d,J=8.0 Hz), 7.34(1H,t,J=8.0 Hz), 7.56(1H,d,J=8.0 Hz), 8.06–8.12(2H,m), 8.46–8.51(2H,m).

(15). N-(3-Chloro-2,6-diethylphenyl)-5-fluoro-2,3-quinolinedicarboximide mp 116–118° C.

(16). N-(3-Chloro-2,6-diethylphenyl)-6-fluoro-2,3-quinolinedicarboximide $^1$H-NMR [TMS/CDCl$_3$, δ (ppm)]; 1.09(3H,t,J=7.8 Hz), 1.14(3H,t,J=7.5 Hz), 2.44(2H,q,J=7.5 Hz), 2.56–2.68(2H, m), 7.22(1H,d,J=8.1 Hz), 7.48(1H,d,J=8.1 Hz), 7.75–7.81 (2H,m), 8.51(1H,m), 8.77(1H,s).

(17). N-(3-Chloro-2,6-diethylphenyl)-7-fluoro-2,3-quinolinedicarboximide $^1$H-NMR [TMS/CDCl$_3$, δ (ppm)]; 1.09(3H,t,J=7.8 Hz), 1.14(3H,t,J=7.5 Hz), 2.44(2H,q,J=7.5 Hz), 2.56–2.68(2H, m), 7.22(1H,d,J=8.1 Hz), 7.48(1H,d,J=8.1 Hz), 7.63(1H, ddd,J=2.4, 8.1 and 9.3 Hz), 8.12(1H,dd,J=2.4 and 9.6 Hz), 8.16(1H,dd,J=5.7 and 9.3 Hz), 8.81(1H,s).

(18.). N-(4-Trifluoromethoxyphenyl)-7-fluoro-2,3-quinolinedicarboximide mp 264–266° C.

(19). N-(4-Trifluoromethoxyphenyl)-6-fluoro-2,3-quinolinedicarboximide mp 287–289° C.

(20). N-(4-Trifluoromethoxyphenyl)-5-fluoro-2,3-quinolinedicarboximide $^1$H-NMR [TMS/CDCl$_3$, δ (ppm)]; 7.39–7.43(2H,m), 7.51 (1H,ddd,J=0.9, 7.8 and 9.0 Hz), 7.63–7.80(2H,m), 7.95(1H, ddd,J=6.0, 7.8 and 8.4 Hz), 8.30(1H,dd,J=0.9 and 8.4 Hz), 9.09(1H,d,J=0.9 Hz).

(21). N-(2-Methyl-4-pentafluoroethylphenyl)-6-fluoro-2,3-quinolinedicarboximide $^1$H-NMR [TMS/CDCl$_3$, δ (ppm)]; 2.33(3H,s), 7.43(1H, d,J=8.4 Hz), 7.62(1H,d,J=8.4 Hz), 7.64(1H,s), 7.81–7.72 (2H,m), 8.50(1H,dd,J=5.4 and 9.0 Hz), 8.77(1H,s).

(22). N-(3-Chloro-2,6-diethylphenyl)-5-chloro-2,3-quinolinedicarboximide $^1$H-NMR [TMS/CDCl$_3$, δ (ppm)]; 1.10(3H,t,J=7.5 Hz), 1.15(3H,t,J=7.5 Hz), 2.45(2H,q,J=7.5 Hz), 2.62(2H,q,J=7.5 Hz), 7.22(1H,d,J=8.5 Hz), 7.50(1H,d,J=8.5 Hz), 7.89–7.96 (2H,m), 8.42(1H,dd,J=2.0 and 8.0 Hz), 9.29(1H,s).

(23). N-(3-Chloro-2,6-diethylphenyl)-6-chloro-2,3-quinolinedicarboximide $^1$H-NMR [TMS/d$_6$-DMSO, δ (ppm)]; 0.99(3H,t,J=7.5 Hz), 1.04(3H,t,J=7.5 Hz), 2.40(2H,q,J=7.5 Hz), 2.60(2H,q, J=7.5 Hz), 7.36(1H,d,J=8.5 Hz), 7.61(1H,d,J=8.5 Hz), 8.09 (1H,d,J=8.1 Hz), 8.40(1H,d,J=8.1 Hz), 8.52(1H,s), 9.15(1H, s).

(24). N-(3-Chloro-methylphenyl)-6-chloro-2,3-quinolinedicarboximide $^1$H-NMR [TMS/CDCl$_3$, δ (ppm)]; 2.27(3H,s), 7.20(1H, d,J=7.8 Hz), 7.32(1H,t,J=7.8 Hz), 7.53(1H,d,J=7.8 Hz), 7.93 (1H,dd,J=2.0 and 8.0 Hz), 8.11(1H,d,J=2.0 Hz), 8.42(1H,d, J=8.0 Hz), 8.71(1H,s).

(25). N-(3-Chloro-2,6-diethylphenyl)-7-chloro-2,3-quinolinedicarboximide $^1$H-NMR [TMS/d$_6$-DMSO, δ (ppm)]; 0.99(3H,t,J=7.5 Hz), 1.04(3H,t,J=7.5 Hz), 2.45(2H,q,J=7.5 Hz), 2.61(2H,q, J=7.5 Hz), 7.37(1H,d,J=8.5 Hz), 7.62(1H,d,J=8.5 Hz), 7.99 (1H,dd,J=2.5 and 8.5 Hz), 8.43(1H,d,J=8.5 Hz), 8.48(1H,d, J=2.5 Hz), 9.24(1H,s).

(26). N-(3-Chloro-2,6-diethylphenyl)-5-methyl-2,3-quinolinedicarboximide mp 178–180° C.

(27). N-(3-Chloro-2,6-diethylphenyl)-6-methyl-2,3-quinolinedicarboximide $^1$H-NMR [TMS/CDCl$_3$, δ (ppm)]; 1.10(3H,t,J=7.5 Hz), 1.14(3H,t,J=7.5 Hz), 2.45(2H,q,J=7.5 Hz), 2.62(2H,q,J=7.5 Hz), 2.65(3H,s), 7.21(1H,d,J=8.5 Hz), 7.47(1H,d,J=8.5 Hz), 7.80(1H,d,J=8.0 Hz), 7.88(1H,s), 8.37(1H,d,J=8.0 Hz), 8.71 (1H,s).

(28). N-(3-Chloro-2,6-diethylphenyl)-8-methyl-2,3-quinolinedicarboximide $^1$H-NMR [TMS/CDCl$_3$, δ (ppm)]; 1.00(3H,t,J=7.5 Hz), 1.14(3H,t,J=7.5 Hz), 2.45(2H,q,J=7.5 Hz), 2.60(2H,q,J=7.5 Hz), 2.95(3H,s), 7.20(1H,d,J=8.5 Hz), 7.40(1H,d,J=8.5 Hz), 7.70(1H,t,J=8.0 Hz), 7.95(1H,d,J=8.0 Hz), 8.75(1H,s).

(29). N-(3-Chloro-2-methylphenyl)-6-methyl-2,3-quinolinedicarboximide $^1$H-NMR [TMS/CDCl$_3$, δ (ppm)]; 2.26(3H,s), 2.65(3H,s), 7.20(1H,d,J=8.5 Hz), 7.30(1H,t,J=8.5 Hz), 7.51(1H,d,J=8.5 Hz), 7.85(1H,d,J=8.0 Hz), 7.87(1H,s), 8.35(1H,d,J=8.0 Hz), 8.69(1H,s).

(30). N-(3-Chloro-2,6-diethylphenyl)-6-hydroxy-2,3-quinolinedicarboximide $^1$H-NMR [TMS/CDCl$_3$, δ (ppm)]; 1.06(3H,t,J=7.5 Hz), 1.14(3H,t,J=7.5 Hz), 2.45(2H,q,J=7.5 Hz), 2.65(2H,q,J=7.5 Hz), 7.20(1H,d,J=8.0 Hz), 7.45(1H,d,J=1.1 Hz), 7.50(1H,d, J=8.0 Hz), 7.60(1H,dd,J=1.1 and 8.5 Hz), 8.38(1H,d,J=8.5 Hz), 8.62(1H,s).

(31). N-(3-Chloro-2,6-diethylphenyl)-6-methoxy-2,3-quinolinedicarboximide $^1$H-NMR [TMS/d6-DMSO, δ (ppm)]; 1.10(3H,t,J=7.5 Hz), 1.18(3H,t,J=7.5 Hz), 2.50(2H,q,J=7.5 Hz), 2.87(2H,q, J=7.5 Hz), 3.95(1H,s), 7.21(1H,d,J=8.5 Hz), 7.35(1H,d,J= 8.5 Hz), 8.05(1H,d,J=8.0 Hz), 8.86(1H,s), 9.24(1H,s), 10.28 (1H,d,J=8.0 Hz).

(32). N-(3-Chloro-2,6-diethylphenyl)-6,7-dimethoxy-2,3-quinolinedicarboximide $^1$H-NMR [TMS/CDCl$_3$, δ (ppm)]; 1.09(3H,t,J=7.8 Hz), 1.14(3H,t,J=7.8 Hz), 2.45(2H,q,J=7.8 Hz), 2.63(2H,q,J=7.8 Hz), 4.10(6H,s), 7.20(1H,d,J=8.5 Hz), 7.28(1H,s), 7.45(1H,d,J=8.5 Hz), 7.76(1H,s), 8.58(1H,s).

(33). N-(3-Chloro-2,6-diethylphenyl)-6,7-methylenedioxy-2,3-quinolinedicarboximide $^1$H-NMR [TMS/CDCl$_3$, δ (ppm)]; 1.09(3H,t,J=7.5 Hz), 1.15(3H,t,J=7.5 Hz), 2.45(2H,q,J=7.5 Hz), 2.62(2H,q,J=7.5 Hz), 6.27(2H,s), 7.20(1H,d,J=8.5 Hz), 7.32(1H,s), 7.45(1H,d,J=8.5 Hz), 7.71(1H,s), 8.55(1H,s).

The fused heterocyclic diesters represented by general formula (VIII) and the dicarboxylic acids represented by general formula (VII) can be produced according to known methods, for example, the methods described in U.S. Pat. No. 3,414,580, U.S. Pat. No. 3,686,171, J. Med. Chem., 27, 1396 (1984), J. Heterocyclic Chem., 12, 1303 (1975), ibid. 15, 1447 (1978), ibid. 1, 1141 (1979), ibid. 17, 443 (1982), ibid. 21, 689 (1984), Beil., 25III, 2028, JP-A-52-77086, J. Am. Chem. Soc., 81, 2456 (1956), J. Org. Chem., 37, 3224 (1972), JP-A-62-175480, JP-A-62-230782, JP-A-60-69083, JP-A-60-185783, JP-A-61-109790, JP-A-62-277385, JP-A-63-295575, JP-A-63-99067, JP-A-64-75474, JP-A-64-90118, Yakugaku Zasshi, 84, 416 (1964), Chem. and Pharm. Bull., 5, 277 (1957), J. Chem. Research (S), 1989, 196, etc.

E. General Formula (III)→General Formula (I-1)

As the inert solvents usable in this reaction, the inert solvents exemplified in B and pyridines can be referred to.

Since this reaction is an equimolar reaction, an amine represented by general formula (II-1) or an amine salt represented by general formula (II-2) is used in an equimolar amount to an imide represented by general formula (III), or in an excessive amount, if desired.

When an amine salt represented by general formula (II-2) is used in this reaction, a base must be used for the purpose of generating a free amine in the reaction system. As the base, an inorganic amine or an organic amine can be used. As the inorganic amine, for example, alkali metal hydroxides and carbonates such as sodium hydroxide, potassium hydroxide, sodium carbonate, potassium carbonate and the like can be used. As the organic base, for example, triethylamine, pyridine, 4-dimethylaminopyridine, 1,8-diazabicyclo-[5,4,0]-7-undecene and the like can be used. The amount of these amines may be appropriately selected from a range of an equimolar amount to an excessive molar amount.

The reaction temperature may be appropriately selected from a range of −10° C. to the boiling point range of the used inert solvent, and preferably from a range of 0° C. to 150° C.

The reaction time may vary with temperature and scale of the reaction, and it ranges from several minutes to 48 hours.

After completion of the reaction, the objective product is isolated from the reaction system containing it and purified by recrystallization, distillation, column chromatography, etc. according to the need, whereby the objective product can be obtained.

Hereunder, typical examples of the fused heterocyclic dicarboxylic acid diamide derivative represented by general formula (I) and salt thereof will be shown in Table 1 to Table 14. The present invention is by no means limited by these compounds. In the tables, the expression "c-" means an alicyclic hydrocarbon, and the expression "Het" means

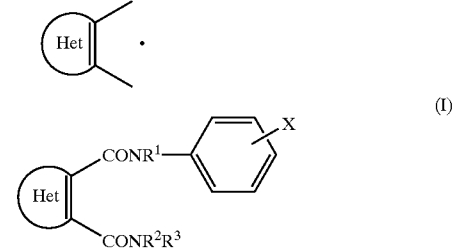

General formula (I)

TABLE 1

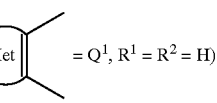
$= Q^1, R^1 = R^2 = H$)

| No | Y | R$^3$ | X | R$^4$ | mp ° C. |
|---|---|---|---|---|---|
| 1 | H | C$_2$H$_5$ | 2,6-(C$_2$H$_5$)$_2$-3-Cl | 5-CH$_3$ | 188–190 |
| 2 | H | n-C$_3$H$_7$ | 2,6-(C$_2$H$_5$)$_2$-3-Cl | 5-CH$_3$ | 208–210 |
| 3 | H | i-C$_3$H$_7$ | 2,6-(C$_2$H$_5$)$_2$-3-Cl | 5-CH$_3$ | 190–192 |
| 4 | H | c-C$_3$H$_5$ | 2,6-(C$_2$H$_5$)$_2$-3-Cl | 5-CH$_3$ | |
| 5 | H | n-C$_4$H$_9$ | 2,6-(C$_2$H$_5$)$_2$-3-Cl | 5-CH$_3$ | |
| 6 | H | s-C$_4$H$_9$ | 2,6-(C$_2$H$_5$)$_2$-3-Cl | 5-CH$_3$ | |
| 7 | H | i-C$_4$H$_9$ | 2,6-(C$_2$H$_5$)$_2$-3-Cl | 5-CH$_3$ | |
| 8 | H | t-C$_4$H$_9$ | 2,6-(C$_2$H$_5$)$_2$-3-Cl | 5-CH$_3$ | |
| 9 | H | n-C$_5$H$_{11}$ | 2,6-(C$_2$H$_5$)$_2$-3-Cl | 5-CH$_3$ | |
| 10 | H | neo-C$_5$H$_{11}$ | 2,6-(C$_2$H$_5$)$_2$-3-Cl | 5-CH$_3$ | |
| 11 | H | c-C$_5$H$_9$ | 2,6-(C$_2$H$_5$)$_2$-3-Cl | 5-CH$_3$ | |
| 12 | H | t-C$_5$H$_{11}$ | 2,6-(C$_2$H$_5$)$_2$-3-Cl | 5-CH$_3$ | |
| 13 | H | n-C$_6$H$_{13}$ | 2,6-(C$_2$H$_5$)$_2$-3-Cl | 5-CH$_3$ | |
| 14 | H | CH$_3$ | 2-CH$_3$-3-Cl | 5-CH$_3$ | |
| 15 | H | C$_2$H$_5$ | 2-CH$_3$-3-Cl | 5-CH$_3$ | |
| 16 | H | n-C$_3$H$_7$ | 2-CH$_3$-3-Cl | 5-CH$_3$ | |
| 17 | H | i-C$_3$H$_7$ | 2-CH$_3$-3-Cl | 5-CH$_3$ | |
| 18 | H | c-C$_3$H$_5$ | 2-CH$_3$-3-Cl | 5-CH$_3$ | |
| 19 | H | n-C$_4$H$_9$ | 2-CH$_3$-3-Cl | 5-CH$_3$ | |

TABLE 1-continued

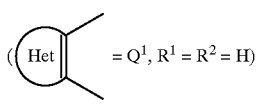 = $Q^1$, $R^1 = R^2 = H$)

| No | Y | $R^3$ | X | $R^4$ | mp °C. |
|---|---|---|---|---|---|
| 20 | H | s-$C_4H_9$ | 2-$CH_3$-3-Cl | 5-$CH_3$ | |
| 21 | H | i-$C_4H_9$ | 2-$CH_3$-3-Cl | 5-$CH_3$ | |
| 22 | H | t-$C_4H_9$ | 2-$CH_3$-3-Cl | 5-$CH_3$ | |
| 23 | H | n-$C_5H_{11}$ | 2-$CH_3$-3-Cl | 5-$CH_3$ | |
| 24 | H | neo-$C_5H_{11}$ | 2-$CH_3$-3-Cl | 5-$CH_3$ | |
| 25 | H | c-$C_5H_9$ | 2-$CH_3$-3-Cl | 5-$CH_3$ | |
| 26 | H | t-$C_5H_{11}$ | 2-$CH_3$-3-Cl | 5-$CH_3$ | |
| 27 | H | n-$C_6H_{13}$ | 2-$CH_3$-3-Cl | 5-$CH_3$ | |
| 28 | H | $CH_3$ | 2,6-$(C_2H_5)_2$-3-Cl | 6-$CH_3$ | 234–236 |
| 29 | H | $C_2H_5$ | 2,6-$(C_2H_5)_2$-3-Cl | 6-$CH_3$ | 226–228 |
| 30 | H | n-$C_3H_7$ | 2,6-$(C_2H_5)_2$-3-Cl | 6-$CH_3$ | 221–222 |
| 31 | H | i-$C_3H_7$ | 2,6-$(C_2H_5)_2$-3-Cl | 6-$CH_3$ | |
| 32 | H | c-$C_3H_5$ | 2,6-$(C_2H_5)_2$-3-Cl | 6-$CH_3$ | |
| 33 | H | n-$C_4H_9$ | 2,6-$(C_2H_5)_2$-3-Cl | 6-$CH_3$ | |
| 34 | H | s-$C_4H_9$ | 2,6-$(C_2H_5)_2$-3-Cl | 6-$CH_3$ | |
| 35 | H | i-$C_4H_9$ | 2,6-$(C_2H_5)_2$-3-Cl | 6-$CH_3$ | |
| 36 | H | t-$C_4H_9$ | 2,6-$(C_2H_5)_2$-3-Cl | 6-$CH_3$ | |
| 37 | H | n-$C_5H_{11}$ | 2,6-$(C_2H_5)_2$-3-Cl | 6-$CH_3$ | |
| 38 | H | neo-$C_5H_{11}$ | 2,6-$(C_2H_5)_2$-3-Cl | 6-$CH_3$ | |
| 39 | H | c-$C_5H_9$ | 2,6-$(C_2H_5)_2$-3-Cl | 6-$CH_3$ | |
| 40 | H | t-$C_5H_{11}$ | 2,6-$(C_2H_5)_2$-3-Cl | 6-$CH_3$ | |
| 41 | H | n-$C_6H_{13}$ | 2,6-$(C_2H_5)_2$-3-Cl | 6-$CH_3$ | |
| 42 | H | $CH_3$ | 2-$CH_3$-3-Cl | 6-$CH_3$ | |
| 43 | H | $C_2H_5$ | 2-$CH_3$-3-Cl | 6-$CH_3$ | 225–228 |
| 44 | H | n-$C_3H_7$ | 2-$CH_3$-3-Cl | 6-$CH_3$ | 217–220 |
| 45 | H | i-$C_3H_7$ | 2-$CH_3$-3-Cl | 6-$CH_3$ | |
| 46 | H | c-$C_3H_5$ | 2-$CH_3$-3-Cl | 6-$CH_3$ | |
| 47 | H | n-$C_4H_9$ | 2-$CH_3$-3-Cl | 6-$CH_3$ | |
| 48 | H | s-$C_4H_9$ | 2-$CH_3$-3-Cl | 6-$CH_3$ | |
| 49 | H | i-$C_4H_9$ | 2-$CH_3$-3-Cl | 6-$CH_3$ | |
| 50 | H | t-$C_4H_9$ | 2-$CH_3$-3-Cl | 6-$CH_3$ | |
| 51 | H | n-$C_5H_{11}$ | 2-$CH_3$-3-Cl | 6-$CH_3$ | |
| 52 | H | neo-$C_5H_{11}$ | 2-$CH_3$-3-Cl | 6-$CH_3$ | |
| 53 | H | c-$C_5H_9$ | 2-$CH_3$-3-Cl | 6-$CH_3$ | 218–219 |
| 54 | H | $C_2H_5$ | 4-$OCF_3$ | 6-$CH_3$ | 215-217 |
| 55 | H | n-$C_3H_7$ | 4-$OCF_3$ | 6-$CH_3$ | 202-204 |
| 56 | H | i-$C_3H_7$ | 4-$OCF_3$ | 6-$CH_3$ | 213-215 |
| 57 | H | $C_2H_5$ | 2,6-$(C_2H_5)_2$-3-Cl | 7-$CH_3$ | |
| 58 | H | n-$C_3H_7$ | 2,6-$(C_2H_5)_2$-3-Cl | 7-$CH_3$ | 199–201 |
| 59 | H | i-$C_3H_7$ | 2,6-$(C_2H_5)_2$-3-Cl | 7-$CH_3$ | |
| 60 | H | c-$C_3H_5$ | 2,6-$(C_2H_5)_2$-3-Cl | 7-$CH_3$ | |
| 61 | H | n-$C_4H_9$ | 2,6-$(C_2H_5)_2$-3-Cl | 7-$CH_3$ | |
| 62 | H | s-$C_4H_9$ | 2,6-$(C_2H_5)_2$-3-Cl | 7-$CH_3$ | |
| 63 | H | i-$C_4H_9$ | 2,6-$(C_2H_5)_2$-3-Cl | 7-$CH_3$ | |
| 64 | H | t-$C_4H_9$ | 2,6-$(C_2H_5)_2$-3-Cl | 7-$CH_3$ | |
| 65 | H | n-$C_5H_{11}$ | 2,6-$(C_2H_5)_2$-3-Cl | 7-$CH_3$ | |
| 66 | H | neo-$C_5H_{11}$ | 2,6-$(C_2H_5)_2$-3-Cl | 7-$CH_3$ | |
| 67 | H | c-$C_5H_9$ | 2,6-$(C_2H_5)_2$-3-Cl | 7-$CH_3$ | |
| 68 | H | t-$C_5H_{11}$ | 2,6-$(C_2H_5)_2$-3-Cl | 7-$CH_3$ | |
| 69 | H | n-$C_6H_{13}$ | 2,6-$(C_2H_5)_2$-3-Cl | 7-$CH_3$ | |
| 70 | H | $C_2H_5$ | 2,6-$(C_2H_5)_2$-3-Cl | 8-$CH_3$ | |
| 71 | H | n-$C_3H_7$ | 2,6-$(C_2H_5)_2$-3-Cl | 8-$CH_3$ | 227–228 |
| 72 | H | i-$C_3H_7$ | 2,6-$(C_2H_5)_2$-3-Cl | 8-$CH_3$ | |
| 73 | H | c-$C_3H_5$ | 2,6-$(C_2H_5)_2$-3-Cl | 8-$CH_3$ | |
| 74 | H | n-$C_4H_9$ | 2,6-$(C_2H_5)_2$-3-Cl | 8-$CH_3$ | |
| 75 | H | s-$C_4H_9$ | 2,6-$(C_2H_5)_2$-3-Cl | 8-$CH_3$ | |
| 76 | H | i-$C_4H_9$ | 2,6-$(C_2H_5)_2$-3-Cl | 8-$CH_3$ | |
| 77 | H | t-$C_4H_9$ | 2,6-$(C_2H_5)_2$-3-Cl | 8-$CH_3$ | |
| 78 | H | n-$C_5H_{11}$ | 2,6-$(C_2H_5)_2$-3-Cl | 8-$CH_3$ | |
| 79 | H | neo-$C_5H_{11}$ | 2,6-$(C_2H_5)_2$-3-Cl | 8-$CH_3$ | |
| 80 | H | c-$C_5H_9$ | 2,6-$(C_2H_5)_2$-3-Cl | 8-$CH_3$ | |
| 81 | H | t-$C_5H_{11}$ | 2,6-$(C_2H_5)_2$-3-Cl | 8-$CH_3$ | |
| 82 | H | n-$C_6H_{13}$ | 2,6-$(C_2H_5)_2$-3-Cl | 8-$CH_3$ | |
| 83 | H | $CH_3$ | 2-$CH_3$-3-Cl | 8-$CH_3$ | |
| 84 | H | $C_2H_5$ | 2-$CH_3$-3-Cl | 8-$CH_3$ | |
| 85 | H | n-$C_3H_7$ | 2-$CH_3$-3-Cl | 8-$CH_3$ | |
| 86 | H | i-$C_3H_7$ | 2-$CH_3$-3-Cl | 8-$CH_3$ | |
| 87 | H | c-$C_3H_5$ | 2-$CH_3$-3-Cl | 8-$CH_3$ | |
| 88 | H | n-$C_4H_9$ | 2-$CH_3$-3-Cl | 8-$CH_3$ | |
| 89 | H | s-$C_4H_9$ | 2-$CH_3$-3-Cl | 8-$CH_3$ | |
| 90 | H | i-$C_4H_9$ | 2-$CH_3$-3-Cl | 8-$CH_3$ | |

TABLE 1-continued (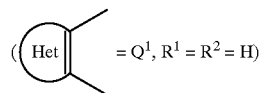 = Q$^1$, R$^1$ = R$^2$ = H)

| No  | Y | R$^3$       | X                       | R$^4$   | mp ° C. |
|-----|---|-------------|-------------------------|---------|---------|
| 91  | H | t-C$_4$H$_9$      | 2-CH$_3$-3-Cl           | 8-CH$_3$ |         |
| 92  | H | n-C$_5$H$_{11}$   | 2-CH$_3$-3-Cl           | 8-CH$_3$ |         |
| 93  | H | neo-C$_5$H$_{11}$ | 2-CH$_3$-3-Cl           | 8-CH$_3$ |         |
| 94  | H | c-C$_5$H$_9$      | 2-CH$_3$-3-Cl           | 8-CH$_3$ |         |
| 95  | H | t-C$_5$H$_{11}$   | 2-CH$_3$-3-Cl           | 8-CH$_3$ |         |
| 96  | H | n-C$_6$H$_{13}$   | 2-CH$_3$-3-Cl           | 8-CH$_3$ |         |
| 97  | H | H           | 2,6-(C$_2$H$_5$)$_2$-3-Cl | 5-F     | 266–268 |
| 98  | H | CH$_3$      | 2,6-(C$_2$H$_5$)$_2$-3-Cl | 5-F     |         |
| 99  | H | C$_2$H$_5$  | 2,6-(C$_2$H$_5$)$_2$-3-Cl | 5-F     | 227–229 |
| 100 | H | n-C$_3$H$_7$ | 2,6-(C$_2$H$_5$)$_2$-3-Cl | 5-F     | 207–209 |
| 101 | H | i-C$_3$H$_7$ | 2,6-(C$_2$H$_5$)$_2$-3-Cl | 5-F     | 213–215 |
| 102 | H | c-C$_3$H$_5$ | 2,6-(C$_2$H$_5$)$_2$-3-Cl | 5-F     |         |
| 103 | H | n-C$_4$H$_9$ | 2,6-(C$_2$H$_5$)$_2$-3-Cl | 5-F     |         |
| 104 | H | s-C$_4$H$_9$ | 2,6-(C$_2$H$_5$)$_2$-3-Cl | 5-F     |         |
| 105 | H | i-C$_4$H$_9$ | 2,6-(C$_2$H$_5$)$_2$-3-Cl | 5-F     |         |
| 106 | H | t-C$_4$H$_9$ | 2,6-(C$_2$H$_5$)$_2$-3-Cl | 5-F     |         |
| 107 | H | n-C$_5$H$_{11}$ | 2,6-(C$_2$H$_5$)$_2$-3-Cl | 5-F     |         |
| 108 | H | neo-C$_5$H$_{11}$ | 2,6-(C$_2$H$_5$)$_2$-3-Cl | 5-F     |         |
| 109 | H | c-C$_5$H$_9$ | 2,6-(C$_2$H$_5$)$_2$-3-Cl | 5-F     |         |
| 110 | H | t-C$_5$H$_{11}$ | 2,6-(C$_2$H$_5$)$_2$-3-Cl | 5-F     |         |
| 111 | H | n-C$_6$H$_{13}$ | 2,6-(C$_2$H$_5$)$_2$-3-Cl | 5-F     |         |
| 112 | H | CH$_3$      | 2-CH$_3$-3-Cl           | 5-F     |         |
| 113 | H | C$_2$H$_5$  | 2-CH$_3$-3-Cl           | 5-F     |         |
| 114 | H | n-C$_3$H$_7$ | 2-CH$_3$-3-Cl           | 5-F     |         |
| 115 | H | i-C$_3$H$_7$ | 2-CH$_3$-3-Cl           | 5-F     |         |
| 116 | H | c-C$_3$H$_5$ | 2-CH$_3$-3-Cl           | 5-F     |         |
| 117 | H | n-C$_4$H$_9$ | 2-CH$_3$-3-Cl           | 5-F     |         |
| 118 | H | s-C$_4$H$_9$ | 2-CH$_3$-3-Cl           | 5-F     |         |
| 119 | H | i-C$_4$H$_9$ | 2-CH$_3$-3-Cl           | 5-F     |         |
| 120 | H | t-C$_4$H$_9$ | 2-CH-3-Cl               | 5-F     |         |
| 121 | H | n-C$_5$H$_{11}$ | 2-CH$_3$-3-Cl           | 5-F     |         |
| 122 | H | neo-C$_5$H$_{11}$ | 2-CH$_3$-3-Cl           | 5-F     |         |
| 123 | H | c-C$_5$H$_9$ | 2-CH$_3$-3-Cl           | 5-F     |         |
| 124 | H | n-C$_3$H$_7$ | 4-OCF$_3$               | 5-F     | 191–193 |
| 125 | H | i-C$_3$H$_7$ | 4-OCF$_3$               | 5-F     | 210–212 |
| 126 | H | H           | 2,6-(C$_2$H$_5$)$_2$-3-Cl | 6-F     | 286–288 |
| 127 | H | CH$_3$      | 2,6-(C$_2$H$_5$)$_2$-3-Cl | 6-F     | 247–249 |
| 128 | H | C$_2$H$_5$  | 2,6-(C$_2$H$_5$)$_2$-3-Cl | 6-F     | 212–213 |
| 129 | H | n-C$_3$H$_7$ | 2,6-(C$_2$H$_5$)$_{7-3-Cl}$ | 6-F | 210–212 |
| 130 | H | i-C$_3$H$_7$ | 2,6-(C$_2$H$_5$)$_2$-3-Cl | 6-F     | 202–204 |
| 131 | H | c-C$_3$H$_5$ | 2,6-(C$_2$H$_5$)$_2$-3-Cl | 6-F     |         |
| 132 | H | n-C$_4$H$_9$ | 2,6-(C$_2$H$_5$)$_2$-3-Cl | 6-F     |         |
| 133 | H | s-C$_4$H$_9$ | 2,6-(C$_2$H$_5$)$_2$-3-Cl | 6-F     |         |
| 134 | H | i-C$_4$H$_9$ | 2,6-(C$_2$H$_5$)$_2$-3-Cl | 6-F     |         |
| 135 | H | t-C$_4$H$_9$ | 2,6-(C$_2$H$_5$)$_2$-3-Cl | 6-F     |         |
| 136 | H | n-C$_5$H$_{11}$ | 2,6-(C$_2$H$_5$)$_2$-3-Cl | 6-F     |         |
| 137 | H | neo-C$_5$H$_{11}$ | 2,6-(C$_2$H$_5$)$_2$-3-Cl | 6-F     |         |
| 138 | H | c-C$_5$H$_9$ | 2,6-(C$_2$H$_5$)$_2$-3-Cl | 6-F     |         |
| 139 | H | t-C$_5$H$_{11}$ | 2,6-(C$_2$H$_5$)$_2$-3-Cl | 6-F     |         |
| 140 | H | n-C$_6$H$_{13}$ | 2,6-(C$_2$H$_5$)$_2$-3-Cl | 6-F     |         |
| 141 | H | CH$_3$      | 2-CH$_3$-3-Cl           | 6-F     |         |
| 142 | H | C$_2$H$_5$  | 2-CH$_3$-3-Cl           | 6-F     |         |
| 143 | H | n-C$_3$H$_7$ | 2-CH$_3$-3-Cl           | 6-F     |         |
| 144 | H | i-C$_3$H$_7$ | 2-CH$_3$-3-Cl           | 6-F     |         |
| 145 | H | c-C$_3$H$_5$ | 2-CH$_3$-3-Cl           | 6-F     |         |
| 146 | H | n-C$_4$H$_9$ | 2-CH$_3$-3-Cl           | 6-F     |         |
| 147 | H | s-C$_4$H$_9$ | 2-CH$_3$-3-Cl           | 6-F     |         |
| 148 | H | i-C$_4$H$_9$ | 2-CH$_3$-3-Cl           | 6-F     |         |
| 149 | H | t-C$_4$H$_9$ | 2-CH$_3$-3-Cl           | 6-F     |         |
| 150 | H | n-C$_5$H$_{11}$ | 2-CH$_3$-3-Cl           | 6-F     |         |
| 151 | H | neo-C$_5$H$_{11}$ | 2-CH$_3$-3-Cl           | 6-F     |         |
| 152 | H | c-C$_5$H$_9$ | 2-CH$_3$-3-Cl           | 6-F     |         |
| 153 | H | t-C$_5$H$_{11}$ | 2-CH$_3$-3-Cl           | 6-F     |         |
| 154 | H | n-C$_6$H$_{13}$ | 2-CH$_3$-3-Cl           | 6-F     |         |
| 155 | H | C$_2$H$_5$  | 4-OCF$_3$               | 6-F     | 242–244 |
| 156 | H | i-C$_3$H$_7$ | 4-OCF$_3$               | 6-F     | 248–250 |
| 157 | H | C$_2$H$_5$  | 2,6-(C$_2$H$_5$)$_2$-3-Cl | 7-F     | 231–233 |
| 158 | H | n-C$_3$H$_7$ | 2,6-(C$_2$H$_5$)$_2$-3-Cl | 7-F     | 220–222 |
| 159 | H | i-C$_3$H$_7$ | 2,6-(C$_2$H$_5$)$_2$-3-Cl | 7-F     |         |
| 160 | H | c-C$_3$H$_5$ | 2,6-(C$_2$H$_5$)$_2$-3-Cl | 7-F     |         |
| 161 | H | n-C$_4$H$_9$ | 2,6-(C$_2$H$_5$)$_2$-3-Cl | 7-F     |         |

TABLE 1-continued

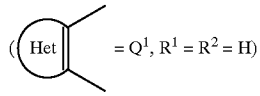 = $Q^1$, $R^1 = R^2 = H$)

| No | Y | $R^3$ | X | $R^4$ | mp °C. |
|---|---|---|---|---|---|
| 162 | H | s-$C_4H_9$ | 2,6-$(C_2H_5)_2$-3-Cl | 7-F | |
| 163 | H | i-$C_4H_9$ | 2,6-$(C_2H_5)_2$-3-Cl | 7-F | |
| 164 | H | t-$C_4H_9$ | 2,6-$(C_2H_5)_2$-3-Cl | 7-F | |
| 165 | H | n-$C_5H_{11}$ | 2,6-$(C_2H_5)_2$-3-Cl | 7-F | |
| 166 | H | neo-$C_5H_{11}$ | 2,6-$(C_2H_5)_2$-3-Cl | 7-F | |
| 167 | H | c-$C_5H_9$ | 2,6-$(C_2H_5)_2$-3-Cl | 7-F | |
| 168 | H | t-$C_5H_{11}$ | 2,6-$(C_2H_5)_2$-3-Cl | 7-F | |
| 169 | H | n-$C_6H_{13}$ | 2,6-$(C_2H_5)_2$-3-Cl | 7-F | |
| 170 | H | $CH_3$ | 2-$CH_3$-3-Cl | 7-F | |
| 171 | H | $C_2H_5$ | 2-$CH_3$-3-Cl | 7-F | |
| 172 | H | n-$C_3H_7$ | 2-$CH_3$-3-Cl | 7-F | |
| 173 | H | i-$C_3H_7$ | 2-$CH_3$-3-Cl | 7-F | |
| 174 | H | c-$C_3H_5$ | 2-$CH_3$-3-Cl | 7-F | |
| 175 | H | n-$C_4H_9$ | 2-$CH_3$-3-Cl | 7-F | |
| 176 | H | s-$C_4H_9$ | 2-$CH_3$-3-Cl | 7-F | |
| 177 | H | i-$C_4H_9$ | 2-$CH_3$-3-Cl | 7-F | |
| 178 | H | t-$C_4H_9$ | 2-$CH_3$-3-Cl | 7-F | |
| 179 | H | n-$C_5H_{11}$ | 2-$CH_3$-3-Cl | 7-F | |
| 180 | H | neo-$C_5H_{11}$ | 2-$CH_3$-3-Cl | 7-F | |
| 181 | H | c-$C_5H_9$ | 2-$CH_3$-3-Cl | 7-F | |
| 182 | H | t-$C_5H_{11}$ | 2-$CH_3$-3-Cl | 7-F | |
| 183 | H | n-$C_6H_{13}$ | 2-$CH_3$-3-Cl | 7-F | |
| 184 | H | $C_2H_5$ | 4-$OCF_3$ | 7-F | 269–271 |
| 185 | H | i-$C_3H_7$ | 4-$OCF_3$ | 7-F | 264–266 |
| 186 | H | H | 2,6-$(C_2H_5)_2$-3-Cl | 5-Cl | |
| 187 | H | $CH_3$ | 2,6-$(C_2H_5)_2$-3-Cl | 5-Cl | |
| 188 | H | $C_2H_5$ | 2,6-$(C_2H_5)_2$-3-Cl | 5-Cl | |
| 189 | H | n-$C_3H_7$ | 2,6-$(C_2H_5)_2$-3-Cl | 5-Cl | 235–237 |
| 190 | H | i-$C_3H_7$ | 2,6-$(C_2H_5)_2$-3-Cl | 5-Cl | |
| 191 | H | c-$C_3H_5$ | 2,6-$(C_2H_5)_2$-3-Cl | 5-Cl | |
| 192 | H | n-$C_4H_9$ | 2,6-$(C_2H_5)_2$-3-Cl | 5-Cl | |
| 193 | H | s-$C_4H_9$ | 2,6-$(C_2H_5)_2$-3-Cl | 5-Cl | |
| 194 | H | i-$C_4H_9$ | 2,6-$(C_2H_5)_2$-3-Cl | 5-Cl | |
| 195 | H | t-$C_4H_9$ | 2,6-$(C_2H_5)_2$-3-Cl | 5-Cl | |
| 196 | H | n-$C_5H_{11}$ | 2,6-$(C_2H_5)_2$-3-Cl | 5-Cl | |
| 197 | H | neo-$C_5H_{11}$ | 2,6-$(C_2H_5)_2$-3-Cl | 5-Cl | |
| 198 | H | c-$C_5H_9$ | 2,6-$(C_2H_5)_2$-3-Cl | 5-Cl | |
| 199 | H | t-$C_5H_{11}$ | 2,6-$(C_2H_5)_2$-3-Cl | 5-Cl | |
| 200 | H | $CH_2CH_2CN$ | 2,6-$(C_2H_5)_2$-3-Cl | 5-Cl | 217–219 |
| 201 | H | $CH_2CH_2OCH_3$ | 2,6-$(C_2H_5)_2$-3-Cl | 5-Cl | 199–201 |
| 202 | H | $CH_3$ | 2-$CH_3$-3-Cl | 5-Cl | |
| 203 | H | $C_2H_5$ | 2-$CH_3$-3-Cl | 5-Cl | |
| 204 | H | n-$C_3H_7$ | 2-$CH_3$-3-Cl | 5-Cl | |
| 205 | H | i-$C_3H_7$ | 2-$CH_3$-3-Cl | 5-Cl | |
| 206 | H | c-$C_3H_5$ | 2-$CH_3$-3-Cl | 5-Cl | |
| 207 | H | n-$C_4H_9$ | 2-$CH_3$-3-Cl | 5-Cl | |
| 208 | H | s-$C_4H_9$ | 2-$CH_3$-3-Cl | 5-Cl | |
| 209 | H | i-$C_4H_9$ | 2-$CH_3$-3-Cl | 5-Cl | |
| 210 | H | t-$C_4H_9$ | 2-$CH_3$-3-Cl | 5-Cl | |
| 211 | H | n-$C_5H_{11}$ | 2-$CH_3$-3-Cl | 5-Cl | |
| 212 | H | neo-$C_5H_{11}$ | 2-$CH_3$-3-Cl | 5-Cl | |
| 213 | H | c-$C_5H_9$ | 2-$CH_3$-3-Cl | 5-Cl | |
| 214 | H | n-$C_3H_7$ | 4-$OCF_3$ | 5-Cl | 210–212 |
| 215 | H | i-$C_3H_7$ | 4-$OCF_3$ | 5-Cl | 228–229 |
| 216 | H | H | 2,6-$(C_2H_5)_2$-3-Cl | 6-Cl | |
| 217 | H | $CH_3$ | 2,6-$(C_2H_5)_2$-3-Cl | 6-Cl | |
| 218 | H | $C_2H_5$ | 2,6-$(C_2H_5)_2$-3-Cl | 6-Cl | |
| 219 | H | n-$C_3H_7$ | 2,6-$(C_2H_5)_2$-3-Cl | 6-Cl | 211–213 |
| 220 | H | i-$C_3H_7$ | 2,6-$(C_2H_5)_2$-3-Cl | 6-Cl | |
| 221 | H | c-$C_3H_5$ | 2,6-$(C_2H_5)_2$-3-Cl | 6-Cl | |
| 222 | H | n-$C_4H_9$ | 2,6-$(C_2H_5)_2$-3-Cl | 6-Cl | |
| 223 | H | s-$C_4H_9$ | 2,6-$(C_2H_5)_2$-3-Cl | 6-Cl | |
| 224 | H | i-$C_4H_9$ | 2,6-$(C_2H_5)_2$-3-Cl | 6-Cl | 214–215 |
| 225 | H | t-$C_4H_9$ | 2,6-$(C_2H_5)_2$-3-Cl | 6-Cl | |
| 226 | H | n-$C_5H_{11}$ | 2,6-$(C_2H_5)_2$-3-Cl | 6-Cl | |
| 227 | H | neo-$C_5H_{11}$ | 2,6-$(C_2H_5)_2$-3-Cl | 6-Cl | |
| 228 | H | c-$C_5H_9$ | 2,6-$(C_2H_5)_2$-3-Cl | 6-Cl | 203–204 |
| 229 | H | t-$C_5H_{11}$ | 2,6-$(C_2H_5)_2$-3-Cl | 6-Cl | |
| 230 | H | n-$C_6H_{13}$ | 2,6-$(C_2H_5)_2$-3-Cl | 6-Cl | |
| 231 | H | $CH_3$ | 2-$CH_3$-3-Cl | 6-Cl | |
| 232 | H | $C_2H_5$ | 2-$CH_3$-3-Cl | 6-Cl | |

TABLE 1-continued

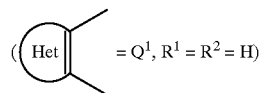 = $Q^1$, $R^1 = R^2 = H$)

| No | Y | $R^3$ | X | $R^4$ | mp ° C. |
|---|---|---|---|---|---|
| 234 | H | n-$C_3H_7$ | 2-$CH_3$-3-Cl | 6-Cl | 217–219 |
| 235 | H | i-$C_3H_7$ | 2-$CH_3$-3-Cl | 6-Cl | |
| 236 | H | c-$C_3H_5$ | 2-$CH_3$-3-Cl | 6-Cl | |
| 237 | H | n-$C_4H_9$ | 2-$CH_3$-3-Cl | 6-Cl | |
| 238 | H | s-$C_4H_9$ | 2-$CH_3$-3-Cl | 6-Cl | |
| 239 | H | i-$C_4H_9$ | 2-$CH_3$-3-Cl | 6-Cl | |
| 240 | H | t-$C_4H_9$ | 2-$CH_3$-3-Cl | 6-Cl | |
| 241 | H | n-$C_5H_{11}$ | 2-$CH_3$-3-Cl | 6-Cl | |
| 242 | H | neo-$C_5H_{11}$ | 2-$CH_3$-3-Cl | 6-Cl | |
| 243 | H | c-$C_5H_9$ | 2-$CH_3$-3-Cl | 6-Cl | 236–238 |
| 244 | H | t-$C_5H_{11}$ | 2-$CH_3$-3-Cl | 6-Cl | |
| 245 | H | n-$C_6H_{13}$ | 2-$CH_3$-3-Cl | 6-Cl | |
| 246 | H | $C_2H_5$ | 2,6-$(C_2H_5)_2$-3-Cl | 7-Cl | 238–240 |
| 247 | H | n-$C_3H_7$ | 2,6-$(C_2H_5)_2$-3-Cl | 7-Cl | |
| 248 | H | i-$C_3H_7$ | 2,6-$(C_2H_5)_2$-3-Cl | 7-Cl | |
| 249 | H | c-$C_3H_5$ | 2,6-$(C_2H_5)_2$-3-Cl | 7-Cl | |
| 250 | H | n-$C_4H_9$ | 2,6-$(C_2H_5)_2$-3-Cl | 7-Cl | |
| 251 | H | s-$C_4H_9$ | 2,6-$(C_2H_5)_2$-3-Cl | 7-Cl | |
| 252 | H | i-$C_4H_9$ | 2,6-$(C_2H_5)_2$-3-Cl | 7-Cl | |
| 253 | H | t-$C_4H_9$ | 2,6-$(C_2H_5)_2$-3-Cl | 7-Cl | |
| 254 | H | n-$C_5H_{11}$ | 2,6-$(C_2H_5)_2$-3-Cl | 7-Cl | |
| 255 | H | neo-$C_5H_{11}$ | 2,6-$(C_2H_5)_2$-3-Cl | 7-Cl | |
| 256 | H | c-$C_5H_9$ | 2,6-$(C_2H_5)_2$-3-Cl | 7-Cl | |
| 257 | H | t-$C_5H_{11}$ | 2,6-$(C_2H_5)_2$-3-Cl | 7-Cl | |
| 258 | H | n-$C_6H_{13}$ | 2,6-$(C_2H_5)_2$-3-Cl | 7-Cl | |
| 259 | H | $CH_3$ | 2-$CH_3$-3-Cl | 7-Cl | |
| 260 | H | $C_2H_5$ | 2-$CH_3$-3-Cl | 7-Cl | |
| 261 | H | n-$C_3H_7$ | 2-$CH_3$-3-Cl | 7-Cl | |
| 262 | H | i-$C_3H_7$ | 2-$CH_3$-3-Cl | 7-Cl | |
| 263 | H | c-$C_3H_5$ | 2-$CH_3$-3-Cl | 7-Cl | |
| 264 | H | n-$C_4H_9$ | 2-$CH_3$-3-Cl | 7-Cl | |
| 265 | H | s-$C_4H_9$ | 2-$CH_3$-3-Cl | 7-Cl | |
| 266 | H | i-$C_4H_9$ | 2-$CH_3$-3-Cl | 7-Cl | |
| 267 | H | t-$C_4H_9$ | 2-$CH_3$-3-Cl | 7-Cl | |
| 268 | H | n-$C_5H_{11}$ | 2-$CH_3$-3-Cl | 7-Cl | |
| 269 | H | neo-$C_5H_{11}$ | 2-$CH_3$-3-Cl | 7-Cl | |
| 270 | H | c-$C_5H_9$ | 2-$CH_3$-3-Cl | 7-Cl | |
| 271 | H | t-$C_5H_{11}$ | 2-$CH_3$-3-Cl | 7-Cl | |
| 272 | H | n-$C_6H_{13}$ | 2-$CH_3$-3-Cl | 7-Cl | |
| 273 | H | H | 2,6-$(C_2H_5)_2$-3-Cl | 6-OH | |
| 274 | H | $CH_3$ | 2,6-$(C_2H_5)_2$-3-Cl | 6-OH | |
| 275 | H | $C_2H_5$ | 2,6-$(C_2H_5)_2$-3-Cl | 6-OH | 239–241 |
| 276 | H | n-$C_3H_7$ | 2,6-$(C_2H_5)_2$-3-Cl | 6-OH | 266–267 |
| 277 | H | i-$C_3H_7$ | 2,6-$(C_2H_5)_2$-3-Cl | 6-OH | |
| 278 | H | c-$C_3H_5$ | 2,6-$(C_2H_5)_2$-3-Cl | 6-OH | |
| 279 | H | n-$C_4H_9$ | 2,6-$(C_2H_5)_2$-3-Cl | 6-OH | |
| 280 | H | s-$C_4H_9$ | 2,6-$(C_2H_5)_2$-3-Cl | 6-OH | |
| 281 | H | i-$C_4H_9$ | 2,6-$(C_2H_5)_2$-3-Cl | 6-OH | |
| 282 | H | t-$C_4H_9$ | 2,6-$(C_2H_5)_2$-3-Cl | 6-OH | |
| 283 | H | n-$C_5H_{11}$ | 2,6-$(C_2H_5)_2$-3-Cl | 6-OH | |
| 284 | H | neo-$C_5H_{11}$ | 2,6-$(C_2H_5)_2$-3-Cl | 6-OH | |
| 285 | H | c-$C_5H_9$ | 2,6-$(C_2H_5)_2$-3-Cl | 6-OH | |
| 286 | H | t-$C_5H_{11}$ | 2,6-$(C_2H_5)_2$-3-Cl | 6-OH | |
| 287 | H | n-$C_6H_{13}$ | 2,6-$(C_2H_5)_2$-3-Cl | 6-OH | |
| 288 | H | $CH_3$ | 2,6-$(C_2H_5)_2$-3-Cl | 6-$OCH_3$ | |
| 289 | H | $C_2H_5$ | 2,6-$(C_2H_5)_2$-3-Cl | 6-$OCH_3$ | 209–210 |
| 290 | H | n-$C_3H_7$ | 2,6-$(C_2H_5)_2$-3-Cl | 6-$OCH_3$ | 173–175 |
| 291 | H | i-$C_3H_7O$ | 2,6-$(C_2H_5)_2$-3-Cl | 6-$OCH_3$ | 178–181 |
| 292 | H | c-$C_3H_5$ | 2,6-$(C_2H_5)_2$-3-Cl | 6-$OCH_3$ | |
| 293 | H | n-$C_4H_9$ | 2,6-$(C_2H_5)_2$-3-Cl | 6-$OCH_3$ | |
| 294 | H | s-$C_4H_9$ | 2,6-$(C_2H_5)_2$-3-Cl | 6-$OCH_3$ | |
| 295 | H | i-$C_4H_9$ | 2,6-$(C_2H_5)_2$-3-Cl | 6-$OCH_3$ | |
| 296 | H | t-$C_4H_9$ | 2,6-$(C_2H_5)_2$-3-Cl | 6-$OCH_3$ | |
| 297 | H | n-$C_5H_{11}$ | 2,6-$(C_2H_5)_2$-3-Cl | 6-$OCH_3$ | |
| 298 | H | neo-$C_5H_{11}$ | 2,6-$(C_2H_5)_2$-3-Cl | 6-$OCH_3$ | |
| 299 | H | c-$C_5H_9$ | 2,6-$(C_2H_5)_2$-3-Cl | 6-$OCH_3$ | |
| 300 | H | t-$C_5H_{11}$ | 2,6-$(C_2H_5)_2$-3-Cl | 6-$OCH_3$ | |
| 301 | H | n-$C_6H_{13}$ | 2,6-$(C_2H_5)_2$-3-Cl | 6-$OCH_3$ | |
| 302 | H | H | 2,6-$(C_2H_5)_2$-3-Cl | 6,7-$(OCH_3)_2$ | |
| 303 | H | $CH_3$ | 2,6-$(C_2H_5)_2$-3-Cl | 6,7-$(OCH_3)_2$ | |
| 304 | H | $C_2H_5$ | 2,6-$(C_2H_5)_2$-3-Cl | 6,7-$(OCH_3)_2$ | |

TABLE 1-continued

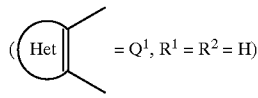
(Het = Q¹, R¹ = R² = H)

| No | Y | R³ | X | R⁴ | mp ° C. |
|---|---|---|---|---|---|
| 305 | H | n-C$_3$H$_7$ | 2,6-(C$_2$H$_5$)$_2$-3-Cl | 6,7-(OCH$_3$)$_2$ | 223–225 |
| 306 | H | i-C$_3$H$_7$ | 2,6-(C$_2$H$_5$)$_2$-3-Cl | 6,7-(OCH$_3$)$_2$ | |
| 307 | H | c-C$_3$H$_5$ | 2,6-(C$_2$H$_5$)$_2$-3-Cl | 6,7-(OCH$_3$)$_2$ | |
| 308 | H | n-C$_4$H$_9$ | 2,6-(C$_2$H$_5$)$_2$-3-Cl | 6,7-(OCH$_3$)$_2$ | |
| 309 | H | s-C$_4$H$_9$ | 2,6-(C$_2$H$_5$)$_2$-3-Cl | 6,7-(OCH$_3$)$_2$ | |
| 310 | H | i-C$_4$H$_9$ | 2,6-(C$_2$H$_5$)$_2$-3-Cl | 6,7-(OCH$_3$)$_2$ | 204-206 |
| 311 | H | t-C$_4$H$_9$ | 2,6-(C$_2$H$_5$)$_2$-3-Cl | 6,7-(OCH$_3$)$_2$ | |
| 312 | H | n-C$_5$H$_{11}$ | 2,6-(C$_2$H$_5$)$_2$-3-Cl | 6,7-(OCH$_3$)$_2$ | |
| 313 | H | neo-C$_5$H$_{11}$ | 2,6-(C$_2$H$_5$)$_2$-3-Cl | 6,7-(OCH$_3$)$_2$ | |
| 314 | H | c-C$_5$H$_9$ | 2,6-(C$_2$H$_5$)$_2$-3-Cl | 6,7-(OCH$_3$)$_2$ | |
| 315 | H | t-C$_5$H$_{11}$ | 2,6-(C$_2$H$_5$)$_2$-3-Cl | 6,7-(OCH$_3$)$_2$ | |
| 316 | H | n-C$_6$H$_{13}$ | 2,6-(C$_2$H$_5$)$_2$-3-Cl | 6,7-(OCH$_3$)$_2$ | |
| 317 | H | CH$_3$ | 2-CH$_3$-3-Cl | 6,7-(OCH$_3$)$_2$ | |
| 318 | H | C$_2$H$_5$ | 2-CH$_3$-3-Cl | 6,7-(OCH$_3$)$_2$ | |
| 319 | H | n-C$_3$H$_7$ | 2-CH$_3$-3-Cl | 6,7-(OCH$_3$)$_2$ | |
| 320 | H | i-C$_3$H$_7$ | 2-CH$_3$-3-Cl | 6,7-(OCH$_3$)$_2$ | |
| 321 | H | c-C$_3$H$_5$ | 2-CH$_3$-3-Cl | 6,7-(OCH$_3$)$_2$ | |
| 322 | H | n-C$_4$H$_9$ | 2-CH$_3$-3-Cl | 6,7-(OCH$_3$)$_2$ | |
| 323 | H | s-C$_4$H$_9$ | 2-CH$_3$-3-Cl | 6,7-(OCH$_3$)$_2$ | |
| 324 | H | i-C$_4$H$_9$ | 2-CH$_3$-3-Cl | 6,7-(OCH$_3$)$_2$ | |
| 325 | H | t-C$_4$H$_9$ | 2-CH$_3$-3-Cl | 6,7-(OCH$_3$)$_2$ | |
| 326 | H | n-C$_5$H$_{11}$ | 2-CH$_3$-3-Cl | 6,7-(OCH$_3$)$_2$ | |
| 327 | H | neo-C$_5$H$_{11}$ | 2-CH$_3$-3-Cl | 6,7-(OCH$_3$)$_2$ | |
| 328 | H | c-C$_5$H$_9$ | 2-CH$_3$-3-Cl | 6,7-(OCH$_3$)$_2$ | |
| 329 | H | t-C$_5$H$_{11}$ | 2-CH$_3$-3-Cl | 6,7-(OCH$_3$)$_2$ | |
| 330 | H | n-C$_6$H$_{13}$ | 2-CH$_3$-3-Cl | 6,7-(OCH$_3$)$_2$ | |
| 331 | H | H | 2,6-(C$_2$H$_5$)$_2$-3-Cl | 6,7-(OCH$_2$O) | |
| 332 | H | CH$_3$ | 2,6-(C$_2$H$_5$)$_2$-3-Cl | 6,7-(OCH$_2$O) | |
| 333 | H | C$_2$H$_5$ | 2,6-(C$_2$H$_5$)$_2$-3-Cl | 6,7-(OCH$_2$O) | |
| 334 | H | n-C$_3$H$_7$ | 2,6-(C$_2$H$_5$)$_2$-3-Cl | 6,7-(OCH$_2$O) | 213–215 |
| 335 | H | i-C$_3$H$_7$ | 2,6-(C$_2$H$_5$)$_2$-3-Cl | 6,7-(OCH$_2$O) | |
| 336 | H | c-C$_3$H$_5$ | 2,6-(C$_2$H$_5$)$_2$-3-Cl | 6,7-(OCH$_2$O) | |
| 337 | H | n-C$_4$H$_9$ | 2,6-(C$_2$H$_5$)$_2$-3-Cl | 6,7-(OCH$_2$O) | |
| 338 | H | s-C$_4$H$_9$ | 2,6-(C$_2$H$_5$)$_2$-3-Cl | 6,7-(OCH$_2$O) | |
| 339 | H | i-C$_4$H$_9$ | 2,6-(C$_2$H$_5$)$_2$-3-Cl | 6,7-(OCH$_2$O) | 221–223 |
| 340 | H | t-C$_4$H$_9$ | 2,6-(C$_2$H$_5$)$_2$-3-Cl | 6,7-(OCH$_2$O) | |
| 341 | H | n-C$_5$H$_{11}$ | 2,6-(C$_2$H$_5$)$_2$-3-Cl | 6,7-(OCH$_2$O) | |
| 342 | H | neo-C$_5$H$_{11}$ | 2,6-(C$_2$H$_5$)$_2$-3-Cl | 6,7-(OCH$_2$O) | |
| 343 | H | c-C$_5$H$_{11}$ | 2,6-(C$_2$H$_5$)$_2$-3-Cl | 6,7-(OCH$_2$O) | 191–193 |
| 344 | H | t-C$_5$H$_{11}$ | 2,6-(C$_2$H$_5$)$_2$-3-Cl | 6,7-(OCH$_2$O) | |
| 345 | H | n-C$_6$H$_{13}$ | 2,6-(C$_2$H$_5$)$_2$-3-Cl | 6,7-(OCH$_2$O) | |
| 346 | H | CH$_3$ | 2-CH$_3$-3-Cl | 6,7-(OCH$_2$O) | |
| 347 | H | C$_2$H$_5$ | 2-CH$_3$-3-Cl | 6,7-(OCH$_2$O) | |
| 348 | H | n-C$_3$H$_7$ | 2-CH$_3$-3-Cl | 6,7-(OCH$_2$O) | |
| 349 | H | i-C$_3$H$_7$ | 2-CH$_3$-3-Cl | 6,7-(OCH$_2$O) | |
| 350 | H | c-C$_3$H$_5$ | 2-CH$_3$-3-Cl | 6,7-(OCH$_2$O) | |
| 351 | H | n-C$_4$H$_9$ | 2-CH$_3$-3-Cl | 6,7-(OCH$_2$O) | |
| 352 | H | s-C$_4$H$_9$ | 2-CH$_3$-3-Cl | 6,7-(OCH$_2$O) | |
| 353 | H | i-C$_4$H$_9$ | 2-CH$_3$-3-Cl | 6,7-(OCH$_2$O) | |
| 354 | H | t-C$_4$H$_9$ | 2-CH$_3$-3-Cl | 6,7-(OCH$_2$O) | |
| 355 | H | n-C$_5$H$_{11}$ | 2-CH$_3$-3-Cl | 6,7-(OCH$_2$O) | |
| 356 | H | neo-C$_5$H$_{11}$ | 2-CH$_3$-3-Cl | 6,7-(OCH$_2$O) | |
| 357 | H | c-C$_5$H$_9$ | 2-CH$_3$-3-Cl | 6,7-(OCH$_2$O) | |
| 358 | H | t-C$_5$H$_{11}$ | 2-CH$_3$-3-Cl | 6,7-(OCH$_2$O) | |
| 359 | H | n-C$_6$H$_{13}$ | 2-CH$_3$-3-Cl | 6,7-(OCH$_2$O) | |

TABLE 1-continued

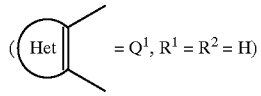
(Het) = Q¹, R¹ = R² = H)

| No | Y | R³ | X | R⁴ | mp ° C. |
|---|---|---|---|---|---|
| 359-1 | H | CH₃ | 2,6-(C₂H₅)₂-3-Cl | H | 235–237 |
| 359-2 | H | C₂H₅ | 2,6-(C₂H₅)₂-3-Cl | H | 205–207 |
| 359-3 | H | n-C₃H₇ | 2,6-(C₂H₅)₂-3-Cl | H | 211–213 |
| 359-4 | H | t-C₄H₉ | 2,6-(C₂H₅)₂-3-Cl | H | 195–197 |
| 359-5 | H | neo-C₅H₁₁ | 2,6-(C₂H₅)₂-3-Cl | H | 141–143 |
| 359-6 | H | c-C₅H₉ | 2,6-(C₂H₅)₂-3-Cl | H | 161–163 |

TABLE 2

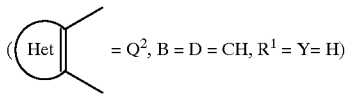
(Het) = Q², B = D = CH, R¹ = Y = H)

| No | R² | R³ | X | A | E | mp ° C. |
|---|---|---|---|---|---|---|
| 360 | H | C₂H₅ | 2,6-(C₂H₅)₂-3-Cl | N | CH | 249–264 |
| 361 | H | n-C₃H₇ | 2,6-(C₂H₅)₂-3-Cl | N | CH | 234–250 |
| 362 | H | i-C₃H₇ | 2,6-(C₂H₅)₂-3-Cl | N | CH | |
| 363 | H | c-C₃H₅ | 2,6-(C₂H₅)₂-3-Cl | N | CH | |
| 364 | H | n-C₄H₉ | 2,6-(C₂H₅)₂-3-Cl | N | CH | |
| 365 | H | s-C₄H₉ | 2,6-(C₂H₅)₂-3-Cl | N | CH | |
| 366 | H | i-C₄H₉ | 2,6-(C₂H₅)₂-3-Cl | N | CH | |
| 367 | H | t-C₄H₉ | 2,6-(C₂H₅)₂-3-Cl | N | CH | |
| 368 | H | n-C₅H₁₁ | 2,6-(C₂H₅)₂-3-Cl | N | CH | |
| 369 | H | neo-C₅H₁₁ | 2,6-(C₂H₅)₂-3-Cl | N | OH | |
| 370 | H | c-C₅H₉ | 2,6-(C₂H₅)₂-3-Cl | N | CH | |
| 371 | H | t-C₅H₁₁ | 2,6-(C₂H₅)₂-3-Cl | N | CH | |
| 372 | H | n-C₆H₁₃ | 2,6-(C₂H₅)₂-3-Cl | N | CH | |
| 373 | H | CH₃ | 2-CH₃-3-Cl | N | CH | |
| 374 | H | C₂H₅ | 2-CH₃-3-Cl | N | CH | |
| 375 | H | n-C₃H₇ | 2-CH₃-3-Cl | N | CH | 223–245 |
| 376 | H | i-C₃H₇ | 2-CH₃-3-Cl | N | CH | |
| 377 | H | c-C₃H₅ | 2-CH₃-3-Cl | N | CH | |
| 378 | H | n-C₄H₉ | 2-CH₃-3-Cl | N | CH | |
| 379 | H | s-C₄H₉ | 2-CH₃-3-Cl | N | CH | |
| 380 | H | i-C₄H₉ | 2-CH₃-3-Cl | N | CH | |
| 381 | H | t-C₄H₉ | 2-CH₃-3-Cl | N | CH | |
| 382 | H | n-C₅H₁₁ | 2-CH₃-3-Cl | N | CH | |
| 383 | H | neo-C₅H₁₁ | 2-CH₃-3-Cl | N | CH | |
| 384 | H | c-C₅H₉ | 2-CH₃-3-Cl | N | CH | |
| 385 | H | t-C₅H₁₁ | 2-CH₃-3-Cl | N | CH | |
| 386 | H | n-C₆H₁₃ | 2-CH₃-3-Cl | N | CH | |
| 387 | H | C₂H₅ | 2,6-(C₂H₅)₂-3-Cl | N | N | |
| 388 | H | n-C₃H₇ | 2,6-(C₂H₅)₂-3-Cl | N | N | 215–220 |
| 389 | H | i-C₃H₇ | 2,6-(C₂H₅)₂-3-Cl | N | N | |

TABLE 2-continued

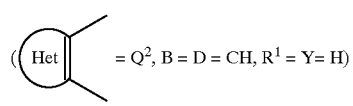
(Het) = Q², B = D = CH, R¹ = Y = H)

| No | R² | R³ | X | A | E | mp ° C. |
|---|---|---|---|---|---|---|
| 390 | H | c-C₃H₅ | 2,6-(C₂H₅)₂-3-Cl | N | N | |
| 391 | H | n-C₄H₉ | 2,6-(C₂H₅)₂-3-Cl | N | N | |
| 392 | H | s-C₄H₉ | 2,6-(C₂H₅)₂-3-Cl | N | N | |
| 393 | H | i-C₄H₉ | 2,6-(C₂H₅)₂-3-Cl | N | N | |
| 394 | H | t-C₄H₉ | 2,6-(C₂H₅)₂-3-Cl | N | N | |
| 395 | H | n-C₅H₁₁ | 2,6-(C₂H₅)₂-3-Cl | N | N | |
| 396 | H | neo-C₅H₁₁ | 2,6-(C₂H₅)₂-3-Cl | N | N | |
| 397 | H | c-C₅H₉ | 2,6-(C₂H₅)₂-3-Cl | N | N | |
| 398 | H | t-C₅H₁₁ | 2,6-(C₂H₅)₂-3-Cl | N | N | |
| 399 | H | n-C₆H₁₃ | 2,6-(C₂H₅)₂-3-Cl | N | N | |
| 400 | H | CH₃ | 2-CH₃-3-Cl | N | N | |
| 401 | H | C₂H₅ | 2-CH₃-3-Cl | N | N | |
| 402 | H | n-C₃H₇ | 2-CH₃-3-Cl | N | N | |
| 403 | H | i-C₃H₇ | 2-CH₃-3-Cl | N | N | |
| 404 | H | c-C₃H₅ | 2-CH₃-3-Cl | N | N | |
| 405 | H | n-C₄H₉ | 2-CH₃-3-Cl | N | N | |
| 406 | H | s-C₄H₉ | 2-CH₃-3-Cl | N | N | |
| 407 | H | i-C₄H₉ | 2-CH₃-3-Cl | N | N | |
| 408 | H | t-C₄H₉ | 2-CH₃-3-Cl | N | N | |
| 409 | H | n-C₅H₁₁ | 2-CH₃-3-Cl | N | N | |
| 410 | H | neo-C₅H₁₁ | 2-CH₃-3-Cl | N | N | |
| 411 | H | c-C₅H₉ | 2-CH₃-3-Cl | N | N | |
| 412 | H | t-C₅H₁₁ | 2-CH₃-3-Cl | N | N | |

TABLE 3

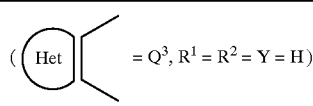
(Het) = Q³, R¹ = R² = Y = H)

| No | R³ | X | F | G | J | K | mp ° C. |
|---|---|---|---|---|---|---|---|
| 413 | C₂H₅ | 2,6-(C₂H₅)₂-3-Cl | O | CH₂ | CH₂ | CH₂ | |
| 414 | n-C₃H₇ | 2,6-(C₂H₅)₂-3-Cl | O | CH₂ | CH₂ | CH₂ | 188–191 |
| 415 | i-C₃H₇ | 2,6-(C₂H₅)₂-3-Cl | O | CH₂ | CH₂ | CH₂ | |
| 416 | c-C₃H₅ | 2,6-(C₂H₅)₂-3-Cl | O | CH₂ | CH₂ | CH₂ | |
| 417 | n-C₄H₉ | 2,6-(C₂H₅)₂-3-Cl | O | CH₂ | CH₂ | CH₂ | |
| 418 | s-C₄H₉ | 2,6-(C₂H₅)₂-3-Cl | O | CH₂ | CH₂ | CH₂ | |
| 419 | i-C₄H₉ | 2,6-(C₂H₅)₂-3-Cl | O | CH₂ | CH₂ | CH₂ | |
| 420 | t-C₄H₉ | 2,6-(C₂H₅)₂-3-Cl | O | CH₂ | CH₂ | CH₂ | |

TABLE 3-continued

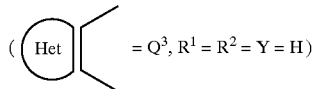 = $Q^3$, $R^1 = R^2 = Y = H$)

| No | $R^3$ | X | F | G | J | K | mp °C. |
|---|---|---|---|---|---|---|---|
| 421 | n-$C_5H_{11}$ | 2,6-$(C_2H_5)_2$-3-Cl | O | $CH_2$ | $CH_2$ | $CH_2$ | |
| 422 | neo-$C_5H_{11}$ | 2,6-$(C_2H_5)_2$-3-Cl | O | $CH_2$ | $CH_2$ | $CH_2$ | |
| 423 | c-$C_5H_9$ | 2,6-$(C_2H_5)_2$-3-Cl | O | $CH_2$ | $CH_2$ | $CH_2$ | 185–189 |
| 424 | t-$C_5H_{11}$ | 2,6-$(C_2H_5)_2$-3-Cl | O | $CH_2$ | $CH_2$ | $CH_2$ | |
| 425 | $C_2H_5$ | 2-$CH_3$-3-Cl | O | $CH_2$ | $CH_2$ | $CH_2$ | |
| 426 | n-$C_3H_7$ | 2-$CH_3$-3-Cl | O | $CH_2$ | $CH_2$ | $CH_2$ | |
| 427 | i-$C_3H_7$ | 2-$CH_3$-3-Cl | O | $CH_2$ | $CH_2$ | $CH_2$ | |
| 428 | c-$C_3H_5$ | 2-$CH_3$-3-Cl | O | $CH_2$ | $CH_2$ | $CH_2$ | |
| 429 | n-$C_4H_9$ | 2-$CH_3$-3-Cl | O | $CH_2$ | $CH_2$ | $CH_2$ | |
| 430 | s-$C_4H_9$ | 2-$CH_3$-3-Cl | O | $CH_2$ | $CH_2$ | $CH_2$ | |
| 431 | i-$C_4H_9$ | 2-$CH_3$-3-Cl | O | $CH_2$ | $CH_2$ | $CH_2$ | 180–183 |
| 432 | t-$C_4H_9$ | 2-$CH_3$-3-Cl | O | $CH_2$ | $CH_2$ | $CH_2$ | |
| 433 | n-$C_5H_{11}$ | 2-$CH_3$-3-Cl | O | $CH_2$ | $CH_2$ | $CH_2$ | |
| 434 | neo-$C_5H_{11}$ | 2-$CH_3$-3-Cl | O | $CH_2$ | $CH_2$ | $CH_2$ | |
| 435 | c-$C_5H_9$ | 2-$CH_3$-3-Cl | O | $CH_2$ | $CH_2$ | $CH_2$ | |
| 436 | t-$C_5H_{11}$ | 2-$CH_3$-3-Cl | O | $CH_2$ | $CH_2$ | $CH_2$ | |
| 437 | $C_2H_5$ | 2,6-$(C_2H_5)_2$-3-Cl | $CH_2$ | O | $CH_2$ | $CH_2$ | |
| 438 | n-$C_3H_7$ | 2,6-$(C_2H_5)_2$-3-Cl | $CH_2$ | O | $CH_2$ | $CH_2$ | 190–194 |
| 439 | i-$C_3H_7$ | 2,6-$(C_2H_5)_2$-3-Cl | $CH_2$ | O | $CH_2$ | $CH_2$ | |
| 440 | c-$C_3H_5$ | 2,6-$(C_2H_5)_2$-3-Cl | $CH_2$ | O | $CH_2$ | $CH_2$ | |
| 441 | n-$C_4H_9$ | 2,6-$(C_2H_5)_2$-3-Cl | $CH_2$ | O | $CH_2$ | $CH_2$ | |
| 442 | s-$C_4H_9$ | 2,6-$(C_2H_5)_2$-3-Cl | $CH_2$ | O | $CH_2$ | $CH_2$ | |
| 443 | i-$C_4H_9$ | 2,6-$(C_2H_5)_2$-3-Cl | $CH_2$ | O | $CH_2$ | $CH_2$ | |
| 444 | t-$C_4H_9$ | 2,6-$(C_2H_5)_2$-3-Cl | $CH_2$ | O | $CH_2$ | $CH_2$ | |
| 445 | n-$C_5H_{11}$ | 2,6-$(C_2H_5)_2$-3-Cl | $CH_2$ | O | $CH_2$ | $CH_2$ | |
| 446 | neo-$C_5H_{11}$ | 2,6-$(C_2H_5)_2$-3-Cl | $CH_2$ | O | $CH_2$ | $CH_2$ | |
| 447 | c-$C_5H_9$ | 2,6-$(C_2H_5)_2$-3-Cl | $CH_2$ | O | $CH_2$ | $CH_2$ | 187–190 |
| 448 | t-$C_5H_{11}$ | 2,6-$(C_2H_5)_2$-3-Cl | $CH_2$ | O | $CH_2$ | $CH_2$ | |
| 449 | $C_2H_5$ | 2-$CH_3$-3-Cl | $CH_2$ | O | $CH_2$ | $CH_2$ | |
| 450 | n-$C_3H_7$ | 2-$CH_3$-3-Cl | $CH_2$ | O | $CH_2$ | $CH_2$ | 188–190 |
| 451 | i-$C_3H_7$ | 2-$CH_3$-3-Cl | $CH_2$ | O | $CH_2$ | $CH_2$ | |
| 452 | c-$C_3H_5$ | 2-$CH_3$-3-Cl | $CH_2$ | O | $CH_2$ | $CH_2$ | |
| 453 | n-$C_4H_9$ | 2-$CH_3$-3-Cl | $CH_2$ | O | $CH_2$ | $CH_2$ | |
| 454 | s-$C_4H_9$ | 2-$CH_3$-3-Cl | $CH_2$ | O | $CH_2$ | $CH_2$ | |
| 455 | i-$C_4H_9$ | 2-$CH_3$-3-Cl | $CH_2$ | O | $CH_2$ | $CH_2$ | |
| 456 | t-$C_4H_9$ | 2-$CH_3$-3-Cl | $CH_2$ | O | $CH_2$ | $CH_2$ | |
| 457 | n-$C_5H_{11}$ | 2-$CH_3$-3-Cl | $CH_2$ | O | $CH_2$ | $CH_2$ | |
| 458 | neo-$C_5H_{11}$ | 2-$CH_3$-3-Cl | $CH_2$ | O | $CH_2$ | $CH_2$ | |
| 459 | c-$C_5H_9$ | 2-$CH_3$-3-Cl | $CH_2$ | O | $CH_2$ | $CH_2$ | |
| 460 | t-$C_5H_{11}$ | 2-$CH_3$-3-Cl | $CH_2$ | O | $CH_2$ | $CH_2$ | |
| 461 | $C_2H_5$ | 2,6-$(C_2H_5)_2$-3-Cl | $CH_2$ | $CH_2$ | O | $CH_2$ | |
| 462 | n-$C_3H_7$ | 2,6-$(C_2H_5)_2$-3-Cl | $CH_2$ | $CH_2$ | O | $CH_2$ | 166–170 |
| 463 | i-$C_3H_7$ | 2,6-$(C_2H_5)_2$-3-Cl | $CH_2$ | $CH_2$ | O | $CH_2$ | |
| 464 | c-$C_3H_5$ | 2,6-$(C_2H_5)_2$-3-Cl | $CH_2$ | $CH_2$ | O | $CH_2$ | |
| 465 | n-$C_4H_9$ | 2,6-$(C_2H_5)_2$-3-Cl | $CH_2$ | $CH_2$ | O | $CH_2$ | |
| 466 | s-$C_4H_9$ | 2,6-$(C_2H_5)_2$-3-Cl | $CH_2$ | $CH_2$ | O | $CH_2$ | |
| 467 | i-$C_4H_9$ | 2,6-$(C_2H_5)_2$-3-Cl | $CH_2$ | $CH_2$ | O | $CH_2$ | |
| 468 | t-$C_4H_9$ | 2,6-$(C_2H_5)_2$-3-Cl | $CH_2$ | $CH_2$ | O | $CH_2$ | |
| 469 | n-$C_5H_{11}$ | 2,6-$(C_2H_5)_2$-3-Cl | $CH_2$ | $CH_2$ | O | $CH_2$ | |
| 470 | neo-$C_5H_{11}$ | 2,6-$(C_2H_5)_2$-3-Cl | $CH_2$ | $CH_2$ | O | $CH_2$ | |
| 471 | c-$C_5H_9$ | 2,6-$(C_2H_5)_2$-3-Cl | $CH_2$ | $CH_2$ | O | $CH_2$ | |
| 472 | t-$C_5H_{11}$ | 2,6-$(C_2H_5)_2$-3-Cl | $CH_2$ | $CH_2$ | O | $CH_2$ | |
| 473 | $C_2H_5$ | 2-$CH_3$-3-Cl | $CH_2$ | $CH_2$ | O | $CH_2$ | |
| 474 | n-$C_3H_7$ | 2-$CH_3$-3-Cl | $CH_2$ | $CH_2$ | O | $CH_2$ | 168–171 |
| 475 | i-$C_3H_7$ | 2-$CH_3$-3-Cl | $CH_2$ | $CH_2$ | O | $CH_2$ | |
| 476 | c-$C_3H_5$ | 2-$CH_3$-3-Cl | $CH_2$ | $CH_2$ | O | CH | |
| 477 | n-$C_4H_9$ | 2-$CH_3$-3-Cl | $CH_2$ | $CH_2$ | O | $CH_2$ | |
| 478 | s-$C_4H_9$ | 2-$CH_3$-3-Cl | $CH_2$ | $CH_2$ | O | $CH_2$ | |
| 479 | i-$C_4H_9$ | 2-$CH_3$-3-Cl | $CH_2$ | $CH_2$ | O | $CH_2$ | |
| 480 | t-$C_4H_9$ | 2-$CH_3$-3-Cl | $CH_2$ | $CH_2$ | O | $CH_2$ | |
| 481 | n-$C_5H_{11}$ | 2-$CH_3$-3-Cl | $CH_2$ | $CH_2$ | O | $CH_2$ | |
| 482 | neo-$C_5H_{11}$ | 2-$CH_3$-3-Cl | $CH_2$ | $CH_2$ | O | $CH_2$ | |
| 483 | c-$C_5H_9$ | 2-$CH_3$-3-Cl | $CH_2$ | $CH_2$ | O | $CH_2$ | |
| 484 | t-$C_5H_{11}$ | 2-$CH_3$-3-Cl | $CH_2$ | $CH_2$ | O | $CH_2$ | |
| 485 | $C_2H_5$ | 2,6-$(C_2H_5)_2$-3-Cl | $CH_2$ | $CH_2$ | $CH_2$ | O | |
| 486 | n-$C_3H_7$ | 2,6-$(C_2H_5)_2$-3-Cl | $CH_2$ | $CH_2$ | $CH_2$ | O | 194–196 |
| 487 | i-$C_3H_7$ | 2,6-$(C_2H_5)_2$-3-Cl | $CH_2$ | $CH_2$ | $CH_2$ | O | |
| 488 | c-$C_3H_5$ | 2,6-$(C_2H_5)_2$-3-Cl | $CH_2$ | $CH_2$ | $CH_2$ | O | |
| 489 | n-$C_4H_9$ | 2,6-$(C_2H_5)_2$-3-Cl | $CH_2$ | $CH_2$ | $CH_2$ | O | |
| 490 | s-$C_4H_9$ | 2,6-$(C_2H_5)_2$-3-Cl | $CH_2$ | $CH_2$ | $CH_2$ | O | |
| 491 | i-$C_4H_9$ | 2,6-$(C_2H_5)_2$-3-Cl | $CH_2$ | $CH_2$ | $CH_2$ | O | |

TABLE 3-continued

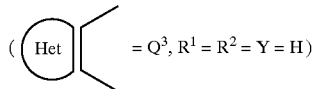 = Q³, R¹ = R² = Y = H )

| No | R³ | X | F | G | J | K | mp ° C. |
|---|---|---|---|---|---|---|---|
| 492 | t-$C_4H_9$ | 2,6-$(C_2H_5)_2$-3-Cl | $CH_2$ | $CH_2$ | $CH_2$ | O | |
| 493 | n-$C_5H_{11}$ | 2,6-$(C_2H_5)_2$-3-Cl | $CH_2$ | $CH_2$ | $CH_2$ | O | |
| 494 | neo-$C_5H_{11}$ | 2,6-$(C_2H_5)_2$-3-Cl | $CH_2$ | $CH_2$ | $CH_2$ | O | |
| 495 | c-$C_5H_9$ | 2,6-$(C_2H_5)_2$-3-Cl | $CH_2$ | $CH_2$ | $CH_2$ | O | |
| 496 | t-$C_5H_{11}$ | 2,6-$(C_2H_5)_2$-3-Cl | $CH_2$ | $CH_2$ | $CH_2$ | O | |
| 497 | $C_2H_5$ | 2-$CH_3$-3-Cl | $CH_2$ | $CH_2$ | $CH_2$ | O | |
| 498 | n-$C_3H_7$ | 2-$CH_3$-3-Cl | $CH_2$ | $CH_2$ | $CH_2$ | O | 195–198 |
| 499 | i-$C_3H_7$ | 2-$CH_3$-3-Cl | $CH_2$ | $CH_2$ | $CH_2$ | O | |
| 500 | c-$C_3H_5$ | 2-$CH_3$-3-Cl | $CH_2$ | $CH_2$ | $CH_2$ | O | |
| 501 | n-$C_4H_9$ | 2-$CH_3$-3-Cl | $CH_2$ | $CH_2$ | $CH_2$ | O | |
| 502 | s-$C_4H_9$ | 2-$CH_3$-3-Cl | $CH_2$ | $CH_2$ | $CH_2$ | O | |
| 503 | i-$C_4H_9$ | 2-$CH_3$-3-Cl | $CH_2$ | $CH_2$ | $CH_2$ | O | |
| 504 | t-$C_4H_9$ | 2-$CH_3$-3-Cl | $CH_2$ | $CH_2$ | $CH_2$ | O | |
| 505 | n-$C_5H_{11}$ | 2-$CH_3$-3-Cl | $CH_2$ | $CH_2$ | $CH_2$ | O | |
| 506 | neo-$C_5H_{11}$ | 2-$CH_3$-3-Cl | $CH_2$ | $CH_2$ | $CH_2$ | O | |
| 507 | c-$C_5H_9$ | 2-$CH_3$-3-Cl | $CH_2$ | $CH_2$ | $CH_2$ | O | |
| 508 | t-$C_5H_{11}$ | 2-$CH_3$-3-Cl | $CH_2$ | $CH_2$ | $CH_2$ | O | |
| 509 | $C_2H_5$ | 2,6-$(C_2H_5)_2$-3-Cl | S | $CH_2$ | $CH_2$ | $CH_2$ | |
| 510 | n-$C_3H_7$ | 2,6-$(C_2H_5)_2$-3-Cl | S | $CH_2$ | $CH_2$ | $CH_2$ | 181–183 |
| 511 | i-$C_3H_7$ | 2,6-$(C_2H_5)_2$-3-Cl | S | $CH_2$ | $CH_2$ | $CH_2$ | |
| 512 | c-$C_3H_5$ | 2,6-$(C_2H_5)_2$-3-Cl | S | $CH_2$ | $CH_2$ | $CH_2$ | |
| 513 | n-$C_4H_9$ | 2,6-$(C_2H_5)_2$-3-Cl | S | $CH_2$ | $CH_2$ | $CH_2$ | |
| 514 | s-$C_4H_9$ | 2,6-$(C_2H_5)_2$-3-Cl | S | $CH_2$ | $CH_2$ | $CH_2$ | |
| 515 | i-$C_4H_9$ | 2,6-$(C_2H_5)_2$-3-Cl | S | $CH_2$ | $CH_2$ | $CH_2$ | |
| 516 | t-$C_4H_9$ | 2,6-$(C_2H_5)_2$-3-Cl | S | $CH_2$ | $CH_2$ | $CH_2$ | |
| 517 | n-$C_5H_{11}$ | 2,6-$(C_2H_5)_2$-3-Cl | S | $CH_2$ | $CH_2$ | $CH_2$ | |
| 518 | neo-$C_5H_{11}$ | 2,6-$(C_2H_5)_2$-3-Cl | S | $CH_2$ | $CH_2$ | $CH_2$ | |
| 519 | c-$C_5H_9$ | 2,6-$(C_2H_5)_2$-3-Cl | S | $CH_2$ | $CH_2$ | $CH_2$ | 175–180 |
| 520 | t-$C_5H_{11}$ | 2,6-$(C_2H_5)_2$-3-Cl | S | $CH_2$ | $CH_2$ | $CH_2$ | |
| 521 | $C_2H_5$ | 2-$CH_3$-3-Cl | S | $CH_2$ | $CH_2$ | $CH_2$ | |
| 522 | n-$C_3H_7$ | 2-$CH_3$-3-Cl | S | $CH_2$ | $CH_2$ | $CH_2$ | |
| 523 | i-$C_3H_7$ | 2-$CH_3$-3-Cl | S | $CH_2$ | $CH_2$ | $CH_2$ | |
| 524 | c-$C_3H_5$ | 2-$CH_3$-3-Cl | S | $CH_2$ | $CH_2$ | $CH_2$ | |
| 525 | n-$C_4H_9$ | 2-$CH_3$-3-Cl | S | $CH_2$ | $CH_2$ | $CH_2$ | |
| 526 | s-$C_4H_9$ | 2-$CH_3$-3-Cl | S | $CH_2$ | $CH_2$ | $CH_2$ | |
| 527 | i-$C_4H_9$ | 2-$CH_3$-3-Cl | S | $CH_2$ | $CH_2$ | $CH_2$ | 178–181 |
| 528 | t-$C_4H_9$ | 2-$CH_3$-3-Cl | S | $CH_2$ | $CH_2$ | $CH_2$ | |
| 529 | n-$C_5H_{11}$ | 2-$CH_3$-3-Cl | S | $CH_2$ | $CH_2$ | $CH_2$ | |
| 530 | neo-$C_5H_{11}$ | 2-$CH_3$-3-Cl | S | $CH_2$ | $CH_2$ | $CH_2$ | |
| 531 | c-$C_5H_9$ | 2-$CH_3$-3-Cl | S | $CH_2$ | $CH_2$ | $CH_2$ | |
| 532 | t-$C_5H_{11}$ | 2-$CH_3$-3-Cl | S | $CH_2$ | $CH_2$ | $CH_2$ | |
| 533 | $C_2H_5$ | 2,6-$(C_2H_5)_2$-3-Cl | $CH_2$ | S | $CH_2$ | $CH_2$ | |
| 534 | n-$C_3H_7$ | 2,6-$(C_2H_5)_2$-3-Cl | $CH_2$ | S | $CH_2$ | $CH_2$ | 180–184 |
| 535 | i-$C_3H_7$ | 2,6-$(C_2H_5)_2$-3-Cl | $CH_2$ | S | $CH_2$ | $CH_2$ | |
| 536 | c-$C_3H_5$ | 2,6-$(C_2H_5)_2$-3-Cl | $CH_2$ | S | $CH_2$ | $CH_2$ | |
| 537 | n-$C_4H_9$ | 2,6-$(C_2H_5)_2$-3-Cl | $CH_2$ | S | $CH_2$ | $CH_2$ | |
| 538 | s-$C_4H_9$ | 2,6-$(C_2H_5)_2$-3-Cl | $CH_2$ | S | $CH_2$ | $CH_2$ | |
| 539 | i-$C_4H_9$ | 2,6-$(C_2H_5)_2$-3-Cl | $CH_2$ | S | $CH_2$ | $CH_2$ | |
| 540 | t-$C_4H_9$ | 2,6-$(C_2H_5)_2$-3-Cl | $CH_2$ | S | $CH_2$ | $CH_2$ | |
| 541 | n-$C_5H_{11}$ | 2,6-$(C_2H_5)_2$-3-Cl | $CH_2$ | S | $CH_2$ | $CH_2$ | |
| 542 | neo-$C_5H_{11}$ | 2,6-$(C_2H_5)_2$-3-Cl | $CH_2$ | S | $CH_2$ | $CH_2$ | |
| 543 | c-$C_5H_9$ | 2,6-$(C_2H_5)_2$-3-Cl | $CH_2$ | S | $CH_2$ | $CH_2$ | |
| 544 | t-$C_5H_{11}$ | 2,6-$(C_2H_5)_2$-3-Cl | $CH_2$ | S | $CH_2$ | $CH_2$ | |
| 545 | $C_2H_5$ | 2-$CH_3$-3-Cl | $CH_2$ | S | $CH_2$ | $CH_2$ | |
| 546 | n-$C_3H_7$ | 2-$CH_3$-3-Cl | $CH_2$ | S | $CH_2$ | $CH_2$ | |
| 547 | i-$C_3H_7$ | 2-$CH_3$-3-Cl | $CH_2$ | S | $CH_2$ | $CH_2$ | |
| 548 | c-$C_3H_5$ | 2-$CH_3$-3-Cl | $CH_2$ | S | $CH_2$ | $CH_2$ | |
| 549 | n-$C_4H_9$ | 2-$CH_3$-3-Cl | $CH_2$ | S | $CH_2$ | $CH_2$ | |
| 550 | s-$C_4H_9$ | 2-$CH_3$-3-Cl | $CH_2$ | S | $CH_2$ | $CH_2$ | |
| 551 | i-$C_4H_9$ | 2-$CH_3$-3-Cl | $CH_2$ | S | $CH_2$ | $CH_2$ | |
| 552 | t-$C_4H_9$ | 2-$CH_3$-3-Cl | $CH_2$ | S | $CH_2$ | $CH_2$ | |
| 553 | n-$C_5H_{11}$ | 2-$CH_3$-3-Cl | $CH_2$ | S | $CH_2$ | $CH_2$ | |
| 554 | neo-$C_5H_{11}$ | 2-$CH_3$-3-Cl | $CH_2$ | S | $CH_2$ | $CH_2$ | |
| 555 | c-$C_5H_9$ | 2-$CH_3$-3-Cl | $CH_2$ | S | $CH_2$ | $CH_2$ | |
| 556 | t-$C_5H_{11}$ | 2-$CH_3$-3-Cl | $CH_2$ | S | $CH_2$ | $CH_2$ | |
| 557 | $C_2H_5$ | 2,6-$(C_2H_5)_2$-3-Cl | $CH_2$ | $CH_2$ | S | $CH_2$ | |
| 558 | n-$C_3H_7$ | 2,6-$(C_2H_5)_2$-3-Cl | $CH_2$ | $CH_2$ | S | $CH_2$ | 179–180 |
| 559 | i-$C_3H_7$ | 2,6-$(C_2H_5)_2$-3-Cl | $CH_2$ | $CH_2$ | S | $CH_2$ | |
| 560 | c-$C_3H_5$ | 2,6-$(C_2H_5)_2$-3-Cl | $CH_2$ | $CH_2$ | S | $CH_2$ | |
| 561 | n-$C_4H_9$ | 2,6-$(C_2H_5)_2$-3-Cl | $CH_2$ | $CH_2$ | S | $CH_2$ | |
| 562 | s-$C_4H_9$ | 2,6-$(C_2H_5)_2$-3-Cl | $CH_2$ | $CH_2$ | S | $CH_2$ | |

TABLE 3-continued

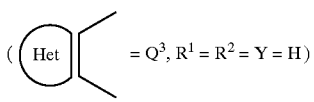 = $Q^3$, $R^1 = R^2 = Y = H$ )

| No | $R^3$ | X | F | G | J | K | mp °C. |
|---|---|---|---|---|---|---|---|
| 563 | i-$C_4H_9$ | 2,6-$(C_2H_5)_2$-3-Cl | $CH_2$ | $CH_2$ | S | $CH_2$ | |
| 564 | t-$C_4H_9$ | 2,6-$(C_2H_5)_2$-3-Cl | $CH_2$ | $CH_2$ | S | $CH_2$ | |
| 565 | n-$C_5H_{11}$ | 2,6-$(C_2H_5)_2$-3-Cl | $CH_2$ | $CH_2$ | S | $CH_2$ | |
| 566 | neo-$C_5H_{11}$ | 2,6-$(C_2H_5)_2$-3-Cl | $CH_2$ | $CH_2$ | S | $CH_2$ | |
| 567 | c-$C_5H_9$ | 2,6-$(C_2H_5)_2$-3-Cl | $CH_2$ | $CH_2$ | S | $CH_2$ | |
| 568 | t-$C_5H_{11}$ | 2,6-$(C_2H_5)_2$-3-Cl | $CH_2$ | $CH_2$ | S | $CH_2$ | |
| 569 | $C_2H_5$ | 2-$CH_3$-3-Cl | $CH_2$ | $CH_2$ | S | $CH_2$ | |
| 570 | n-$C_3H_7$ | 2-$CH_3$-3-Cl | $CH_2$ | $CH_2$ | S | $CH_2$ | 182–185 |
| 571 | i-$C_3H_7$ | 2-$CH_3$-3-Cl | $CH_2$ | $CH_2$ | S | $CH_2$ | |
| 572 | c-$C_3H_5$ | 2-$CH_3$-3-Cl | $CH_2$ | $CH_2$ | S | $CH_2$ | |
| 573 | n-$C_4H_9$ | 2-$CH_3$-3-Cl | $CH_2$ | $CH_2$ | S | $CH_2$ | |
| 574 | s-$C_4H_9$ | 2-$CH_3$-3-Cl | $CH_2$ | $CH_2$ | S | $CH_2$ | |
| 575 | i-$C_4H_9$ | 2-$CH_3$-3-Cl | $CH_2$ | $CH_2$ | S | $CH_2$ | |
| 576 | t-$C_4H_9$ | 2-$CH_3$-3-Cl | $CH_2$ | $CH_2$ | S | $CH_2$ | |
| 577 | n-$C_5H_{11}$ | 2-$CH_3$-3-Cl | $CH_2$ | $CH_2$ | S | $CH_2$ | |
| 578 | neo-$C_5H_{11}$ | 2-$CH_3$-3-Cl | $CH_2$ | $CH_2$ | S | $CH_2$ | |
| 579 | c-$C_5H_9$ | 2-$CH_3$-3-Cl | $CH_2$ | $CH_2$ | S | $CH_2$ | |
| 580 | t-$C_5H_{11}$ | 2-$CH_3$-3-Cl | $CH_2$ | $CH_2$ | S | $CH_2$ | |
| 581 | $C_2H_5$ | 2,6-$(C_2H_5)_2$-3-Cl | $CH_2$ | $CH_2$ | $CH_2$ | S | |
| 582 | n-$C_3H_7$ | 2,6-$(C_2H_5)_2$-3-Cl | $CH_2$ | $CH_2$ | $CH_2$ | S | 186–190 |
| 583 | i-$C_3H_7$ | 2,6-$(C_2H_5)_2$-3-Cl | $CH_2$ | $CH_2$ | $CH_2$ | S | |
| 584 | c-$C_3H_5$ | 2,6-$(C_2H_5)_2$-3-Cl | $CH_2$ | $CH_2$ | $CH_2$ | S | |
| 585 | n-$C_4H_9$ | 2,6-$(C_2H_5)_2$-3-Cl | $CH_2$ | $CH_2$ | $CH_2$ | S | |
| 586 | s-$C_4H_9$ | 2,6-$(C_2H_5)_2$-3-Cl | $CH_2$ | $CH_2$ | $CH_2$ | S | |
| 587 | i-$C_4H_9$ | 2,6-$(C_2H_5)_2$-3-Cl | $CH_2$ | $CH_2$ | $CH_2$ | S | |
| 588 | t-$C_4H_9$ | 2,6-$(C_2H_5)_2$-3-Cl | $CH_2$ | $CH_2$ | $CH_2$ | S | |
| 589 | n-$C_5H_{11}$ | 2,6-$(C_2H_5)_2$-3-Cl | $CH_2$ | $CH_2$ | $CH_2$ | S | |
| 590 | neo-$C_5H_{11}$ | 2,6-$(C_2H_5)_2$-3-Cl | $CH_2$ | $CH_2$ | $CH_2$ | S | |
| 591 | c-$C_5H_9$ | 2,6-$(C_2H_5)_2$-3-Cl | $CH_2$ | $CH_2$ | $CH_2$ | S | |
| 592 | t-$C_5H_{11}$ | 2,6-$(C_2H_5)_2$-3-Cl | $CH_2$ | $CH_2$ | $CH_2$ | S | |
| 593 | $C_2H_5$ | 2-$CH_3$-3-Cl | $CH_2$ | $CH_2$ | $CH_2$ | S | |
| 594 | n-$C_3H_7$ | 2-$CH_3$-3-Cl | $CH_2$ | $CH_2$ | $CH_2$ | S | |
| 595 | i-$C_3H_7$ | 2-$CH_3$-3-Cl | $CH_2$ | $CH_2$ | $CH_2$ | S | |
| 596 | c-$C_3H_5$ | 2-$CH_3$-3-Cl | $CH_2$ | $CH_2$ | $CH_2$ | S | |
| 597 | n-$C_4H_9$ | 2-$CH_3$-3-Cl | $CH_2$ | $CH_2$ | $CH_2$ | S | |
| 598 | s-$C_4H_9$ | 2-$CH_3$-3-Cl | $CH_2$ | $CH_2$ | $CH_2$ | S | |
| 599 | i-$C_4H_9$ | 2-$CH_3$-3-Cl | $CH_2$ | $CH_2$ | $CH_2$ | S | |
| 600 | t-$C_4H_9$ | 2-$CH_3$-3-Cl | $CH_2$ | $CH_2$ | $CH_2$ | S | |
| 601 | n-$C_5H_{11}$ | 2-$CH_3$-3-Cl | $CH_2$ | $CH_2$ | $CH_2$ | S | |
| 602 | neo-$C_5H_{11}$ | 2-$CH_3$-3-Cl | $CH_2$ | $CH_2$ | $CH_2$ | S | |
| 603 | c-$C_5H_9$ | 2-$CH_3$-3-Cl | $CH_2$ | $CH_2$ | $CH_2$ | S | |
| 604 | t-$C_5H_{11}$ | 2-$CH_3$-3-Cl | $CH_2$ | $CH_2$ | $CH_2$ | S | |
| 605 | $C_2H_5$ | 2,6-$(C_2H_5)_2$-3-Cl | $CH_2$ | $CH_2$ | SO | $CH_2$ | |
| 606 | n-$C_3H_7$ | 2,6-$(C_2H_5)_2$-3-Cl | $CH_2$ | $CH_2$ | SO | $CH_2$ | 93–100 |
| 607 | i-$C_3H_7$ | 2,6-$(C_2H_5)_2$-3-Cl | $CH_2$ | $CH_2$ | SO | $CH_2$ | |
| 608 | c-$C_3H_5$ | 2,6-$(C_2H_5)_2$-3-Cl | $CH_2$ | $CH_2$ | SO | $CH_2$ | |
| 609 | n-$C_4H_9$ | 2,6-$(C_2H_5)_2$-3-Cl | $CH_2$ | $CH_2$ | SO | $CH_2$ | |
| 610 | s-$C_4H_9$ | 2,6-$(C_2H_5)_2$-3-Cl | $CH_2$ | $CH_2$ | SO | $CH_2$ | |
| 611 | i-$C_4H_9$ | 2,6-$(C_2H_5)_2$-3-Cl | $CH_2$ | $CH_2$ | SO | $CH_2$ | |
| 612 | t-$C_4H_9$ | 2,6-$(C_2H_5)_2$-3-Cl | $CH_2$ | $CH_2$ | SO | $CH_2$ | |
| 613 | n-$C_5H_{11}$ | 2,6-$(C_2H_5)_2$-3-Cl | $CH_2$ | $CH_2$ | SO | $CH_2$ | |
| 614 | neo-$C_5H_{11}$ | 2,6-$(C_2H_5)_2$-3-Cl | $CH_2$ | $CH_2$ | SO | $CH_2$ | |
| 615 | c-$C_5H_9$ | 2,6-$(C_2H_5)_2$-3-Cl | $CH_2$ | $CH_2$ | SO | $CH_2$ | |
| 616 | t-$C_5H_{11}$ | 2,6-$(C_2H_5)_2$-3-Cl | $CH_2$ | $CH_2$ | SO | $CH_2$ | |
| 617 | $C_2H_5$ | 2-$CH_3$-3-Cl | $CH_2$ | $CH_2$ | SO | $CH_2$ | |
| 618 | n-$C_3H_7$ | 2-$CH_3$-3-Cl | $CH_2$ | $CH_2$ | SO | $CH_2$ | |
| 619 | i-$C_3H_7$ | 2-$CH_3$-3-Cl | $CH_2$ | $CH_2$ | SO | $CH_2$ | |
| 620 | c-$C_3H_5$ | 2-$CH_3$-3-Cl | $CH_2$ | $CH_2$ | SO | $CH_2$ | |
| 621 | n-$C_4H_9$ | 2-$CH_3$-3-Cl | $CH_2$ | $CH_2$ | SO | $CH_2$ | |
| 622 | s-$C_4H_9$ | 2-$CH_3$-3-Cl | $CH_2$ | $CH_2$ | SO | $CH_2$ | |
| 623 | i-$C_4H_9$ | 2-$CH_3$-3-Cl | $CH_2$ | $CH_2$ | SO | $CH_2$ | |
| 624 | t-$C_4H_9$ | 2-$CH_3$-3-Cl | $CH_2$ | $CH_2$ | SO | $CH_2$ | |
| 625 | n-$C_5H_{11}$ | 2-$CH_3$-3-Cl | $CH_2$ | $CH_2$ | SO | $CH_2$ | |
| 626 | neo-$C_5H_{11}$ | 2-$CH_3$-3-Cl | $CH_2$ | $CH_2$ | SO | $CH_2$ | |
| 627 | c-$C_5H_9$ | 2-$CH_3$-3-Cl | $CH_2$ | $CH_2$ | SO | $CH_2$ | |
| 628 | t-$C_5H_{11}$ | 2-$CH_3$-3-Cl | $CH_2$ | $CH_2$ | SO | $CH_2$ | |
| 629 | $C_2H_5$ | 2,6-$(C_2H_5)_2$-3-Cl | $CH_2$ | $CH_2$ | $SO_2$ | $CH_2$ | |
| 630 | n-$C_3H_7$ | 2,6-$(C_2H_5)_2$-3-Cl | $CH_2$ | $CH_2$ | $SO_2$ | $CH_2$ | 86–96 |
| 631 | i-$C_3H_7$ | 2,6-$(C_2H_5)_2$-3-Cl | $CH_2$ | $CH_2$ | $SO_2$ | $CH_2$ | |
| 632 | c-$C_3H_5$ | 2,6-$(C_2H_5)_2$-3-Cl | $CH_2$ | $CH_2$ | $SO_2$ | $CH_2$ | |
| 633 | n-$C_4H_9$ | 2,6-$(C_2H_5)_2$-3-Cl | $CH_2$ | $CH_2$ | $SO_2$ | $CH_2$ | |

TABLE 3-continued

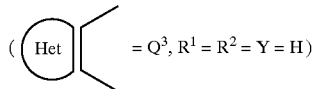 = $Q^3$, $R^1 = R^2 = Y = H$ )

| No | $R^3$ | X | F | G | J | K | mp °C. |
|---|---|---|---|---|---|---|---|
| 634 | s-$C_4H_9$ | 2,6-$(C_2H_5)_2$-3-Cl | $CH_2$ | $CH_2$ | $SO_2$ | $CH_2$ | |
| 635 | i-$C_4H_9$ | 2,6-$(C_2H_5)_2$-3-Cl | $CH_2$ | $CH_2$ | $SO_2$ | $CH_2$ | |
| 636 | t-$C_4H_9$ | 2,6-$(C_2H_5)_2$-3-Cl | $CH_2$ | $CH_2$ | $SO_2$ | $CH_2$ | |
| 637 | n-$C_5H_{11}$ | 2,6-$(C_2H_5)_2$-3-Cl | $CH_2$ | $CH_2$ | $SO_2$ | $CH_2$ | |
| 638 | neo-$C_5H_{11}$ | 2,6-$(C_2H_5)_2$-3-Cl | $CH_2$ | $CH_2$ | $SO_2$ | $CH_2$ | |
| 639 | c-$C_5H_9$ | 2,6-$(C_2H_5)_2$-3-Cl | $CH_2$ | $CH_2$ | $SO_2$ | $CH_2$ | |
| 640 | t-$C_5H_{11}$ | 2,6-$(C_2H_5)_2$-3-Cl | $CH_2$ | $CH_2$ | $SO_2$ | $CH_2$ | |
| 641 | $C_2H_5$ | 2-$CH_3$-3-Cl | $CH_2$ | $CH_2$ | $SO_2$ | $CH_2$ | |
| 642 | n-$C_3H_7$ | 2-$CH_3$-3-Cl | $CH_2$ | $CH_2$ | $SO_2$ | $CH_2$ | |
| 643 | i-$C_3H_7$ | 2-$CH_3$-3-Cl | $CH_2$ | $CH_2$ | $SO_2$ | $CH_2$ | |
| 644 | c-$C_3H_5$ | 2-$CH_3$-3-Cl | $CH_2$ | $CH_2$ | $SO_2$ | $CH_2$ | |
| 645 | n-$C_4H_9$ | 2-$CH_3$-3-Cl | $CH_2$ | $CH_2$ | $SO_2$ | $CH_2$ | |
| 646 | s-$C_4H_9$ | 2-$CH_3$-3-Cl | $CH_2$ | $CH_2$ | $SO_2$ | $CH_2$ | |
| 647 | i-$C_4H_9$ | 2-$CH_3$-3-Cl | $CH_2$ | $CH_2$ | $SO_2$ | $CH_2$ | |
| 648 | t-$C_4H_9$ | 2-$CH_3$-3-Cl | $CH_2$ | $CH_2$ | $SO_2$ | $CH_2$ | |
| 649 | n-$C_5H_{11}$ | 2-$CH_3$-3-Cl | $CH_2$ | $CH_2$ | $SO_2$ | $CH_2$ | |
| 650 | neo-$C_5H_{11}$ | 2-$CH_3$-3-Cl | $CH_2$ | $CH_2$ | $SO_2$ | $CH_2$ | |
| 651 | c-$C_5H_9$ | 2-$CH_3$-3-Cl | $CH_2$ | $CH_2$ | $SO_2$ | $CH_2$ | |
| 652 | t-$C_5H_{11}$ | 2-$CH_3$-3-Cl | $CH_2$ | $CH_2$ | $SO_2$ | $CH_2$ | |
| 653 | $C_2H_5$ | 2,6-$(C_2H_5)_2$-3-Cl | $CH_2$ | $CH_2$ | $NCH_3$ | $CH_2$ | |
| 654 | n-$C_3H_7$ | 2,6-$(C_2H_5)_2$-3-Cl | $CH_2$ | $CH_2$ | $NCH_3$ | $CH_2$ | Refractive index 1.4764 (20° C.) |
| 655 | i-$C_3H_7$ | 2,6-$(C_2H_5)_2$-3-Cl | $CH_2$ | $CH_2$ | $NCH_3$ | $CH_2$ | |
| 656 | c-$C_3H_5$ | 2,6-$(C_2H_5)_2$-3-Cl | $CH_2$ | $CH_2$ | $NCH_3$ | $CH_2$ | |
| 657 | n-$C_4H_9$ | 2,6-$(C_2H_5)_2$-3-Cl | $CH_2$ | $CH_2$ | $NCH_3$ | $CH_2$ | |
| 658 | s-$C_4H_9$ | 2,6-$(C_2H_5)_2$-3-Cl | $CH_2$ | $CH_2$ | $NCH_3$ | $CH_2$ | |
| 659 | i-$C_4H_9$ | 2,6-$(C_2H_5)_2$-3-Cl | $CH_2$ | $CH_2$ | $NCH_3$ | $CH_2$ | |
| 660 | t-$C_4H_9$ | 2,6-$(C_2H_5)_2$-3-Cl | $CH_2$ | $CH_2$ | $NCH_3$ | $CH_2$ | |
| 661 | n-$C_5H_{11}$ | 2,6-$(C_2H_5)_2$-3-Cl | $CH_2$ | $CH_2$ | $NCH_3$ | $CH_2$ | |
| 662 | neo-$C_5H_{11}$ | 2,6-$(C_2H_5)_2$-3-Cl | $CH_2$ | $CH_2$ | $NCH_3$ | $CH_2$ | |
| 663 | c-$C_5H_9$ | 2,6-$(C_2H_5)_2$-3-Cl | $CH_2$ | $CH_2$ | $NCH_3$ | $CH_2$ | |
| 664 | t-$C_5H_{11}$ | 2,6-$(C_2H_5)_2$-3-Cl | $CH_2$ | $CH_2$ | $NCH_3$ | $CH_2$ | |
| 665 | $C_2H_5$ | 2-$CH_3$-3-Cl | $CH_2$ | $CH_2$ | $NCH_3$ | $CH_2$ | |
| 667 | n-$C_3H_7$ | 2-$CH_3$-3-Cl | $CH_2$ | $CH_2$ | $NCH_3$ | $CH_2$ | |
| 668 | i-$C_3H_7$ | 2-$CH_3$-3-Cl | $CH_2$ | $CH_2$ | $NCH_3$ | $CH_2$ | |
| 669 | c-$C_3H_5$ | 2-$CH_3$-3-Cl | $CH_2$ | $CH_2$ | $NCH_3$ | $CH_2$ | |
| 670 | n-$C_4H_9$ | 2-$CH_3$-3-Cl | $CH_2$ | $CH_2$ | $NCH_3$ | $CH_2$ | |
| 671 | s-$C_4H_9$ | 2-$CH_3$-3-Cl | $CH_2$ | $CH_2$ | $NCH_3$ | $CH_2$ | |
| 672 | i-$C_4H_9$ | 2-$CH_3$-3-Cl | $CH_2$ | $CH_2$ | $NCH_3$ | $CH_2$ | |
| 673 | t-$C_4H_9$ | 2-$CH_3$-3-Cl | $CH_2$ | $CH_2$ | $NCH_3$ | $CH_2$ | |
| 674 | n-$C_5H_{11}$ | 2-$CH_3$-3-Cl | $CH_2$ | $CH_2$ | $NCH_3$ | $CH_2$ | |
| 675 | neo-$C_5H_{11}$ | 2-$CH_3$-3-Cl | $CH_2$ | $CH_2$ | $NCH_3$ | $CH_2$ | |
| 676 | c-$C_5H_9$ | 2-$CH_3$-3-Cl | $CH_2$ | $CH_2$ | $NCH_3$ | $CH_2$ | |
| 677 | t-$C_5H_{11}$ | 2-$CH_3$-3-Cl | $CH_2$ | $CH_2$ | $NCH_3$ | $CH_2$ | |
| 678 | $C_2H_5$ | 2,6-$(C_2H_5)_2$-3-Cl | $CH_2$ | $CH_2$ | $CH_2$ | CO | 212–213 |
| 679 | n-$C_3H_7$ | 2,6-$(C_2H_5)_2$-3-Cl | $CH_2$ | $CH_2$ | $CH_2$ | CO | 214–215 |
| 680 | i-$C_3H_7$ | 2,6-$(C_2H_5)_2$-3-Cl | $CH_2$ | $CH_2$ | $CH_2$ | CO | |
| 681 | c-$C_3H_5$ | 2,6-$(C_2H_5)_2$-3-Cl | $CH_2$ | $CH_2$ | $CH_2$ | CO | |
| 682 | n-$C_4H_9$ | 2,6-$(C_2H_5)_2$-3-Cl | $CH_2$ | $CH_2$ | $CH_2$ | CO | |
| 683 | s-$C_4H_9$ | 2,6-$(C_2H_5)_2$-3-Cl | $CH_2$ | $CH_2$ | $CH_2$ | CO | |
| 684 | i-$C_4H_9$ | 2,6-$(C_2H_5)_2$-3-Cl | $CH_2$ | $CH_2$ | $CH_2$ | CO | |
| 685 | t-$C_4H_9$ | 2,6-$(C_2H_5)_2$-3-Cl | $CH_2$ | $CH_2$ | $CH_2$ | CO | |
| 686 | n-$C_5H_{11}$ | 2,6-$(C_2H_5)_2$-3-Cl | $CH_2$ | $CH_2$ | $CH_2$ | CC | |
| 687 | neo-$C_5H_{11}$ | 2,6-$(C_2H_5)_2$-3-Cl | $CH_2$ | $CH_2$ | $CH_2$ | CO | |
| 688 | c-$C_5H_9$ | 2,6-$(C_2H_5)_2$-3-Cl | $CH_2$ | $CH_2$ | $CH_2$ | CO | |
| 689 | t-$C_5H_{11}$ | 2,6-$(C_2H_5)_2$-3-Cl | $CH_2$ | $CH_2$ | $CH_2$ | CO | |
| 690 | $C_2H_5$ | 2-$CH_3$-3-Cl | $CH_2$ | $CH_2$ | $CH_2$ | CO | |
| 691 | n-$C_3H_7$ | 2-$CH_3$-3-Cl | $CH_2$ | $CH_2$ | $CH_2$ | CO | |
| 692 | i-$C_3H_7$ | 2-$CH_3$-3-Cl | $CH_2$ | $CH_2$ | $CH_2$ | CO | |
| 693 | c-$C_3H_5$ | 2-$CH_3$-3-Cl | $CH_2$ | $CH_2$ | $CH_2$ | CO | |
| 694 | n-$C_4H_9$ | 2-$CH_3$-3-Cl | $CH_2$ | $CH_2$ | $CH_2$ | CO | |
| 695 | s-$C_4H_9$ | 2-$CH_3$-3-Cl | $CH_2$ | $CH_2$ | $CH_2$ | CO | |
| 696 | i-$C_4H_9$ | 2-$CH_3$-3-Cl | $CH_2$ | $CH_2$ | $CH_2$ | CO | |
| 697 | t-$C_4H_9$ | 2-$CH_3$-3-Cl | $CH_2$ | $CH_2$ | $CH_2$ | CO | |
| 698 | n-$C_5H_{11}$ | 2-$CH_3$-3-Cl | $CH_2$ | $CH_2$ | $CH_2$ | CO | |
| 699 | neo-$C_5H_{11}$ | 2-$CH_3$-3-Cl | $CH_2$ | $CH_2$ | $CH_2$ | CO | |
| 700 | c-$C_5H_9$ | 2-$CH_3$-3-Cl | $CH_2$ | $CH_2$ | $CH_2$ | CO | |
| 701 | t-$C_5H_{11}$ | 2-$CH_3$-3-Cl | $CH_2$ | $CH_2$ | $CH_2$ | CO | |
| 702 | $C_2H_5$ | 2,6-$(C_2H_5)_2$-3-Cl | O | $CH_2$ | $CH_2$ | CO | |

TABLE 3-continued

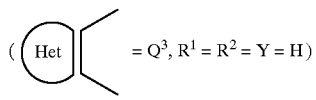
( Het = $Q^3$, $R^1 = R^2 = Y = H$ )

| No | $R^3$ | X | F | G | J | K | mp ° C. |
|---|---|---|---|---|---|---|---|
| 703 | n-$C_3H_7$ | 2,6-$(C_2H_5)_2$-3-Cl | O | $CH_2$ | $CH_2$ | CO | 185–188 |
| 704 | i-$C_3H_7$ | 2,6-$(C_2H_5)_2$-3-Cl | O | $CH_2$ | $CH_2$ | CO | |
| 705 | c-$C_3H_5$ | 2,6-$(C_2H_5)_2$-3-Cl | O | $CH_2$ | $CH_2$ | CO | |
| 706 | n-$C_4H_9$ | 2,6-$(C_2H_5)_2$-3-Cl | O | $CH_2$ | $CH_2$ | CO | |
| 707 | s-$C_4H_9$ | 2,6-$(C_2H_5)_2$-3-Cl | O | $CH_2$ | $CH_2$ | CO | |
| 708 | i-$C_4H_9$ | 2,6-$(C_2H_5)_2$-3-Cl | O | $CH_2$ | $CH_2$ | CO | |
| 709 | t-$C_4H_9$ | 2,6-$(C_2H_5)_2$-3-Cl | O | $CH_2$ | $CH_2$ | CO | |
| 710 | n-$C_5H_{11}$ | 2,6-$(C_2H_5)_2$-3-Cl | O | $CH_2$ | $CH_2$ | CO | |
| 711 | neo-$C_5H_{11}$ | 2,6-$(C_2H_5)_2$-3-Cl | O | $CH_2$ | $CH_2$ | CO | |
| 712 | c-$C_5H_9$ | 2,6-$(C_2H_5)_2$-3-Cl | O | $CH_2$ | $CH_2$ | CO | |
| 713 | t-$C_5H_{11}$ | 2,6-$(C_2H_5)_2$-3-Cl | O | $CH_2$ | $CH_2$ | CO | |
| 714 | $C_2H_5$ | 2-$CH_3$-3-Cl | O | $CH_2$ | $CH_2$ | CO | |
| 715 | n-$C_3H_7$ | 2-$CH_3$-3-Cl | O | $CH_2$ | $CH_2$ | CO | |
| 716 | i-$C_3H_7$ | 2-$CH_3$-3-Cl | O | $CH_2$ | $CH_2$ | CO | |
| 717 | c-$C_3H_5$ | 2-$CH_3$-3-Cl | O | $CH_2$ | $CH_2$ | CO | |
| 718 | n-$C_4H_9$ | 2-$CH_3$-3-Cl | O | $CH_2$ | $CH_2$ | CO | |
| 719 | s-$C_4H_9$ | 2-$CH_3$-3-Cl | O | $CH_2$ | $CH_2$ | CO | |
| 720 | i-$C_4H_9$ | 2-$CH_3$-3-Cl | O | $CH_2$ | $CH_2$ | CO | |
| 721 | t-$C_4H_9$ | 2-$CH_3$-3-Cl | O | $CH_2$ | $CH_2$ | CO | |
| 722 | n-$C_5H_{11}$ | 2-$CH_3$-3-Cl | O | $CH_2$ | $CH_2$ | CO | |
| 723 | neo-$C_5H_{11}$ | 2-$CH_3$-3-Cl | O | $CH_2$ | $CH_2$ | CO | |
| 724 | c-$C_5H_9$ | 2-$CH_3$-3-Cl | O | $CH_2$ | $CH_2$ | CO | 189–192 |
| 725 | t-$C_5H_{11}$ | 2-$CH_3$-3-Cl | O | $CH_2$ | $CH_2$ | CO | |
| 726 | $C_2H_5$ | 2,6-$(C_2H_5)_2$-3-Cl | O | CH=CH | | CO | |
| 727 | n-$C_3H_7$ | 2,6-$(C_2H_5)_2$-3-Cl | O | CH=CH | | CO | 198–201 |
| 728 | i-$C_3H_7$ | 2,6-$(C_2H_5)_2$-3-Cl | O | CH=CH | | CO | |
| 729 | c-$C_3H_5$ | 2,6-$(C_2H_5)_2$-3-Cl | O | CH=CH | | CO | |
| 730 | n-$C_4H_9$ | 2,6-$(C_2H_5)_2$-3-Cl | O | CH=CH | | CO | |
| 731 | s-$C_4H_9$ | 2,6-$(C_2H_5)_2$-3-Cl | O | CH=CH | | CO | |
| 732 | i-$C_4H_9$ | 2,6-$(C_2H_5)_2$-3-Cl | O | CH=CH | | CO | |
| 733 | t-$C_4H_9$ | 2,6-$(C_2H_5)_2$-3-Cl | O | CH=CH | | CO | |
| 734 | n-$C_5H_{11}$ | 2,6-$(C_2H_5)_2$-3-Cl | O | CH=CH | | CO | |
| 735 | neo-$C_5H_{11}$ | 2,6-$(C_2H_5)_2$-3-Cl | O | CH=CH | | CO | |
| 736 | c-$C_5H_9$ | 2,6-$(C_2H_5)_2$-3-Cl | O | CH=CH | | CO | |
| 737 | t-$C_5H_{11}$ | 2,6-$(C_2H_5)_2$-3-Cl | O | CH=CH | | CO | |
| 738 | $C_2H_5$ | 2,6-$(C_2H_5)_2$-3-Cl | O | $CH_2$ | $CH_2$ | O | |
| 739 | n-$C_3H_7$ | 2,6-$(C_2H_5)_2$-3-Cl | O | $CH_2$ | $CH_2$ | O | 173–175 |
| 740 | i-$C_3H_7$ | 2,6-$(C_2H_5)_2$-3-Cl | O | $CH_2$ | $CH_2$ | O | |
| 741 | c-$C_3H_5$ | 2,6-$(C_2H_5)_2$-3-Cl | O | $CH_2$ | $CH_2$ | O | |
| 742 | n-$C_4H_9$ | 2,6-$(C_2H_5)_2$-3-Cl | O | $CH_2$ | $CH_2$ | O | |
| 743 | s-$C_4H_9$ | 2,6-$(C_2H_5)_2$-3-Cl | O | $CH_2$ | $CH_2$ | O | |
| 744 | i-$C_4H_9$ | 2,6-$(C_2H_5)_2$-3-Cl | O | $CH_2$ | $CH_2$ | O | |
| 745 | t-$C_4H_9$ | 2,6-$(C_2H_5)_2$-3-Cl | O | $CH_2$ | $CH_2$ | O | |
| 746 | n-$C_5H_{11}$ | 2,6-$(C_2H_5)_2$-3-Cl | O | $CH_2$ | $CH_2$ | O | |
| 747 | neo-$C_5H_{11}$ | 2,6-$(C_2H_5)_2$-3-Cl | O | $CH_2$ | $CH_2$ | O | |
| 748 | c-$C_5H_9$ | 2,6-$(C_2H_5)_2$-3-Cl | O | $CH_2$ | $CH_2$ | O | |
| 749 | t-$C_5H_{11}$ | 2,6-$(C_2H_5)_2$-3-Cl | O | $CH_2$ | $CH_2$ | O | |
| 750 | $C_2H_5$ | 2-$CH_3$-3-Cl | O | $CH_2$ | $CH_2$ | O | |
| 751 | n-$C_3H_7$ | 2-$CH_3$-3-Cl | O | $CH_2$ | $CH_2$ | O | |
| 752 | i-$C_3H_7$ | 2-$CH_3$-3-Cl | O | $CH_2$ | $CH_2$ | O | |
| 753 | c-$C_3H_5$ | 2-$CH_3$-3-Cl | O | $CH_2$ | $CH_2$ | O | |
| 754 | n-$C_4H_9$ | 2-$CH_3$-3-Cl | O | $CH_2$ | $CH_2$ | O | |
| 755 | s-$C_4H_9$ | 2-$CH_3$-3-Cl | O | $CH_2$ | $CH_2$ | O | |
| 756 | i-$C_4H_9$ | 2-$CH_3$-3-Cl | O | $CH_2$ | $CH_2$ | O | |
| 757 | t-$C_4H_9$ | 2-$CH_3$-3-Cl | O | $CH_2$ | $CH_2$ | O | |
| 758 | n-$C_5H_{11}$ | 2-$CH_3$-3-Cl | O | $CH_2$ | $CH_2$ | O | |
| 759 | neo-$C_5H_{11}$ | 2-$CH_3$-3-Cl | O | $CH_2$ | $CH_2$ | O | |
| 760 | c-$C_5H_9$ | 2-$CH_3$-3-Cl | O | $CH_2$ | $CH_2$ | O | 179–182 |
| 761 | t-$C_5H_{11}$ | 2-$CH_3$-3-Cl | O | $CH_2$ | $CH_2$ | O | |
| 762 | $C_2H_5$ | 2,6-$(C_2H_5)_2$-3-Cl | O | $CH_2$ | $CH_2$ | $NCH_3$ | |
| 763 | n-$C_3H_7$ | 2,6-$(C_2H_5)_2$-3-Cl | O | $CH_2$ | $CH_2$ | $NCH_3$ | 153–155 |
| 764 | i-$C_3H_7$ | 2,6-$(C_2H_5)_2$-3-Cl | O | $CH_2$ | $CH_2$ | $NCH_3$ | |
| 765 | c-$C_3H_5$ | 2,6-$(C_2H_5)_2$-3-Cl | O | $CH_2$ | $CH_2$ | $NCH_3$ | |
| 766 | n-$C_4H_9$ | 2,6-$(C_2H_5)_2$-3-Cl | O | $CH_2$ | $CH_2$ | $NCH_3$ | |
| 767 | s-$C_4H_9$ | 2,6-$(C_2H_5)_2$-3-Cl | O | $CH_2$ | $CH_2$ | $NCH_3$ | |
| 768 | i-$C_4H_9$ | 2,6-$(C_2H_5)_2$-3-Cl | O | $CH_2$ | $CH_2$ | $NCH_3$ | |
| 769 | t-$C_4H_9$ | 2,6-$(C_2H_5)_2$-3-Cl | O | $CH_2$ | $CH_2$ | $NCH_3$ | |

TABLE 3-continued

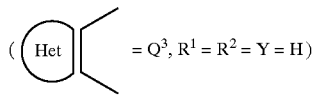
$(\text{Het} = Q^3, R^1 = R^2 = Y = H)$

| No | R³ | X | F | G | J | K | mp °C. |
|---|---|---|---|---|---|---|---|
| 770 | n-C₅H₁₁ | 2,6-(C₂H₅)₂-3-Cl | O | CH₂ | CH₂ | NCH₃ | |
| 771 | neo-C₅H₁₁ | 2,6-(C₂H₅)₂-3-Cl | O | CH₂ | CH₂ | NCH₃ | |
| 772 | c-C₅H₉ | 2,6-(C₂H₅)₂-3-Cl | O | CH₂ | CH₂ | NCH₃ | |
| 773 | t-C₅H₁₁ | 2,6-(C₂H₅)₂-3-Cl | O | CH₂ | CH₂ | NCH₃ | |

TABLE 4

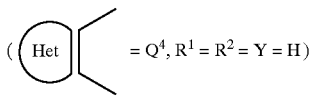
$(\text{Het} = Q^4, R^1 = R^2 = Y = H)$

| No | R³ | X | (R⁹)ₘ | Z | mp °C. |
|---|---|---|---|---|---|
| 774 | C₂H₅ | 2,6-(C₂H₅)₂-3-Cl | H | O | 226–229 |
| 775 | n-C₃H₇ | 2,6-(C₂H₅)₂-3-Cl | H | O | 192–193 |
| 776 | i-C₃H₇ | 2,6-(C₂H₅)₂-3-Cl | H | O | |
| 777 | c-C₃H₅ | 2,6-(C₂H₅)₂-3-Cl | H | O | |
| 778 | n-C₄H₉ | 2,6-(C₂H₅)₂-3-Cl | H | O | |
| 779 | s-C₄H₉ | 2,6-(C₂H₅)₂-3-Cl | H | O | |
| 780 | i-C₄H₉ | 2,6-(C₂H₅)₂-3-Cl | H | O | |
| 781 | t-C₄H₉ | 2,6-(C₂H₅)₂-3-Cl | H | O | |
| 782 | n-C₅H₁₁ | 2,6-(C₂H₅)₂-3-Cl | H | O | |
| 783 | neo-C₅H₁₁ | 2,6-(C₂H₅)₂-3-Cl | H | O | |
| 784 | c-C₅H₉ | 2,6-(C₂H₅)₂-3-Cl | H | O | |
| 785 | t-C₅H₁₁ | 2,6-(C₂H₅)₂-3-Cl | H | O | |
| 786 | C₂H₅ | 2-CH₃-3-Cl | H | O | |
| 787 | n-C₃H₇ | 2-CH₃-3-Cl | H | O | |
| 788 | i-C₃H₇ | 2-CH₃-3-Cl | H | O | |
| 789 | c-C₃H₅ | 2-CH₃-3-Cl | H | O | |
| 790 | n-C₄H₉ | 2-CH₃-3-Cl | H | O | |
| 791 | s-C₄H₉ | 2-CH₃-3-Cl | H | O | |
| 792 | i-C₄H₉ | 2-CH₃-3-Cl | H | O | |
| 793 | t-C₄H₉ | 2-CH₃-3-Cl | H | O | |
| 794 | n-C₅H₁₁ | 2-CH₃-3-Cl | H | O | |
| 795 | neo-C₅H₁₁ | 2-CH₃-3-Cl | H | O | |
| 796 | c-C₅H₉ | 2-CH₃-3-Cl | H | O | 198–200 |
| 797 | t-C₅H₁₁ | 2-CH₃-3-Cl | H | O | |
| 798 | C₂H₅ | 2,6-(C₂H₅)₂-3-Cl | H | S | 225–229 |
| 799 | n-C₃H₇ | 2,6-(C₂H₅)₂-3-Cl | H | S | 194–196 |
| 800 | i-C₃H₇ | 2,6-(C₂H₅)₂-3-Cl | H | S | |
| 801 | c-C₃H₅ | 2,6-(C₂H₅)₂-3-Cl | H | S | |
| 802 | n-C₄H₉ | 2,6-(C₂H₅)₂-3-Cl | H | S | |
| 803 | s-C₄H₉ | 2,6-(C₂H₅)₂-3-Cl | H | S | |
| 804 | i-C₄H₉ | 2,6-(C₂H₅)₂-3-Cl | H | S | |
| 805 | t-C₄H₉ | 2,6-(C₂H₅)₂-3-Cl | H | S | |
| 806 | n-C₅H₁₁ | 2,6-(C₂H₅)₂-3-Cl | H | S | |
| 807 | neo-C₅H₁₁ | 2,6-(C₂H₅)₂-3-Cl | H | S | |
| 808 | c-C₅H₉ | 2,6-(C₂H₅)₂-3-Cl | H | S | |
| 809 | t-C₅H₁₁ | 2,6-(C₂H₅)₂-3-Cl | H | S | |
| 810 | neo-C₅H₁₁ | 2-CH₃-3-Cl | H | S | |
| 811 | c-C₅H₉ | 2-CH₃-3-Cl | H | S | 197–199 |
| 812 | t-C₅H₁₁ | 2-CH₃-3-Cl | H | S | |
| 813 | C₂H₅ | 2,6-(C₂H₅)₂-3-Cl | 3-Br | S | |
| 814 | n-C₃H₇ | 2,6-(C₂H₅)₂-3-Cl | 3-Br | S | 187–190 |
| 815 | i-C₃H₇ | 2,6-(C₂H₅)₂-3-Cl | 3-Br | S | |
| 816 | c-C₃H₅ | 2,6-(C₂H₅)₂-3-Cl | 3-Br | S | |
| 817 | n-C₄H₉ | 2,6-(C₂H₅)₂-3-Cl | 3-Br | S | |
| 818 | s-C₄H₉ | 2,6-(C₂H₅)₂-3-Cl | 3-Br | S | |
| 819 | i-C₄H₉ | 2,6-(C₂H₅)₂-3-Cl | 3-Br | S | |
| 820 | t-C₄H₉ | 2,6-(C₂H₅)₂-3-Cl | 3-Br | S | |
| 821 | neo-C₅H₁₁ | 2,6-(C₂H₅)₂-3-Cl | 3-Br | S | |
| 822 | c-C₅H₉ | 2,6-(C₂H₅)₂-3-Cl | 3-Br | S | |
| 823 | C₂H₅ | 2,6-(C₂H₅)₂-3-Cl | H | NCH₃ | |
| 824 | n-C₃H₇ | 2,6-(C₂H₅)₂-3-Cl | H | NCH₃ | 166–169 |
| 825 | i-C₃H₇ | 2,6-(C₂H₅)₂-3-Cl | H | NCH₃ | |
| 826 | c-C₃H₅ | 2,6-(C₂H₅)₂-3-Cl | H | NCH₃ | |

TABLE 4-continued

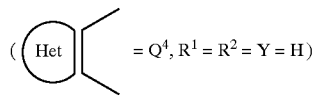
$(\text{Het} = Q^4, R^1 = R^2 = Y = H)$

| No | R³ | X | (R⁹)ₘ | Z | mp °C. |
|---|---|---|---|---|---|
| 827 | n-C₄H₉ | 2,6-(C₂H₅)₂-3-Cl | H | NCH₃ | |
| 828 | s-C₄H₉ | 2,6-(C₂H₅)₂-3-Cl | H | NCH₃ | |
| 829 | i-C₄H₉ | 2,6-(C₂H₅)₂-3-Cl | H | NCH₃ | |
| 830 | t-C₄H₉ | 2,6-(C₂H₅)₂-3-Cl | H | NCH₃ | |
| 831 | n-C₅H₁₁ | 2,6-(C₂H₅)₂-3-Cl | H | NCH₃ | |
| 832 | neo-C₅H₁₁ | 2,6-(C₂H₅)₂-3-Cl | H | NCH₃ | |
| 833 | c-C₅H₉ | 2,6-(C₂H₅)₂-3-Cl | H | NCH₃ | |
| 834 | t-C₅H₁₁ | 2,6-(C₂H₅)₂-3-Cl | H | NCH₃ | |

TABLE 5

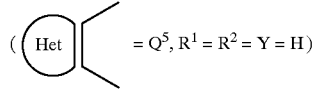
$(\text{Het} = Q^5, R^1 = R^2 = Y = H)$

| No | R³ | X | (R⁹)ₘ | Z | mp °C. |
|---|---|---|---|---|---|
| 835 | C₂H₅ | 2,6-(C₂H₅)₂-3-Cl | H | S | |
| 836 | n-C₃H₇ | 2,6-(C₂H₅)₂-3-Cl | H | S | 198–201 |
| 837 | i-C₃H₇ | 2,6-(C₂H₅)₂-3-Cl | H | S | |
| 838 | c-C₃H₅ | 2,6-(C₂H₅)₂-3-Cl | H | S | |
| 839 | n-C₄H₉ | 2,6-(C₂H₅)₂-3-Cl | H | S | |
| 840 | s-C₄H₉ | 2,6-(C₂H₅)₂-3-Cl | H | S | |
| 841 | i-C₄H₉ | 2,6-(C₂H₅)₂-3-Cl | H | S | |
| 842 | t-C₄H₉ | 2,6-(C₂H₅)₂-3-Cl | H | S | |
| 843 | n-C₅H₁₁ | 2,6-(C₂H₅)₂-3-Cl | H | S | |
| 844 | neo-C₅H₁₁ | 2,6-(C₂H₅)₂-3-Cl | H | S | |
| 845 | c-C₅H₉ | 2,6-(C₂H₅)₂-3-Cl | H | S | |

TABLE 6

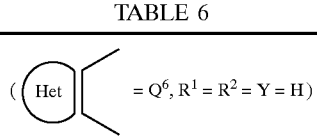
$(\text{Het} = Q^6, R^1 = R^2 = Y = H)$

| No | R³ | X | (R⁹)ₘ | Z | mp °C. |
|---|---|---|---|---|---|
| 846 | C₂H₅ | 2,6-(C₂H₅)₂-3-Cl | H | O | |
| 847 | n-C₃H₇ | 2,6-(C₂H₅)₂-3-Cl | H | O | 198–201 |
| 848 | i-C₃H₇ | 2,6-(C₂H₅)₂-3-Cl | H | O | |
| 849 | c-C₃H₅ | 2,6-(C₂H₅)₂-3-Cl | H | O | |
| 850 | n-C₄H₉ | 2,6-(C₂H₅)₂-3-Cl | H | O | |
| 851 | s-C₄H₉ | 2,6-(C₂H₅)₂-3-Cl | H | O | |
| 852 | i-C₄H₉ | 2,6-(C₂H₅)₂-3-Cl | H | O | |
| 853 | t-C₄H₉ | 2,6-(C₂H₅)₂-3-Cl | H | O | |
| 854 | n-C₅H₁₁ | 2,6-(C₂H₅)₂-3-Cl | H | O | |

TABLE 6-continued ( Het ) = $Q^6$, $R^1 = R^2 = Y = H$

| No | $R^3$ | X | $(R^9)_m$ | Z | mp °C. |
|---|---|---|---|---|---|
| 855 | neo-$C_5H_{11}$ | 2,6-$(C_2H_5)_2$-3-Cl | H | O | |
| 856 | c-$C_5H_9$ | 2,6-$(C_2H_5)_2$-3-Cl | H | O | |
| 857 | t-$C_5H_{11}$ | 2,6-$(C_2H_5)_2$-3-Cl | H | O | |
| 858 | $C_2H_5$ | 2-$CH_3$-3-Cl | H | O | |
| 859 | n-$C_3H_7$ | 2-$CH_3$-3-Cl | H | O | |
| 860 | i-$C_3H_7$ | 2-$CH_3$-3-Cl | H | O | |
| 861 | c-$C_3H_5$ | 2-$CH_3$-3-Cl | H | O | |
| 862 | n-$C_4H_9$ | 2-$CH_3$-3-Cl | H | O | |
| 863 | s-$C_4H_9$ | 2-$CH_3$-3-Cl | H | O | |
| 864 | i-$C_4H_9$ | 2-$CH_3$-3-Cl | H | O | |
| 865 | t-$C_4H_9$ | 2-$CH_3$-3-Cl | H | O | |
| 866 | n-$C_5H_{11}$ | 2-$CH_3$-3-Cl | H | O | |
| 867 | neo-$C_5H_{11}$ | 2-$CH_3$-3-Cl | H | O | |
| 868 | c-$C_5H_9$ | 2-$CH_3$-3-Cl | H | O | |
| 869 | t-$C_5H_{11}$ | 2-$CH_3$-3-Cl | H | O | |
| 870 | $C_2H_5$ | 2,6-$(C_2H_5)_2$-3-Cl | H | S | 213–214 |
| 871 | n-$C_3H_7$ | 2,6-$(C_2H_5)_2$-3-Cl | H | S | 200–202 |
| 872 | i-$C_3H_7$ | 2,6-$(C_2H_5)_2$-3-Cl | H | S | |
| 873 | c-$C_3H_5$ | 2,6-$(C_2H_5)_2$-3-Cl | H | S | |
| 874 | n-$C_4H_9$ | 2,6-$(C_2H_5)_2$-3-Cl | H | S | |
| 875 | s-$C_4H_9$ | 2,6-$(C_2H_5)_2$-3-Cl | H | S | |
| 876 | i-$C_4H_9$ | 2,6-$(C_2H_5)_2$-3-Cl | H | S | |
| 877 | t-$C_4H_9$ | 2,6-$(C_2H_5)_2$-3-Cl | H | S | |
| 878 | n-$C_5H_{11}$ | 2,6-$(C_2H_5)_2$-3-Cl | H | S | |
| 879 | neo-$C_5H_{11}$ | 2,6-$(C_2H_5)_2$-3-Cl | H | S | |
| 880 | c-$C_5H_9$ | 2,6-$(C_2H_5)_2$-3-Cl | H | S | |
| 881 | t-$C_5H_{11}$ | 2,6-$(C_2H_5)_2$-3-Cl | H | S | |
| 882 | $C_2H_5$ | 2-$CH_3$-3-Cl | H | S | |
| 883 | n-$C_3H_7$ | 2-$CH_3$-3-Cl | H | S | |
| 884 | i-$C_3H_7$ | 2-$CH_3$-3-Cl | H | S | |
| 885 | c-$C_3H_5$ | 2-$CH_3$-3-Cl | H | S | |
| 886 | n-$C_4H_9$ | 2-$CH_3$-3-Cl | H | S | |
| 887 | s-$C_4H_9$ | 2-$CH_3$-3-Cl | H | S | |
| 888 | i-$C_4H_9$ | 2-$CH_3$-3-Cl | H | S | |
| 889 | t-$C_4H_9$ | 2-$CH_3$-3-Cl | H | S | |
| 890 | n-$C_5H_{11}$ | 2-$CH_3$-3-Cl | H | S | |
| 891 | neo-$C_5H_{11}$ | 2-$CH_3$-3-Cl | H | S | |
| 892 | c-$C_5H_9$ | 2-$CH_3$-3-Cl | H | S | 206–208 |
| 893 | t-$C_5H_{11}$ | 2-$CH_3$-3-Cl | H | S | |
| 894 | $C_2H_5$ | 2,6-$(C_2H_5)_2$-3-Cl | H | $NOCH_3$ | 151–153 |
| 895 | n-$C_3H_7$ | 2,6-$(C_2H_5)_2$-3-Cl | H | $NOCH_3$ | 171–173 |
| 896 | i-$C_3H_7$ | 2,6-$(C_2H_5)_2$-3-Cl | H | $NOCH_3$ | |
| 897 | c-$C_3H_5$ | 2,6-$(C_2H_5)_2$-3-Cl | H | $NOCH_3$ | |
| 898 | n-$C_4H_9$ | 2,6-$(C_2H_5)_2$-3-Cl | H | $NOCH_3$ | |
| 899 | s-$C_4H_9$ | 2,6-$(C_2H_5)_2$-3-Cl | H | $NOCH_3$ | |
| 900 | i-$C_4H_9$ | 2,6-$(C_2H_5)_2$-3-Cl | H | $NOCH_3$ | |
| 901 | t-$C_4H_9$ | 2,6-$(C_2H_5)_2$-3-Cl | H | $NOCH_3$ | |
| 902 | n-$C_5H_{11}$ | 2,6-$(C_2H_5)_2$-3-Cl | H | $NOCH_3$ | |
| 903 | neo-$C_5H_{11}$ | 2,6-$(C_2H_5)_2$-3-Cl | H | $NOCH_3$ | |
| 904 | c-$C_5H_9$ | 2,6-$(C_2H_5)_2$-3-Cl | H | $NOCH_3$ | |
| 905 | t-$C_5H_{11}$ | 2,6-$(C_2H_5)_2$-3-Cl | H | $NOCH_3$ | |
| 906 | $C_2H_5$ | 2,6-$(C_2H_5)_2$-3-Cl | H | $NCH_3$ | |
| 907 | n-$C_3H_7$ | 2,6-$(C_2H_5)_2$-3-Cl | H | $NCH_3$ | 151–153 |
| 908 | i-$C_3H_7$ | 2,6-$(C_2H_5)_2$-3-Cl | H | $NCH_3$ | |
| 909 | c-$C_3H_5$ | 2,6-$(C_2H_5)_2$-3-Cl | H | $NCH_3$ | |
| 910 | n-$C_4H_9$ | 2,6-$(C_2H_5)_2$-3-Cl | H | $NCH_3$ | |
| 911 | s-$C_4H_9$ | 2,6-$(C_2H_5)_2$-3-Cl | H | $NCH_3$ | |
| 912 | i-$C_4H_9$ | 2,6-$(C_2H_5)_2$-3-Cl | H | $NCH_3$ | |
| 913 | t-$C_4H_9$ | 2,6-$(C_2H_5)_2$-3-Cl | H | $NCH_3$ | |
| 914 | n-$C_5H_{11}$ | 2,6-$(C_2H_5)_2$-3-Cl | H | $NCH_3$ | |
| 915 | neo-$C_5H_{11}$ | 2,6-$(C_2H_5)_2$-3-Cl | H | $NCH_3$ | |
| 916 | c-$C_5H_9$ | 2,6-$(C_2H_5)_2$-3-Cl | H | $NCH_3$ | |
| 917 | t-$C_5H_{11}$ | 2,6-$(C_2H_5)_2$-3-Cl | H | $NCH_3$ | |

TABLE 7

( Het ) = $Q^7$, $R^1 = R^2 = Y = H$

| No | $R^3$ | X | L | M | T | mp °C. |
|---|---|---|---|---|---|---|
| 918 | $C_2H_5$ | 2,6-$(C_2H_5)_2$-3-Cl | O | $CH_2$ | $CH_2$ | |
| 919 | n-$C_3H_7$ | 2,6-$(C_2H_5)_2$-3-Cl | O | $CH_2$ | $CH_2$ | 177–180 |
| 920 | i-$C_3H_7$ | 2,6-$(C_2H_5)_2$-3-Cl | O | $CH_2$ | $CH_2$ | |
| 921 | c-$C_3H_5$ | 2,6-$(C_2H_5)_2$-3-Cl | O | $CH_2$ | $CH_2$ | |
| 922 | n-$C_4H_9$ | 2,6-$(C_2H_5)_2$-3-Cl | O | $CH_2$ | $CH_2$ | |
| 923 | s-$C_4H_9$ | 2,6-$(C_2H_5)_2$-3-Cl | O | $CH_2$ | $CH_2$ | |
| 924 | i-$C_4H_9$ | 2,6-$(C_2H_5)_2$-3-Cl | O | $CH_2$ | $CH_2$ | |
| 925 | t-$C_4H_9$ | 2,6-$(C_2H_5)_2$-3-Cl | O | $CH_2$ | $CH_2$ | |
| 926 | n-$C_5H_{11}$ | 2,6-$(C_2H_5)_2$-3-Cl | O | $CH_2$ | $CH_2$ | |
| 927 | neo-$C_5H_{11}$ | 2,6-$(C_2H_5)_2$-3-Cl | O | $CH_2$ | $CH_2$ | |
| 928 | c-$C_5H_9$ | 2,6-$(C_2H_5)_2$-3-Cl | O | $CH_2$ | $CH_2$ | |
| 929 | t-$C_5H_{11}$ | 2,6-$(C_2H_5)_2$-3-Cl | O | $CH_2$ | $CH_2$ | |
| 930 | neo-$C_5H_{11}$ | 2-$CH_3$-3-Cl | O | $CH_2$ | $CH_2$ | |
| 931 | c-$C_5H_9$ | 2-$CH_3$-3-Cl | O | $CH_2$ | $CH_2$ | |
| 932 | t-$C_5H_{11}$ | 2-$CH_3$-3-Cl | O | $CH_2$ | $CH_2$ | |
| 933 | $C_2H_5$ | 2,6-$(C_2H_5)_2$-3-Cl | $CH_2$ | O | $CH_2$ | |
| 934 | n-$C_3H_7$ | 2,6-$(C_2H_5)_2$-3-Cl | $CH_2$ | O | $CH_2$ | 179–181 |
| 935 | i-$C_3H_7$ | 2,6-$(C_2H_5)_2$-3-Cl | $CH_2$ | O | $CH_2$ | |
| 936 | c-$C_3H_5$ | 2,6-$(C_2H_5)_2$-3-Cl | $CH_2$ | O | $CH_2$ | |
| 937 | n-$C_4H_9$ | 2,6-$(C_2H_5)_2$-3-Cl | $CH_2$ | O | $CH_2$ | |
| 938 | s-$C_4H_9$ | 2,6-$(C_2H_5)_2$-3-Cl | $CH_2$ | O | $CH_2$ | |
| 939 | i-$C_4H_9$ | 2,6-$(C_2H_5)_2$-3-Cl | $CH_2$ | O | $CH_2$ | |
| 940 | neo-$C_5H_{11}$ | 2,6-$(C_2H_5)_2$-3-Cl | $CH_2$ | O | $CH_2$ | |
| 941 | c-$C_5H_9$ | 2,6-$(C_2H_5)_2$-3-Cl | $CH_2$ | O | $CH_2$ | |
| 942 | $C_2H_5$ | 2,6-$(C_2H_5)_2$-3-Cl | O | $CH_2$ | $CHOCH_3$ | |
| 943 | n-$C_3H_7$ | 2,6-$(C_2H_5)_2$-3-Cl | O | $CH_2$ | $CHOCH_3$ | 163–165 |
| 944 | i-$C_3H_7$ | 2,6-$(C_2H_5)_2$-3-Cl | O | $CH_2$ | $CHOCH_3$ | |
| 945 | c-$C_3H_5$ | 2,6-$(C_2H_5)_2$-3-Cl | O | $CH_2$ | $CHOCH_3$ | |
| 946 | n-$C_4H_9$ | 2,6-$(C_2H_5)_2$-3-Cl | O | $CH_2$ | $CHOCH_3$ | |
| 947 | s-$C_4H_9$ | 2,6-$(C_2H_5)_2$-3-Cl | O | $CH_2$ | $CHOCH_3$ | |
| 948 | i-$C_4H_9$ | 2,6-$(C_2H_5)_2$-3-Cl | O | $CH_2$ | $CHOCH_3$ | |
| 949 | t-$C_4H_9$ | 2,6-$(C_2H_5)_2$-3-Cl | O | $CH_2$ | $CHOCH_3$ | |
| 950 | n-$C_5H_{11}$ | 2,6-$(C_2H_5)_2$-3-Cl | O | $CH_2$ | $CHOCH_3$ | |
| 951 | neo-$C_5H_{11}$ | 2,6-$(C_2H_5)_2$-3-Cl | O | $CH_2$ | $CHOCH_3$ | |
| 952 | c-$C_5H_9$ | 2,6-$(C_2H_5)_2$-3-Cl | O | $CH_2$ | $CHOCH_3$ | |
| 953 | t-$C_5H_{11}$ | 2,6-$(C_2H_5)_2$-3-Cl | O | $CH_2$ | $CHOCH_3$ | |
| 954 | $C_2H_5$ | 2,6-$(C_2H_5)_2$-3-Cl | S | $CH_2$ | $CH_2$ | |
| 955 | n-$C_3H_7$ | 2,6-$(C_2H_5)_2$-3-Cl | S | $CH_2$ | $CH_2$ | 167–171 |
| 956 | i-$C_3H_7$ | 2,6-$(C_2H_5)_2$-3-Cl | S | $CH_2$ | $CH_2$ | |
| 957 | c-$C_3H_5$ | 2,6-$(C_2H_5)_2$-3-Cl | S | $CH_2$ | $CH_2$ | |
| 958 | n-$C_4H_9$ | 2,6-$(C_2H_5)_2$-3-Cl | S | $CH_2$ | $CH_2$ | |
| 959 | s-$C_4H_9$ | 2,6-$(C_2H_5)_2$-3-Cl | S | $CH_2$ | $CH_2$ | |
| 960 | i-$C_4H_9$ | 2,6-$(C_2H_5)_2$-3-Cl | S | $CH_2$ | $CH_2$ | |
| 961 | t-$C_4H_9$ | 2,6-$(C_2H_5)_2$-3-Cl | S | $CH_2$ | $CH_2$ | |
| 962 | n-$C_5H_{11}$ | 2,6-$(C_2H_5)_2$-3-Cl | S | $CH_2$ | $CH_2$ | |
| 963 | neo-$C_5H_{11}$ | 2,6-$(C_2H_5)_2$-3-Cl | S | $CH_2$ | $CH_2$ | |
| 964 | c-$C_5H_9$ | 2,6-$(C_2H_5)_2$-3-Cl | S | $CH_2$ | $CH_2$ | |
| 965 | t-$C_5H_{11}$ | 2,6-$(C_2H_5)_2$-3-Cl | S | $CH_2$ | $CH_2$ | |
| 966 | $C_2H_5$ | 2-$CH_3$-3-Cl | S | $CH_2$ | $CH_2$ | |
| 967 | n-$C_3H_7$ | 2-$CH_3$-3-Cl | S | $CH_2$ | $CH_2$ | |
| 968 | i-$C_3H_7$ | 2-$CH_3$-3-Cl | S | $CH_2$ | $CH_2$ | |
| 969 | c-$C_3H_5$ | 2-$CH_3$-3-Cl | S | $CH_2$ | $CH_2$ | |
| 970 | n-$C_4H_9$ | 2-$CH_3$-3-Cl | S | $CH_2$ | $CH_2$ | |
| 971 | s-$C_4H_9$ | 2-$CH_3$-3-Cl | S | $CH_2$ | $CH_2$ | |
| 972 | i-$C_4H_9$ | 2-$CH_3$-3-Cl | S | $CH_2$ | $CH_2$ | |
| 973 | t-$C_4H_9$ | 2-$CH_3$-3-Cl | S | $CH_2$ | $CH_2$ | |
| 974 | n-$C_5H_{11}$ | 2-$CH_3$-3-Cl | S | $CH_2$ | $CH_2$ | |
| 975 | neo-$C_5H_{11}$ | 2-$CH_3$-3-Cl | S | $CH_2$ | $CH_2$ | |
| 976 | c-$C_5H_9$ | 2-$CH_3$-3-Cl | S | $CH_2$ | $CH_2$ | 164–167 |
| 978 | t-$C_5H_{11}$ | 2-$CH_3$-3-Cl | S | $CH_2$ | $CH_2$ | |
| 979 | $C_2H_5$ | 2,6-$(C_2H_5)_2$-3-Cl | $NCH_3$ | $CH_2$ | $CH_2$ | |
| 980 | n-$C_3H_7$ | 2,6-$(C_2H_5)_2$-3-Cl | $NCH_3$ | $CH_2$ | $CH_2$ | 152–155 |
| 981 | i-$C_3H_7$ | 2,6-$(C_2H_5)_2$-3-Cl | $NCH_3$ | $CH_2$ | $CH_2$ | |
| 982 | c-$C_3H_5$ | 2,6-$(C_2H_5)_2$-3-Cl | $NCH_3$ | $CH_2$ | $CH_2$ | |

TABLE 7-continued ( Het ) = Q⁷, R¹ = R² = Y = H )

| No | R³ | X | L | M | T | mp °C. |
|---|---|---|---|---|---|---|
| 983 | n-C₄H₉ | 2,6-(C₂H₅)₂-3-Cl | NCH₂ | CH₂ | CH₂ | |
| 984 | s-C₄H₉ | 2,6-(C₂H₅)₂-3-Cl | NCH₃ | CH₂ | CH₂ | |
| 985 | i-C₄H₉ | 2,6-(C₂H₅)₂-3-Cl | NCH₃ | CH₂ | CH₂ | |
| 986 | t-C₄H₉ | 2,6-(C₂H₅)₂-3-Cl | NCH₃ | CH₂ | CH₂ | |
| 987 | n-C₅H₁₁ | 2,6-(C₂H₅)₂-3-Cl | NCH₃ | CH₂ | CH₂ | |
| 988 | neo-C₅H₁₁ | 2,6-(C₂H₅)₂-3-Cl | NCH₃ | CH₂ | CH₂ | |
| 989 | c-C₅H₉ | 2,6-(C₂H₅)₂-3-Cl | NCH₃ | CH₂ | CH₂ | |
| 990 | t-C₅H₁₁ | 2,6-(C₂H₅)₂-3-Cl | NCH₃ | CH₂ | CH₂ | |
| 991 | C₂H₅ | 2,6-(C₂H₅)₂-3-Cl | CH₂ | CH₂ | O | |
| 992 | n-C₃H₇ | 2,6-(C₂H₅)₂-3-Cl | CH₂ | CH₂ | O | 214–217 |
| 993 | i-C₃H₇ | 2,6-(C₂H₅)₂-3-Cl | CH₂ | CH₂ | O | |
| 994 | c-C₃H₅ | 2,6-(C₂H₅)₂-3-Cl | CH₂ | CH₂ | O | |
| 995 | n-C₄H₉ | 2,6-(C₂H₅)₂-3-Cl | CH₂ | CH₂ | O | |
| 996 | s-C₄H₉ | 2,6-(C₂H₅)₂-3-Cl | CH₂ | CH₂ | O | |
| 997 | i-C₄H₉ | 2,6-(C₂H₅)₂-3-Cl | CH₂ | CH₂ | O | |
| 998 | t-C₄H₉ | 2,6-(C₂H₅)₂-3-Cl | CH₂ | CH₂ | O | |
| 999 | n-C₅H₁₁ | 2,6-(C₂H₅)₂-3-Cl | CH₂ | CH₂ | O | |
| 1000 | neo-C₅H₁₁ | 2,6-(C₂H₅)₂-3-Cl | CH₂ | CH₂ | O | |
| 1001 | c-C₅H₉ | 2,6-(C₂H₅)₂-3-Cl | CH₂ | CH₂ | O | |
| 1002 | t-C₅H₁₁ | 2,6-(C₂H₅)₂-3-Cl | CH₂ | CH₂ | O | |
| 1003 | C₂H₅ | 2-CH₃-3-Cl | CH₂ | CH₂ | O | |
| 1004 | n-C₃H₇ | 2-CH₃-3-Cl | CH₂ | CH₂ | O | |
| 1005 | i-C₃H₇ | 2-CH₃-3-Cl | CH₂ | CH₂ | O | |
| 1006 | c-C₃H₅ | 2-CH₃-3-Cl | CH₂ | CH₂ | O | |
| 1007 | n-C₄H₉ | 2-CH₃-3-Cl | CH₂ | CH₂ | O | |
| 1008 | s-C₄H₉ | 2-CH₃-3-Cl | CH₂ | CH₂ | O | |
| 1009 | i-C₄H₉ | 2-CH₃-3-Cl | CH₂ | CH₂ | O | |
| 1010 | t-C₄H₉ | 2-CH₃-3-Cl | CH₂ | CH₂ | O | |
| 1011 | n-C₅H₁₁ | 2-CH₃-3-Cl | CH₂ | CH₂ | O | |
| 1012 | neo-C₅H₁₁ | 2-CH₃-3-Cl | CH₂ | CH₂ | O | |
| 1013 | c-C₅H₉ | 2-CH₃-3-Cl | CH₂ | CH₂ | O | |
| 1014 | t-C₅H₁₁ | 2-CH₃-3-Cl | CH₂ | CH₂ | O | |
| 1015 | C₂H₅ | 2,6-(C₂H₅)₂-3-Cl | CH₂ | CH₂ | S | |
| 1016 | n-C₃H₇ | 2,6-(C₂H₅)₂-3-Cl | CH₂ | CH₂ | S | 211–213 |
| 1017 | i-C₃H₇ | 2,6-(C₂H₅)₂-3-Cl | CH₂ | CH₂ | S | |
| 1018 | c-C₃H₅ | 2,6-(C₂H₅)₂-3-Cl | CH₂ | CH₂ | S | |
| 1019 | n-C₄H₉ | 2,6-(C₂H₅)₂-3-Cl | CH₂ | CH₂ | S | |
| 1020 | s-C₄H₉ | 2,6-(C₂H₅)₂-3-Cl | CH₂ | CH₂ | S | |
| 1021 | i-C₄H₉ | 2,6-(C₂H₅)₂-3-Cl | CH₂ | CH₂ | S | |
| 1022 | t-C₄H₉ | 2,6-(C₂H₅)₂-3-Cl | CH₂ | CH₂ | S | |
| 1023 | n-C₅H₁₁ | 2,6-(C₂H₅)₂-3-Cl | CH₂ | CH₂ | S | |
| 1024 | neo-C₅H₁₁ | 2,6-(C₂H₅)₂-3-Cl | CH₂ | CH₂ | S | |
| 1025 | c-C₅H₉ | 2,6-(C₂H₅)₂-3-Cl | CH₂ | CH₂ | S | |
| 1026 | t-C₅H₁₁ | 2,6-(C₂H₅)₂-3-Cl | CH₂ | CH₂ | S | |
| 1027 | C₂H₅ | 2,6-(C₂H₅)₂-3-Cl | CH₂ | CH₂ | SO | |
| 1028 | n-C₃H₇ | 2,6-(C₂H₅)₂-3-Cl | CH₂ | CH₂ | SO | 230–233 |
| 1029 | i-C₃H₇ | 2,6-(C₂H₅)₂-3-Cl | CH₂ | CH₂ | SO | |
| 1030 | c-C₃H₅ | 2,6-(C₂H₅)₂-3-Cl | CH₂ | CH₂ | SO | |
| 1031 | n-C₄H₉ | 2,6-(C₂H₅)₂-3-Cl | CH₂ | CH₂ | SO | |
| 1032 | s-C₄H₉ | 2,6-(C₂H₅)₂-3-Cl | CH₂ | CH₂ | SO | |
| 1033 | i-C₄H₉ | 2,6-(C₂H₅)₂-3-Cl | CH₂ | CH₂ | SO | |
| 1034 | t-C₄H₉ | 2,6-(C₂H₅)₂-3-Cl | CH₂ | CH₂ | SO | |
| 1035 | n-C₅H₁₁ | 2,6-(C₂H₅)₂-3-Cl | CH₂ | CH₂ | SO | |
| 1036 | neo-C₅H₁₁ | 2,6-(C₂H₅)₂-3-Cl | CH₂ | CH₂ | SO | |
| 1037 | c-C₅H₉ | 2,6-(C₂H₅)₂-3-Cl | CH₂ | CH₂ | SO | |
| 1038 | t-C₅H₁₁ | 2,6-(C₂H₅)₂-3-Cl | CH₂ | CH₂ | SO | |
| 1039 | C₂H₅ | 2,6-(C₂H₅)₂-3-Cl | CH₂ | CH₂ | SO₂ | |
| 1040 | n-C₃H₇ | 2,6-(C₂H₅)₂-3-Cl | CH₂ | CH₂ | SO₂ | 198–200 |
| 1041 | i-C₃H₇ | 2,6-(C₂H₅)₂-3-Cl | CH₂ | CH₂ | SO₂ | |
| 1042 | c-C₃H₅ | 2,6-(C₂H₅)₂-3-Cl | CH₂ | CH₂ | SO₂ | |
| 1043 | n-C₄H₉ | 2,6-(C₂H₅)₂-3-Cl | CH₂ | CH₂ | SO₂ | |
| 1044 | s-C₄H₉ | 2,6-(C₂H₅)₂-3-Cl | CH₂ | CH₂ | SO₂ | |
| 1045 | i-C₄H₉ | 2,6-(C₂H₅)₂-3-Cl | CH₂ | CH₂ | SO₂ | |
| 1046 | t-C₄H₉ | 2,6-(C₂H₅)₂-3-Cl | CH₂ | CH₂ | SO₂ | |
| 1047 | n-C₅H₁₁ | 2,6-(C₂H₅)₂-3-Cl | CH₂ | CH₂ | SO₂ | |
| 1048 | neo-C₅H₁₁ | 2,6-(C₂H₅)₂-3-Cl | CH₂ | CH₂ | SO₂ | |
| 1049 | c-C₅H₉ | 2,6-(C₂H₅)₂-3-Cl | CH₂ | CH₂ | SO₂ | |
| 1050 | t-C₅H₁₁ | 2,6-(C₂H₅)₂-3-Cl | CH₂ | CH₂ | SO₂ | |
| 1051 | C₂H₅ | 2,6-(C₂H₅)₂-3-Cl | CH₂ | CH₂ | NCH₃ | |
| 1052 | n-C₃H₇ | 2,6-(C₂H₅)₂-3-Cl | CH₂ | CH₂ | NCH₃ | 157–160 |
| 1053 | i-C₃H₇ | 2,6-(C₂H₅)₂-3-Cl | CH₂ | CH₂ | NCH₃ | |
| 1054 | c-C₃H₅ | 2,6-(C₂H₅)₂-3-Cl | CH₂ | CH₂ | NCH₃ | |
| 1055 | n-C₄H₉ | 2,6-(C₂H₅)₂-3-Cl | CH₂ | CH₂ | NCH₃ | |
| 1056 | s-C₄H₉ | 2,6-(C₂H₅)₂-3-Cl | CH₂ | CH₂ | NCH₃ | |
| 1057 | i-C₄H₉ | 2,6-(C₂H₅)₂-3-Cl | CH₂ | CH₂ | NCH₃ | |
| 1058 | t-C₄H₉ | 2,6-(C₂H₅)₂-3-Cl | CH₂ | CH₂ | NCH₃ | |
| 1059 | n-C₅H₁₁ | 2,6-(C₂H₅)₂-3-Cl | CH₂ | CH₂ | NCH₃ | |
| 1060 | neo-C₅H₁₁ | 2,6-(C₂H₅)₂-3-Cl | CH₂ | CH₂ | NCH₃ | |
| 1061 | c-C₅H₉ | 2,6-(C₂H₅)₂-3-Cl | CH₂ | CH₂ | NCH₃ | |
| 1062 | t-C₅H₁₁ | 2,6-(C₂H₅)₂-3-Cl | CH₂ | CH₂ | NCH₃ | |

TABLE 8

( Het ) = Q⁸, R¹ = R² = Y = H )

| No | R³ | X | R¹⁴ | Z | mp °C. |
|---|---|---|---|---|---|
| 1063 | C₂H₅ | 2,6-(C₂H₅)₂-3-Cl | CH₃ | O | |
| 1064 | n-C₃H₇ | 2,6-(C₂H₅)₂-3-Cl | CH₃ | O | 189–192 |
| 1065 | i-C₃H₇ | 2,6-(C₂H₅)₂-3-Cl | CH₃ | O | |
| 1066 | c-C₃H₅ | 2,6-(C₂H₅)₂-3-Cl | CH₃ | O | |
| 1067 | n-C₄H₉ | 2,6-(C₂H₅)₂-3-Cl | CH₃ | O | |
| 1068 | s-C₄H₉ | 2,6-(C₂H₅)₂-3-Cl | CH₃ | O | |
| 1069 | i-C₄H₉ | 2,6-(C₂H₅)₂-3-Cl | CH₃ | O | |
| 1070 | t-C₄H₉ | 2,6-(C₂H₅)₂-3-Cl | CH₃ | O | |
| 1071 | n-C₅H₁₁ | 2,6-(C₂H₅)₂-3-Cl | CH₃ | O | |
| 1072 | neo-C₅H₁₁ | 2,6-(C₂H₅)₂-3-Cl | CH₃ | O | |
| 1073 | c-C₅H₉ | 2,6-(C₂H₅)₂-3-Cl | CH₃ | O | |
| 1074 | t-C₅H₁₁ | 2,6-(C₂H₅)₂-3-Cl | CH₃ | O | |
| 1075 | C₂H₅ | 2-CH₃-3-Cl | CH₃ | O | |
| 1076 | n-C₃H₇ | 2-CH₃-3-Cl | CH₃ | O | |
| 1077 | i-C₃H₇ | 2-CH₃-3-Cl | CH₃ | O | |
| 1078 | c-C₃H₅ | 2-CH₃-3-Cl | CH₃ | O | |
| 1079 | n-C₄H₉ | 2-CH₃-3-Cl | CH₃ | O | |
| 1080 | s-C₄H₉ | 2-CH₃-3-Cl | CH₃ | O | |
| 1081 | i-C₄H₉ | 2-CH₃-3-Cl | CH₃ | O | |
| 1082 | t-C₄H₉ | 2-CH₃-3-Cl | CH₃ | O | |
| 1083 | n-C₅H₁₁ | 2-CH₃-3-Cl | CH₃ | O | |
| 1084 | neo-C₅H₁₁ | 2-CH₃-3-Cl | CH₃ | O | |
| 1085 | c-C₅H₉ | 2-CH₃-3-Cl | CH₃ | O | 192–195 |
| 1086 | t-C₅H₁₁ | 2-CH₃-3-Cl | CH₃ | O | |
| 1087 | C₂H₅ | 2,6-(C₂H₅)₂-3-Cl | H | NCH₃ | 239–241 |
| 1088 | n-C₃H₇ | 2,6-(C₂H₅)₂-3-Cl | H | NCH₃ | 230–233 |
| 1089 | i-C₃H₇ | 2,6-(C₂H₅)₂-3-Cl | H | NCH₃ | |
| 1090 | c-C₃H₅ | 2,6-(C₂H₅)₂-3-Cl | H | NCH₃ | |
| 1091 | n-C₄H₉ | 2,6-(C₂H₅)₂-3-Cl | H | NCH₃ | |
| 1092 | s-C₄H₉ | 2,6-(C₂H₅)₂-3-Cl | H | NCH₃ | |
| 1093 | i-C₄H₉ | 2,6-(C₂H₅)₂-3-Cl | H | NCH₃ | |
| 1094 | t-C₄H₉ | 2,6-(C₂H₅)₂-3-Cl | H | NCH₃ | |
| 1095 | n-C₅H₁₁ | 2,6-(C₂H₅)₂-3-Cl | H | NCH₃ | |
| 1096 | neo-C₅H₁₁ | 2,6-(C₂H₅)₂-3-Cl | H | NCH₃ | |
| 1097 | c-C₅H₉ | 2,6-(C₂H₅)₂-3-Cl | H | NCH₃ | |
| 1098 | t-C₅H₁₁ | 2,6-(C₂H₅)₂-3-Cl | H | NCH₃ | |
| 1099 | C₂H₅ | 2-CH₃-3-Cl | H | NCH₃ | |
| 1100 | n-C₃H₇ | 2-CH₃-3-Cl | H | NCH₃ | |
| 1101 | i-C₃H₇ | 2-CH₃-3-Cl | H | NCH₃ | |
| 1102 | c-C₃H₅ | 2-CH₃-3-Cl | H | NCH₃ | |
| 1103 | n-C₄H₉ | 2-CH₃-3-Cl | H | NCH₃ | |
| 1104 | s-C₄H₉ | 2-CH₃-3-Cl | H | NCH₃ | |

TABLE 8-continued

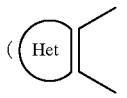 = Q$^8$, R$^1$ = R$^2$ = Y = H)

| No | R$^3$ | X | R$^{14}$ | Z | mp ° C. |
|---|---|---|---|---|---|
| 1105 | i-C$_4$H$_9$ | 2-CH$_3$-3-Cl | H | NCH$_3$ | |
| 1106 | t-C$_4$H$_9$ | 2-CH$_3$-3-Cl | H | NCH$_3$ | |
| 1107 | n-C$_5$H$_{11}$ | 2-CH$_3$-3-Cl | H | NCH$_3$ | |
| 1108 | neo-C$_5$H$_{11}$ | 2-CH$_3$-3-Cl | H | NCH$_3$ | |
| 1109 | c-C$_5$H$_9$ | 2-CH$_3$-3-Cl | H | NCH$_3$ | |
| 1110 | t-C$_5$H$_{11}$ | 2-CH$_3$-3-Cl | H | NCH$_3$ | |
| 1111 | C$_2$H$_5$ | 2,6-(C$_2$H$_5$)$_2$-3-Cl | CH$_3$ | NCH$_3$ | |
| 1112 | n-C$_3$H$_7$ | 2,6-(C$_2$H$_5$)$_2$-3-Cl | CH$_3$ | NCH$_3$ | 211–215 |
| 1113 | i-C$_3$H$_7$ | 2,6-(C$_2$H$_5$)$_2$-3-Cl | CH$_3$ | NCH$_3$ | |
| 1114 | c-C$_3$H$_5$ | 2,6-(C$_2$H$_5$)$_2$-3-Cl | CH$_3$ | NCH$_3$ | |
| 1115 | n-C$_4$H$_9$ | 2,6-(C$_2$H$_5$)$_2$-3-Cl | CH$_3$ | NCH$_3$ | |
| 1116 | s-C$_4$H$_9$ | 2,6-(C$_2$H$_5$)$_2$-3-Cl | CH$_3$ | NCH$_3$ | |
| 1117 | i-C$_4$H$_9$ | 2,6-(C$_2$H$_5$)$_2$-3-Cl | CH$_3$ | NCH$_3$ | |
| 1118 | t-C$_4$H$_9$ | 2,6-(C$_2$H$_5$)$_2$-3-Cl | CH$_3$ | NCH$_3$ | |
| 1119 | n-C$_5$H$_{11}$ | 2,6-(C$_2$H$_5$)$_2$-3-Cl | CH$_3$ | NCH$_3$ | |
| 1120 | neo-C$_5$H$_{11}$ | 2,6-(C$_2$H$_5$)$_2$-3-Cl | CH$_3$ | NCH$_3$ | |
| 1121 | c-C$_5$H$_9$ | 2,6-(C$_2$H$_5$)$_2$-3-Cl | CH$_3$ | NCH$_3$ | |
| 1122 | t-C$_5$H$_{11}$ | 2,6-(C$_2$H$_5$)$_2$-3-Cl | CH$_3$ | NCH$_3$ | |

TABLE 9

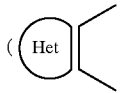 = Q$^9$, R$^1$ = R$^2$ = Y = H)

| No | R$^3$ | X | R$^{14}$ | Z | mp ° C. |
|---|---|---|---|---|---|
| 1123 | C$_2$H$_5$ | 2,6-(C$_2$H$_5$)$_2$-3-Cl | H | NCH$_3$ | |
| 1124 | n-C$_3$H$_7$ | 2,6-(C$_2$H$_5$)$_2$-3-Cl | H | NCH$_3$ | 217–220 |
| 1125 | i-C$_3$H$_7$ | 2,6-(C$_2$H$_5$)$_2$-3-Cl | H | NCH$_3$ | |
| 1126 | c-C$_3$H$_5$ | 2,6-(C$_2$H$_5$)$_2$-3-Cl | H | NCH$_3$ | |
| 1127 | n-C$_4$H$_9$ | 2,6-(C$_2$H$_5$)$_2$-3-Cl | H | NCH$_3$ | |
| 1128 | s-C$_4$H$_9$ | 2,6-(C$_2$H$_5$)$_2$-3-Cl | H | NCH$_3$ | |
| 1129 | i-C$_4$H$_9$ | 2,6-(C$_2$H$_5$)$_2$-3-Cl | H | NCH$_3$ | |
| 1130 | t-C$_4$H$_9$ | 2,6-(C$_2$H$_5$)$_2$-3-Cl | H | NCH$_3$ | |
| 1131 | n-C$_5$H$_{11}$ | 2,6-(C$_2$H$_5$)$_2$-3-Cl | H | NCH$_3$ | |
| 1132 | neo-C$_5$H$_{11}$ | 2,6-(C$_2$H$_5$)$_2$-3-Cl | H | NCH$_3$ | |
| 1133 | c-C$_5$H$_9$ | 2,6-(C$_2$H$_5$)$_2$-3-Cl | H | NCH$_3$ | |
| 1134 | t-C$_5$H$_{11}$ | 2,6-(C$_2$H$_5$)$_2$-3-Cl | H | NCH$_3$ | |
| 1135 | C$_2$H$_5$ | 2,6-(C$_2$H$_5$)$_2$-3-Cl | CH$_3$ | NCH$_3$ | |
| 1136 | n-C$_3$H$_7$ | 2,6-(C$_2$H$_5$)$_2$-3-Cl | CH$_3$ | NCH$_3$ | 211–214 |
| 1137 | i-C$_3$H$_7$ | 2,6-(C$_2$H$_5$)$_2$-3-Cl | CH$_3$ | NCH$_3$ | |
| 1138 | c-C$_3$H$_5$ | 2,6-(C$_2$H$_5$)$_2$-3-Cl | CH$_3$ | NCH$_3$ | |
| 1139 | n-C$_4$H$_9$ | 2,6-(C$_2$H$_5$)$_2$-3-Cl | CH$_3$ | NCH$_3$ | |
| 1140 | s-C$_4$H$_9$ | 2,6-(C$_2$H$_5$)$_2$-3-Cl | CH$_3$ | NCH$_3$ | |
| 1141 | i-C$_4$H$_9$ | 2,6-(C$_2$H$_5$)$_2$-3-Cl | CH$_3$ | NCH$_3$ | |
| 1142 | t-C$_4$H$_9$ | 2,6-(C$_2$H$_5$)$_2$-3-Cl | CH$_3$ | NCH$_3$ | |
| 1143 | n-C$_5$H$_{11}$ | 2,6-(C$_2$H$_5$)$_2$-3-Cl | CH$_3$ | NCH$_3$ | |
| 1144 | neo-C$_5$H$_{11}$ | 2,6-(C$_2$H$_5$)$_2$-3-Cl | CH$_3$ | NCH$_3$ | |
| 1145 | c-C$_5$H$_9$ | 2,6-(C$_2$H$_5$)$_2$-3-Cl | CH$_3$ | NCH$_3$ | |
| 1146 | t-C$_5$H$_{11}$ | 2,6-(C$_2$H$_5$)$_2$-3-Cl | CH$_3$ | NCH$_3$ | |

TABLE 10

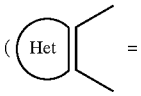 = Q$^{10}$, R$^1$ = R$^2$ = Y = H)

| No | R$^3$ | X | R$^{14}$ | Z | mp ° C. |
|---|---|---|---|---|---|
| 1147 | C$_2$H$_5$ | 2,6-(C$_2$H$_5$)$_2$-3-Cl | H | NCH$_3$ | |
| 1148 | n-C$_3$H$_7$ | 2,6-(C$_2$H$_5$)$_2$-3-Cl | H | NCH$_3$ | 225–228 |
| 1149 | i-C$_3$H$_7$ | 2,6-(C$_2$H$_5$)$_2$-3-Cl | H | NCH$_3$ | |

TABLE 10-continued

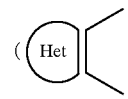 = Q$^{10}$, R$^1$ = R$^2$ = Y = H)

| No | R$^3$ | X | R$^{14}$ | Z | mp ° C. |
|---|---|---|---|---|---|
| 1150 | c-C$_3$H$_5$ | 2,6-(C$_2$H$_5$)$_2$-3-Cl | H | NCH$_3$ | |
| 1151 | n-C$_4$H$_9$ | 2,6-(C$_2$H$_5$)$_2$-3-Cl | H | NCH$_3$ | |
| 1152 | s-C$_4$H$_9$ | 2,6-(C$_2$H$_5$)$_2$-3-Cl | H | NCH$_3$ | |
| 1153 | i-C$_4$H$_9$ | 2,6-(C$_2$H$_5$)$_2$-3-Cl | H | NCH$_3$ | |
| 1154 | t-C$_4$H$_9$ | 2,6-(C$_2$H$_5$)$_2$-3-Cl | H | NCH$_3$ | |
| 1155 | n-C$_5$H$_{11}$ | 2,6-(C$_2$H$_5$)$_2$-3-Cl | H | NCH$_3$ | |
| 1156 | neo-C$_5$H$_{11}$ | 2,6-(C$_2$H$_5$)$_2$-3-Cl | H | NCH$_3$ | |
| 1157 | c-C$_5$H$_9$ | 2,6-(C$_2$H$_5$)$_2$-3-Cl | H | NCH$_3$ | |
| 1158 | t-C$_5$H$_{11}$ | 2,6-(C$_2$H$_5$)$_2$-3-Cl | H | NCH$_3$ | |
| 1159 | C$_2$H$_5$ | 2,6-(C$_2$H$_5$)$_2$-3-Cl | CH$_3$ | NCH$_3$ | |
| 1160 | n-C$_3$H$_7$ | 2,6-(C$_2$H$_5$)$_2$-3-Cl | CH$_3$ | NCH$_3$ | 220–224 |
| 1161 | i-C$_3$H$_7$ | 2,6-(C$_2$H$_5$)$_2$-3-Cl | CH$_3$ | NCH$_3$ | |
| 1162 | c-C$_3$H$_5$ | 2,6-(C$_2$H$_5$)$_2$-3-Cl | CH$_3$ | NCH$_3$ | |
| 1163 | n-C$_4$H$_9$ | 2,6-(C$_2$H$_5$)$_2$-3-Cl | CH$_3$ | NCH$_3$ | |
| 1164 | s-C$_4$H$_9$ | 2,6-(C$_2$H$_5$)$_2$-3-Cl | CH$_3$ | NCH$_3$ | |
| 1165 | i-C$_4$H$_9$ | 2,6-(C$_2$H$_5$)$_2$-3-Cl | CH$_3$ | NCH$_3$ | |
| 1166 | t-C$_4$H$_9$ | 2,6-(C$_2$H$_5$)$_2$-3-Cl | CH$_3$ | NCH$_3$ | |
| 1167 | n-C$_5$H$_{11}$ | 2,6-(C$_2$H$_5$)$_2$-3-Cl | CH$_3$ | NCH$_3$ | |
| 1168 | neo-C$_5$H$_{11}$ | 2,6-(C$_2$H$_5$)$_2$-3-Cl | CH$_3$ | NCH$_3$ | |
| 1169 | c-C$_5$H$_9$ | 2,6-(C$_2$H$_5$)$_2$-3-Cl | CH$_3$ | NCH$_3$ | |
| 1170 | t-C$_5$H$_{11}$ | 2,6-(C$_2$H$_5$)$_2$-3-Cl | CH$_3$ | NCH$_3$ | |

TABLE 11

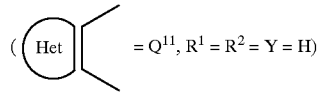 = Q$^{11}$, R$^1$ = R$^2$ = Y = H)

| No | R$^3$ | X | R$^{14}$ | Z | mp ° C. |
|---|---|---|---|---|---|
| 1171 | CH$_3$ | 2,6-(C$_2$H$_5$)$_2$-3-Cl | H | NCH$_3$ | 216–218 |
| 1172 | C$_2$H$_5$ | 2,6-(C$_2$H$_5$)$_2$-3-Cl | H | NCH$_3$ | |
| 1173 | n-C$_3$H$_7$ | 2,6-(C$_2$H$_5$)$_2$-3-Cl | H | NCH$_3$ | 213–216 |
| 1174 | i-C$_3$H$_7$ | 2,6-(C$_2$H$_5$)$_2$-3-Cl | H | NCH$_3$ | |
| 1175 | c-C$_3$H$_5$ | 2,6-(C$_2$H$_5$)$_2$-3-Cl | H | NCH$_3$ | |
| 1176 | n-C$_4$H$_9$ | 2,6-(C$_2$H$_5$)$_2$-3-Cl | H | NCH$_3$ | |
| 1177 | s-C$_4$H$_9$ | 2,6-(C$_2$H$_5$)$_2$-3-Cl | H | NCH$_3$ | |
| 1178 | i-C$_4$H$_9$ | 2,6-(C$_2$H$_5$)$_2$-3-Cl | H | NCH$_3$ | |
| 1179 | t-C$_4$H$_9$ | 2,6-(C$_2$H$_5$)$_2$-3-Cl | H | NCH$_3$ | |
| 1180 | n-C$_5$H$_{11}$ | 2,6-(C$_2$H$_5$)$_2$-3-Cl | H | NCH$_3$ | |
| 1181 | neo-C$_5$H$_{11}$ | 2,6-(C$_2$H$_5$)$_2$-3-Cl | H | NCH$_3$ | |
| 1182 | c-C$_5$H$_9$ | 2,6-(C$_2$H$_5$)$_2$-3-Cl | H | NCH$_3$ | |
| 1183 | t-C$_5$H$_{11}$ | 2,6-(C$_2$H$_5$)$_2$-3-Cl | H | NCH$_3$ | |
| 1184 | C$_2$H$_5$ | 2-CH$_3$-3-Cl | H | NCH$_3$ | |
| 1185 | n-C$_3$H$_7$ | 2-CH$_3$-3-Cl | H | NCH$_3$ | |
| 1186 | i-C$_3$H$_7$ | 2-CH$_3$-3-Cl | H | NCH$_3$ | |
| 1187 | c-C$_3$H$_5$ | 2-CH$_3$-3-Cl | H | NCH$_3$ | |
| 1188 | n-C$_4$H$_9$ | 2-CH$_3$-3-Cl | H | NCH$_3$ | |
| 1189 | s-C$_4$H$_9$ | 2-CH$_3$-3-Cl | H | NCH$_3$ | |
| 1190 | i-C$_4$H$_9$ | 2-CH$_3$-3-Cl | H | NCH$_3$ | |
| 1191 | t-C$_4$H$_9$ | 2-CH$_3$-3-Cl | H | NCH$_3$ | |
| 1192 | n-C$_5$H$_{11}$ | 2-CH$_3$-3-Cl | H | NCH$_3$ | |
| 1193 | neo-C$_5$H$_{11}$ | 2-CH$_3$-3-Cl | H | NCH$_3$ | |
| 1194 | c-C$_5$H$_9$ | 2-CH$_3$-3-Cl | H | NCH$_3$ | |
| 1195 | t-C$_5$H$_{11}$ | 2-CH$_3$-3-Cl | H | NCH$_3$ | |
| 1196 | C$_2$H$_5$ | 2,6-(C$_2$H$_5$)$_2$-3-Cl | CH$_3$ | NCH$_3$ | |
| 1197 | n-C$_3$H$_7$ | 2,6-(C$_2$H$_5$)$_2$-3-Cl | CH$_3$ | NCH$_3$ | 209–212 |
| 1198 | i-C$_3$H$_7$ | 2,6-(C$_2$H$_5$)$_2$-3-Cl | CH$_3$ | NCH$_3$ | |
| 1199 | c-C$_3$H$_5$ | 2,6-(C$_2$H$_5$)$_2$-3-Cl | CH$_3$ | NCH$_3$ | |
| 1200 | n-C$_4$H$_9$ | 2,6-(C$_2$H$_5$)$_2$-3-Cl | CH$_3$ | NCH$_3$ | |
| 1201 | s-C$_4$H$_9$ | 2,6-(C$_2$H$_5$)$_2$-3-Cl | CH$_3$ | NCH$_3$ | |
| 1202 | i-C$_4$H$_9$ | 2,6-(C$_2$H$_5$)$_2$-3-Cl | CH$_3$ | NCH$_3$ | |
| 1203 | t-C$_4$H$_9$ | 2,6-(C$_2$H$_5$)$_2$-3-Cl | CH$_3$ | NCH$_3$ | |
| 1204 | n-C$_5$H$_{11}$ | 2,6-(C$_2$H$_5$)$_2$-3-Cl | CH$_3$ | NCH$_3$ | |
| 1205 | neo-C$_5$H$_{11}$ | 2,6-(C$_2$H$_5$)$_2$-3-Cl | CH$_3$ | NCH$_3$ | |

TABLE 11-continued

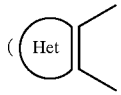

( Het  = Q$^{11}$, R$^1$ = R$^2$ = Y = H)

| No | R$^3$ | X | R$^{14}$ | Z | mp ° C. |
|---|---|---|---|---|---|
| 1206 | c-C$_5$H$_9$ | 2,6-(C$_2$H$_5$)$_2$-3-Cl | CH$_3$ | NCH$_3$ | |
| 1207 | t-C$_5$H$_{11}$ | 2,6-(C$_2$H$_5$)$_2$-3-Cl | CH$_3$ | NCH$_3$ | |

TABLE 12

( Het  = Q$^{12}$, R$^1$ = R$^2$ = Y = H)

| No | R$^3$ | X | R$^{14}$ | Z | mp ° C. |
|---|---|---|---|---|---|
| 1208 | C$_2$H$_5$ | 2,6-(C$_2$H$_5$)$_2$-3-Cl | H | NCH$_3$ | |
| 1209 | n-C$_3$H$_7$ | 2,6-(C$_2$H$_5$)$_2$-3-Cl | H | NCH$_3$ | 222–225 |
| 1210 | i-C$_3$H$_7$ | 2,6-(C$_2$H$_5$)$_2$-3-Cl | H | NCH$_3$ | |
| 1211 | c-C$_3$H$_5$ | 2,6-(C$_2$H$_5$)$_2$-3-Cl | H | NCH$_3$ | |
| 1212 | n-C$_4$H$_9$ | 2,6-(C$_2$H$_5$)$_2$-3-Cl | H | NCH$_3$ | |
| 1213 | s-C$_4$H$_9$ | 2,6-(C$_2$H$_5$)$_2$-3-Cl | H | NCH$_3$ | |
| 1214 | i-C$_4$H$_9$ | 2,6-(C$_2$H$_5$)$_2$-3-Cl | H | NCH$_3$ | |
| 1215 | t-C$_4$H$_9$ | 2,6-(C$_2$H$_5$)$_2$-3-Cl | H | NCH$_3$ | |
| 1216 | n-C$_5$H$_{11}$ | 2,6-(C$_2$H$_5$)$_2$-3-Cl | H | NCH$_3$ | |
| 1217 | neo-C$_5$H$_{11}$ | 2,6-(C$_2$H$_5$)$_2$-3-Cl | H | NCH$_3$ | |
| 1218 | c-C$_5$H$_9$ | 2,6-(C$_2$H$_5$)$_2$-3-Cl | H | NCH$_3$ | |
| 1219 | t-C$_5$H$_{11}$ | 2,6-(C$_2$H$_5$)$_2$-3-Cl | H | NCH$_3$ | |
| 1220 | C$_2$H$_5$ | 2-CH$_3$-3-Cl | H | NCH$_3$ | |
| 1221 | n-C$_3$H$_7$ | 2-CH$_3$-3-Cl | H | NCH$_3$ | |
| 1222 | i-C$_3$H$_7$ | 2-CH$_3$-3-Cl | H | NCH$_3$ | |
| 1223 | c-C$_3$H$_5$ | 2-CH$_3$-3-Cl | H | NCH$_3$ | |
| 1224 | n-C$_4$H$_9$ | 2-CH$_3$-3-Cl | H | NCH$_3$ | |
| 1225 | s-C$_4$H$_9$ | 2-CH$_3$-3-Cl | H | NCH$_3$ | |
| 1226 | i-C$_4$H$_9$ | 2-CH$_3$-3-Cl | H | NCH$_3$ | |
| 1227 | t-C$_4$H$_9$ | 2-CH$_3$-3-Cl | H | NCH$_3$ | |
| 1228 | n-C$_5$H$_{11}$ | 2-CH$_3$-3-Cl | H | NCH$_3$ | |
| 1229 | neo-C$_5$H$_{11}$ | 2-CH$_3$-3-Cl | H | NCH$_3$ | |
| 1230 | c-C$_5$H$_9$ | 2-CH$_3$-3-Cl | H | NCH$_3$ | |
| 1231 | t-C$_5$H$_{11}$ | 2-CH$_3$-3-Cl | H | NCH$_3$ | |
| 1232 | C$_2$H$_5$ | 2,6-(C$_2$H$_5$)$_2$-3-Cl | CH$_3$ | NCH$_3$ | |
| 1233 | n-C$_3$H$_7$ | 2,6-(C$_2$H$_5$)$_2$-3-Cl | CH$_3$ | NCH$_3$ | 215–218 |
| 1234 | i-C$_3$H$_7$ | 2,6-(C$_2$H$_5$)$_2$-3-Cl | CH$_3$ | NCH$_3$ | |
| 1235 | c-C$_3$H$_5$ | 2,6-(C$_2$H$_5$)$_2$-3-Cl | CH$_3$ | NCH$_3$ | |
| 1236 | n-C$_4$H$_9$ | 2,6-(C$_2$H$_5$)$_2$-3-Cl | CH$_3$ | NCH$_3$ | |
| 1237 | s-C$_4$H$_9$ | 2,6-(C$_2$H$_5$)$_2$-3-Cl | CH$_3$ | NCH$_3$ | |
| 1238 | i-C$_4$H$_9$ | 2,6-(C$_2$H$_5$)$_2$-3-Cl | CH$_3$ | NCH$_3$ | |
| 1239 | t-C$_4$H$_9$ | 2,6-(C$_2$H$_5$)$_2$-3-Cl | CH$_3$ | NCH$_3$ | |
| 1240 | n-C$_5$H$_{11}$ | 2,6-(C$_2$H$_5$)$_2$-3-Cl | CH$_3$ | NCH$_3$ | |
| 1241 | neo-C$_5$H$_{11}$ | 2,6-(C$_2$H$_5$)$_2$-3-Cl | CH$_3$ | NCH$_3$ | |
| 1242 | c-C$_5$H$_9$ | 2,6-(C$_2$H$_5$)$_2$-3-Cl | CH$_3$ | NCH$_3$ | |
| 1243 | t-C$_5$H$_{11}$ | 2,6-(C$_2$H$_5$)$_2$-3-Cl | CH$_3$ | NCH$_3$ | |

TABLE 13

( Het  = Q$^{13}$, R$^1$ = R$^2$ = Y = H)

| No | R$^3$ | X | R$^{14}$ | Z | mp ° C. |
|---|---|---|---|---|---|
| 1244 | C$_2$H$_5$ | 2,6-(C$_2$H$_5$)$_2$-3-Cl | H | O | |
| 1245 | n-C$_3$H$_7$ | 2,6-(C$_2$H$_5$)$_2$-3-Cl | H | O | 189–195 |
| 1246 | i-C$_3$H$_7$ | 2,6-(C$_2$H$_5$)$_2$-3-Cl | H | O | |
| 1247 | c-C$_3$H$_5$ | 2,6-(C$_2$H$_5$)$_2$-3-Cl | H | O | |
| 1248 | n-C$_4$H$_9$ | 2,6-(C$_2$H$_5$)$_2$-3-Cl | H | O | |
| 1249 | s-C$_4$H$_9$ | 2,6-(C$_2$H$_5$)$_2$-3-Cl | H | O | |
| 1250 | i-C$_4$H$_9$ | 2,6-(C$_2$H$_5$)$_2$-3-Cl | H | O | |

TABLE 13-continued ( Het  = Q$^{13}$, R$^1$ = R$^2$ = Y = H)

| No | R$^3$ | X | R$^{14}$ | Z | mp ° C. |
|---|---|---|---|---|---|
| 1251 | t-C$_4$H$_9$ | 2,6-(C$_2$H$_5$)$_2$-3-Cl | H | O | |
| 1252 | n-C$_5$H$_{11}$ | 2,6-(C$_2$H$_5$)$_2$-3-Cl | H | O | |
| 1253 | neo-C$_5$H$_{11}$ | 2,6-(C$_2$H$_5$)$_2$-3-Cl | H | O | |
| 1254 | c-C$_5$H$_9$ | 2,6-(C$_2$H$_5$)$_2$-3-Cl | H | O | |
| 1255 | t-C$_5$H$_{11}$ | 2,6-(C$_2$H$_5$)$_2$-3-Cl | H | O | |
| 1256 | C$_2$H$_5$ | 2,6-(C$_2$H$_5$)$_2$-3-Cl | CH$_3$ | O | |
| 1257 | n-C$_3$H$_7$ | 2,6-(C$_2$H$_5$)$_2$-3-Cl | CH$_3$ | O | |
| 1258 | i-C$_3$H$_7$ | 2,6-(C$_2$H$_5$)$_2$-3-Cl | CH$_3$ | O | |
| 1259 | c-C$_3$H$_5$ | 2,6-(C$_2$H$_5$)$_2$-3-Cl | CH$_3$ | O | |
| 1260 | n-C$_4$H$_9$ | 2,6-(C$_2$H$_5$)$_2$-3-Cl | CH$_3$ | O | |
| 1261 | s-C$_4$H$_9$ | 2,6-(C$_2$H$_5$)$_2$-3-Cl | CH$_3$ | O | |
| 1262 | i-C$_4$H$_9$ | 2,6-(C$_2$H$_5$)$_2$-3-Cl | CH$_3$ | O | |
| 1263 | t-C$_4$H$_9$ | 2,6-(C$_2$H$_5$)$_2$-3-Cl | CH$_3$ | O | |
| 1264 | n-C$_5$H$_{11}$ | 2,6-(C$_2$H$_5$)$_2$-3-Cl | CH$_3$ | O | |
| 1265 | neo-C$_5$H$_{11}$ | 2,6-(C$_2$H$_5$)$_2$-3-Cl | CH$_3$ | O | |
| 1266 | c-C$_5$H$_9$ | 2,6-(C$_2$H$_5$)$_2$-3-Cl | CH$_3$ | O | |
| 1267 | t-C$_5$H$_{11}$ | 2,6-(C$_2$H$_5$)$_2$-3-Cl | CH$_3$ | O | |
| 1268 | C$_2$H$_5$ | 2,6-(C$_2$H$_5$)$_2$-3-Cl | H | NCH$_3$ | |
| 1269 | n-C$_3$H$_7$ | 2,6-(C$_2$H$_5$)$_2$-3-Cl | H | NCH$_3$ | 198–202 |
| 1270 | i-C$_3$H$_7$ | 2,6-(C$_2$H$_5$)$_2$-3-Cl | H | NCH$_3$ | |
| 1271 | c-C$_3$H$_5$ | 2,6-(C$_2$H$_5$)$_2$-3-Cl | H | NCH$_3$ | |
| 1272 | n-C$_4$H$_9$ | 2,6-(C$_2$H$_5$)$_2$-3-Cl | H | NCH$_3$ | |
| 1273 | s-C$_4$H$_9$ | 2,6-(C$_2$H$_5$)$_2$-3-Cl | H | NCH$_3$ | |
| 1274 | i-C$_4$H$_9$ | 2,6-(C$_2$H$_5$)$_2$-3-Cl | H | NCH$_3$ | |
| 1275 | t-C$_4$H$_9$ | 2,6-(C$_2$H$_5$)$_2$-3-Cl | H | NCH$_3$ | |
| 1276 | n-C$_5$H$_{11}$ | 2,6-(C$_2$H$_5$)$_2$-3-Cl | H | NCH$_3$ | |
| 1277 | neo-C$_5$H$_{11}$ | 2,6-(C$_2$H$_5$)$_2$-3-Cl | H | NCH$_3$ | |
| 1278 | c-C$_5$H$_9$ | 2,6-(C$_2$H$_5$)$_2$-3-Cl | H | NCH$_3$ | |
| 1279 | t-C$_5$H$_{11}$ | 2,6-(C$_2$H$_5$)$_2$-3-Cl | H | NCH$_3$ | |
| 1280 | C$_2$H$_5$ | 2-CH$_3$-3-Cl | H | NCH$_3$ | |
| 1281 | n-C$_3$H$_7$ | 2-CH$_3$-3-Cl | H | NCH$_3$ | |
| 1282 | i-C$_3$H$_7$ | 2-CH$_3$-3-Cl | H | NCH$_3$ | |
| 1283 | c-C$_3$H$_5$ | 2-CH$_3$-3-Cl | H | NCH$_3$ | |
| 1284 | n-C$_4$H$_9$ | 2-CH$_3$-3-Cl | H | NCH$_3$ | |
| 1285 | s-C$_4$H$_9$ | 2-CH$_3$-3-Cl | H | NCH$_3$ | |
| 1286 | i-C$_4$H$_9$ | 2-CH$_3$-3-Cl | H | NCH$_3$ | |
| 1287 | t-C$_4$H$_9$ | 2-CH$_3$-3-Cl | H | NCH$_3$ | |
| 1288 | n-C$_5$H$_{11}$ | 2-CH$_3$-3-Cl | H | NCH$_3$ | |
| 1289 | neo-C$_5$H$_{11}$ | 2-CH$_3$-3-Cl | H | NCH$_3$ | |
| 1290 | c-C$_5$H$_9$ | 2-CH$_3$-3-Cl | H | NCH$_3$ | |
| 1291 | s-C$_5$H$_{11}$ | 2-CH$_3$-3-Cl | H | NCH$_3$ | |
| 1292 | t-C$_5$H$_{11}$ | 2-CH$_3$-3-Cl | H | NCH$_3$ | |
| 1293 | C$_2$H$_5$ | 2,6-(C$_2$H$_5$)$_2$-3-Cl | CH$_3$ | NCH$_3$ | |
| 1294 | n-C$_3$H$_7$ | 2,6-(C$_2$H$_5$)$_2$-3-Cl | CH$_3$ | NCH$_3$ | 201–205 |
| 1295 | i-C$_3$H$_7$ | 2,6-(C$_2$H$_5$)$_2$-3-Cl | CH$_3$ | NCH$_3$ | |
| 1296 | c-C$_3$H$_5$ | 2,6-(C$_2$H$_5$)$_2$-3-Cl | CH$_3$ | NCH$_3$ | |
| 1297 | n-C$_4$H$_9$ | 2,6-(C$_2$H$_5$)$_2$-3-Cl | CH$_3$ | NCH$_3$ | |
| 1298 | s-C$_4$H$_9$ | 2,6-(C$_2$H$_5$)$_2$-3-Cl | CH$_3$ | NCH$_3$ | |
| 1299 | i-C$_4$H$_9$ | 2,6-(C$_2$H$_5$)$_2$-3-Cl | CH$_3$ | NCH$_3$ | |
| 1300 | t-C$_4$H$_9$ | 2,6-(C$_2$H$_5$)$_2$-3-Cl | CH$_3$ | NCH$_3$ | |
| 1301 | n-C$_5$H$_{11}$ | 2,6-(C$_2$H$_5$)$_2$-3-Cl | CH$_3$ | NCH$_3$ | |
| 1302 | neo-C$_5$H$_{11}$ | 2,6-(C$_2$H$_5$)$_2$-3-Cl | CH$_3$ | NCH$_3$ | |
| 1303 | c-C$_5$H$_9$ | 2,6-(C$_2$H$_5$)$_2$-3-Cl | CH$_3$ | NCH$_3$ | |
| 1304 | t-C$_5$H$_{11}$ | 2,6-(C$_2$H$_5$)$_2$-3-Cl | CH$_3$ | NCH$_3$ | |

TABLE 14

( Het  = Q$^{14}$, R$^1$ = R$^2$ = H)

| No | R$^3$ | X | (R$^9$)$_n$ | mp ° C. |
|---|---|---|---|---|
| 1305 | C$_2$H$_5$ | 2,6-(C$_2$H$_5$)$_2$-3-Cl | H | 218–220 |
| 1306 | n-C$_3$H$_7$ | 2,6-(C$_2$H$_5$)$_2$-3-Cl | H | 184–186 |
| 1307 | i-C$_3$H$_7$ | 2,6-(C$_2$H$_5$)$_2$-3-Cl | H | |
| 1308 | c-C$_3$H$_5$ | 2,6-(C$_2$H$_5$)$_2$-3-Cl | H | |

TABLE 14-continued ( Het )$= Q^{14}, R^1 = R^2 = H$)

| No | R³ | X | (R⁹)ₙ | mp ° C. |
|---|---|---|---|---|
| 1309 | n-C₄H₉ | 2,6-(C₂H₅)₂-3-Cl | H | |
| 1310 | s-C₄H₉ | 2,6-(C₂H₅)₂-3-Cl | H | |
| 1311 | i-C₄H₉ | 2,6-(C₂H₅)₂-3-Cl | H | 148–150 |
| 1312 | t-C₄H₉ | 2,6-(C₂H₅)₂-3-Cl | H | |
| 1313 | n-C₅H₁₁ | 2,6-(C₂H₅)₂-3-Cl | H | |
| 1314 | neo-C₅H₁₁ | 2,6-(C₂H₅)₂-3-Cl | H | 208–210 |
| 1315 | c-C₅H₉ | 2,6-(C₂H₅)₂-3-Cl | H | 174–176 |
| 1316 | t-C₅H₁₁ | 2,6-(C₂H₅)₂-3-Cl | H | |
| 1317 | C₂H₅ | 2-CH₃-3-Cl | H | |
| 1318 | n-C₃H₇ | 2-CH₃-3-Cl | H | 204–206 |
| 1319 | i-C₃H₇ | 2-CH₃-3-Cl | H | |
| 1320 | c-C₃H₅ | 2-CH₃-3-Cl | H | |
| 1321 | n-C₄H₉ | 2-CH₃-3-Cl | H | |
| 1322 | s-C₄H₉ | 2-CH₃-3-Cl | H | |
| 1323 | i-C₄H₉ | 2-CH₃-3-Cl | H | |
| 1324 | t-C₄H₉ | 2-CH₃-3-Cl | H | |
| 1325 | n-C₅H₁₁ | 2-CH₃-3-Cl | H | |
| 1326 | neo-C₅H₁₁ | 2-CH₃-3-Cl | H | |
| 1327 | c-C₅H₉ | 2-CH₃-3-Cl | H | 218–220 |
| 1328 | t-C₅H₁₁ | 2-CH₃-3-Cl | H | |
| 1329 | C₂H₅ | 2,6-(C₂H₅)₂-3-Cl | 6-CH₃ | |
| 1330 | n-C₃H₇ | 2,6-(C₂H₅)₂-3-Cl | 6-CH₃ | |
| 1331 | i-C₃H₇ | 2,6-(C₂H₅)₂-3-Cl | 6-CH₃ | |
| 1332 | c-C₃H₅ | 2,6-(C₂H₅)₂-3-Cl | 6-CH₃ | |
| 1333 | n-C₄H₉ | 2,6-(C₂H₅)₂-3-Cl | 6-CH₃ | |
| 1334 | s-C₄H₉ | 2,6-(C₂H₅)₂-3-Cl | 6-CH₃ | |
| 1335 | i-C₄H₉ | 2,6-(C₂H₅)₂-3-Cl | 6-CH₃ | |
| 1336 | t-C₄H₉ | 2,6-(C₂H₅)₂-3-Cl | 6-CH₃ | |
| 1337 | n-C₅H₁₁ | 2,6-(C₂H₅)₂-3-Cl | 6-CH₃ | |
| 1338 | neo-C₅H₁₁ | 2,6-(C₂H₅)₂-3-Cl | 6-CH₃ | |
| 1339 | c-C₅H₉ | 2,6-(C₂H₅)₂-3-Cl | 6-CH₃ | |
| 1340 | t-C₅H₁₁ | 2,6-(C₂H₅)₂-3-Cl | 6-CH₃ | |
| 1341 | C₂H₅ | 2,6-(C₂H₅)₂-3-Cl | 6-Cl | |
| 1342 | n-C₃H₇ | 2,6-(C₂H₅)₂-3-Cl | 6-Cl | |
| 1343 | i-C₃H₇ | 2,6-(C₂H₅)₂-3-Cl | 6-Cl | |
| 1344 | c-C₃H₅ | 2,6-(C₂H₅)₂-3-Cl | 6-Cl | |
| 1345 | n-C₄H₉ | 2,6-(C₂H₅)₂-3-Cl | 6-Cl | |
| 1346 | s-C₄H₉ | 2,6-(C₂H₅)₂-3-Cl | 6-Cl | |
| 1347 | i-C₄H₉ | 2,6-(C₂H₅)₂-3-Cl | 6-Cl | |
| 1348 | t-C₄H₉ | 2,6-(C₂H₅)₂-3-Cl | 6-Cl | |
| 1349 | n-C₅H₁₁ | 2,6-(C₂H₅)₂-3-Cl | 6-Cl | |
| 1350 | neo-C₅H₁₁ | 2,6-(C₂H₅)₂-3-Cl | 6-Cl | |
| 1351 | c-C₅H₉ | 2,6-(C₂H₅)₂-3-Cl | 6-Cl | |
| 1352 | t-C₅H₁₁ | 2,6-(C₂H₅)₂-3-Cl | 6-Cl | |

Herbicides comprising, as an active ingredient thereof, the fused heterocyclic dicarboxylic acid diamide derivative represented by general formula (I) or a salt thereof are useful for controlling annual and perennial weeds which grow in paddy fields, upland fields, orchards, swamps, etc., such as barnyard grass (*Echinochloa crus-galli Beauv.*, an annual gramineous weed which is an injurious weed of paddy fields), umbrella plant (*Cyperus difformis L.*, an annual cyperaceous grass which is an injurious weed of paddy fields), slender spikerush (*Eleocharis acicularis Roem.* et Schult, a perennial cyperaceous grass which is an injurious weed of paddy fields and which grows also in swamps and waterways), arrowhead (*Saquittaria pygmaea Miq.*, an injurious perennial weed of Alismataceae family which grows in paddy fields, swamps and ditches), bulrush (*Scirpus juncoides Roxb.* var. *horarui ohwi*, a perennial cyperaceous weed which grows in paddy fields, swamps and ditches), foxtail grass (*Alopecurus aegualis* var. *amurensis Ohwi*, gramineous grass which grows in paddy fields and low swamps), wild oats (*Avena fatua L.*, a biennial gramineous grass which grows in plains, waste lands and upland fields), mugwort (*Artemisia princeps Pamp.*, a perennial composite grass which grows in cultivated and uncultivated fields and mountains), large crabgrass (*Digitaria adscenducus Henr.*, an annual gramineous grass which is a strongly injurious weed of upland fields and orchards), Gishigishi or Japanese dock (*Rumex japonicus Houtt.*, a perennial polygonaceous weed which grows in upland fields and roadsides), umbrella sedge (*Cyperus iria L.*, an annual cyperaceous weed), redroot pigweed (*Amaranthus varidis L.*, an annual weed of Amaranthaceae family which grows in vacant lands, roadsides and upland fields), cocklebur (*Xanthium strumarium L.*, an injurious annual composite weed which grows in upland fields), velvetleaf (*Abutilon theophrasti L.*, an injurious annual weed of Malvaceae family which grows in upland fields), purple thornapple (*Dutura tatula L.*, an annual injurious weed of Convolvulaceae family which grows in upland fields), bird's eye speedwell (*Veronica persica Poir.*, an injurious biennual weed of Scrophulariaceae family which grows in upland fields) and cleavers (*Galium aparine L.*, an injurious annual weed of Rubiaceae family which grows in upland fields and orchards), and especially useful for controlling weeds such as barnyard grass and bulrush in paddy fields.

Since the herbicides comprising, as an active ingredient thereof, the fused heterocyclic dicarboxylic acid diamide derivative represented by general formula (I) or a salt thereof exhibit an excellent controlling effect on weeds before or after emergence, the characteristic physiological activities of the herbicides can be effectively manifested by treating fields with the herbicides before planting useful plants therein, or after planting useful plants therein (including the case in which useful plants are already planted as in orchards) but during the period from the initial stage of emergence of weeds to their growth stage.

However, the application of the herbicides of the present invention is not restricted only to the modes mentioned above. The herbicides of the present invention can be applied to control not only weeds which grow in paddy fields but also weeds which grow in other places such as fields after reaping, temporarily non-cultivated paddy fields and upland fields, ridges between fields, agricultural pathways, waterways, lands constructed for pasture, graveyards, parks, roads, playgrounds, unoccupied areas around buildings, developed lands, railways, forests and the like.

The treatment of target weeds with the herbicides is most effective in economy when the treatment is carried out not later than the initial stage of emergence of weeds. However, the time of application is not limited thereto, but it is also possible to control the weeds in the growth stage.

When the fused heterocyclic dicarboxylic acid diamide derivative of general formula (I) or a salt thereof is used a herbicide, the compound is usually formed into a preparation of convenient form according to the conventional method in the production of agricultural compositions.

The fused heterocyclic dicarboxylic acid diamide derivatives of general formula (I) or salt thereof according to the present invention are compounded together with adjuvants according to the need, then supported on an appropriate carrier by the procedure of dissolution, separation, suspension, mixing, impregnation, adsorption or adhesion, and then formed into appropriate preparation form such as suspension, emulsifiable concentrate, soluble concentrate, wettable powder, granules, dust, tablet or the like, after which they are put to use.

The inert carrier used in the present invention may be any of a solid carrier and a liquid carrier. The materials which can constitute the solid carrier include, for example, soybean flour, cereal flour, wood flour, bark flour, saw dust, powdered tobacco stalks, powdered walnut shells, bran, powdered cellulose, extraction residues of vegetables, powdered synthetic polymers or resins, clay (e.g. kaolin, bentonite and acid clay), talc (e.g. talc and pyrophyllite), silica materials (e.g. diatomaceous earth, siliceous sand, mica, white carbon, i.e. synthetic high-dispersion silicic acid, also called finely divided hydrated silica or hydrated silicic acid, some of the commercially available products contain calcium silicate as the major component), activated carbon, powdered sulfur, pumice, calcined diatomaceous earth, ground brick, fly ash, sand, calcium carbonate, calcium phosphate and other inorganic or mineral powders, chemical fertilizers such as ammonium sulfate, ammonium phosphate, ammonium nitrate, urea, ammonium chloride and the like, and compost. These carriers may be used either alone or as a mixture of two or more carriers.

The liquid carrier is that which itself has a solubility or which is without such solubility but is capable of dispersing an active ingredient with the aid of an adjuvant. The following are typical examples of the liquid carrier, which can be used alone or as a mixture thereof. Water; alcohols such as methanol, ethanol, isopropanol, butanol and ethylene glycol; ketones such as acetone, methyl ethyl ketone, methyl isobutyl ketone, diisobutyl ketone and cyclohexanone; ethers such as ethyl ether, dioxane, cellosolve, dipropyl ether and tetrahydrofuran; aliphatic hydrocarbons such as kerosene and mineral oil; aromatic hydrocarbons such as benzene, toluene, xylene, solvent naphtha and alkylnaphthalene; halogenated hydrocarbons such as dichlorethane, chloroform and carbon tetrachloride; esters such as ethyl acetate, diisopropyl phthalate, dibutyl phthalate and dioctyl phthalate; amides such as dimethylformamide, diethylformamide and dimethylacetamide; nitriles such as acetonitrile; and dimethyl sulfoxide.

The following are typical examples of the adjuvant, which are used depending upon purposes and used alone or in combination of two or more adjuvants in some cases, or need not to be used at all.

To emulsify, disperse, dissolve and/or wet an active ingredient, a surfactant is used. As the surfactant, there can be exemplified polyoxyethylene alkyl ethers, polyoxyethylene alkylaryl ethers, polyoxyethylene higher fatty acid esters, polyoxyethylene resinates, polyoxyethylene sorbitan monolaurate, polyoxyethylene sorbitan monooleate, alkylarylsulfonates, naphthalene-sulfonic acid condensation products, ligninsulfonates and higher alcohol sulfate esters.

Further, to stabilize the dispersion of an active ingredient, tackify it and/or bind it, there may be used adjuvants such as casein, gelatin, starch, methyl cellulose, carboxymethyl cellulose, gum arabic, polyvinyl alcohols, turpentine, bran oil, bentonite and ligninsulfonates.

To improve the flowability of a solid product, there may be used adjuvants such as waxes, stearates and alkyl phosphates.

Adjuvants such as naphthalenesulfonic acid condensation products and polycondensates of phosphates may be used as a peptizer for dispersible products.

Adjuvants such as silicone oil may also be used as a defoaming agent.

The content of the active ingredient may be varied according to the need. In dusts or granules, the suitable content thereof is from 0.01 to 50% by weight. In emulsifiable concentrate and flowable wettable powder, too, the suitable content is from 0.01 to 50% by weight.

The herbicide of the present invention comprising the fused heterocyclic dicarboxylic acid diamide derivative represented by general formula (I) or a salt thereof as an active ingredient is used to kill a variety of weeds or to suppress their growth in the following manner. That is, it is applied to weeds or foliage or soil in a place in which generation or growth of objective weed is undesirable either directly or after being properly diluted with or suspended in water or the like, in an amount effective for control of the weeds.

The applying dosage of the herbicide of the present invention comprising the fused heterocyclic dicarboxylic acid diamide derivative of general formula (I) or a salt thereof is varied depending upon various factors such as a purpose, weed to be controlled, a growth state of a plant, tendency of generation of weed, weather, environmental conditions, a preparation form, an application method, an application site and an application time. It may be properly chosen in a range of 0.1 g to 10 kg (in terms of active ingredient compound) per hectare depending upon purpose.

The herbicide of the present invention comprising the fused heterocyclic dicarboxylic acid diamide of general formula (I) or a salt thereof as active ingredient may be used in admixture with other herbicides in order to expand both spectrum of controllable weeds and the period of time when effective applications are possible or to reduce the dosage.

EXAMPLES

Next, typical examples of the present invention and referential examples are presented below. The present invention is by no means limited by these examples. Example 1

1–1. Production of 3-(3-Chloro-2,6-diethylphenyl)-aminocarbonyl-7-fluoro-2-quinolinecarboxylic Acid n-Propylamide (Compound No. 158)

In 10 ml of tetrahydrofuran was dissolved 800 mg (2.41 mmol) of N-(3-chloro-2,6-diethylphenyl)-7-fluoro-2,3-quinolinedicarboximide. After adding 150 mg (2.5 mmol) of n-propylamine to the solution obtained above, a reaction was carried out for 12 hours.

After completion of the reaction, the reaction mixture was concentrated under reduced pressure, and the residue thus obtained was purified by silica gel column chromatography using ethyl acetate/n-hexane as an eluent. Thus, 820 mg of the objective compound was obtained as a white crystalline product.

Property: m.p. 220–222° C.; Yield: 87%

1–2. Production of 3-(3-Chloro-2,6-diethylphenyl)-aminocarbonyl-1,8-naphthylidine-2-carboxylic Acid Ethylamide (Compound No. 360)

In 10 ml of dioxane was dissolved 700 mg (1.91 mmol) of 2,3-carboximide. After adding 95 mg (2.3 mmol) of ethylamine to the solution obtained above, a reaction was carried out for 12 hours.

After completion of the reaction, the reaction mixture was concentrated under reduced pressure, and the residue thus obtained was purified by silica gel column chromatography using ethyl acetate/n-hexane as an eluent. Thus, 620 mg of the objective compound was obtained as a white crystalline product.

1-3. Production of 3-(3-Chloro-2,6-diethylphenyl)-aminocarbonyl-7,8-dihydro-5H-pyrano[4,3-b]pyridine-2-carboxylic Acid n-Propylamide (Compound No. 462)

In 10 ml of dioxane was dissolved 770 mg (2.08 mmol) of N-(3-chloro-2,6-diethylphenyl)-7,8-dihydro-5H-pyrano[4,3-b]pyridine-2,3-carboximide. After adding 127 mg (2.3 mmol) of n-propylamine to the solution obtained above, a reaction was carried out for 12 hours.

After completion of the reaction, the reaction mixture was concentrated under reduced pressure, and the residue thus obtained was purified by silica gel column chromatography using ethyl acetate/n-hexane as an eluent. Thus, 735 mg of the objective compound was obtained as a white crystalline product.

Property: m.p. 166–170° C.; Yield: 83%

Example 2

2-1. Production of 6-(3-Chloro-2,6-diethylphenyl)-aminocarbonyl-2,3-dihydro-1-oxo-thieno[2,3-b]pyridine-5-carboxylic Acid n-Propylamide (Compound No. 1028)

In 10 ml of chloroform was dissolved 500 mg (1.16 =mol) of 6-(3-chloro-2,6-diethylphenyl)aminocarbonyl-2,3-dihydrothieno[2,3-b]pyridine-5-carboxylic acid n-propylamide. After adding 200 mg (1.1 mmol) of m-chloroperbenzoic acid to the solution obtained above at 0° C., a reaction was carried out at ambient temperature for 6 hours.

After completion of the reaction, the reaction mixture was washed successively with a saturated aqueous solution of sodium hydrogen carbonate and a saturated aqueous solution of sodium chloride and dried over anhydrous magnesium sulfate. The solvent was distilled off under reduced pressure, and the residue thus obtained was purified by silica gel column chromatography using ethyl acetate/n-hexane as an eluent, whereby 400 mg of the objective compound was obtained as a white crystalline product.

Property: m.p. 230–233° C.; Yield: 77%

2-2. Production of 6-(3-Chloro- 2,6-diethylphenyl)-aminocarbonyl-2,3-dihydro-1,1-dioxo-thieno[2,3-b]pyridine-5-carboxylic Acid n-Propylamide (Compound No. 1040)

In 10 ml of chloroform was dissolved 500 mg (1.16 mmol) of 6-(3-chloro-2,6-diethylphenyl)-aminocarbonyl-2,3-dihydrothieno[2,3-b]pyridine-5-carboxylic acid n-propylamide. After adding 400 mg (2.2 mmol) of m-chloroperbenzoic acid to the solution obtained above at 0° C., a reaction was carried out at ambient temperature for 6 hours.

After completion of the reaction, the reaction mixture was washed successively with a saturated aqueous solution of sodium hydrogen carbonate and a saturated aqueous solution of sodium chloride and dried over anhydrous magnesium sulfate. The solvent was distilled off under reduced pressure, and the residue thus obtained was purified by silica gel column chromatography using ethyl acetate/n-hexane as an eluent, whereby 450 mg of the objective compound was obtained as a white crystalline product.

Property: m.p. 198–200° C.; Yield: 84%.

Referential Example 1

Production of 6-(3-Chloro-2,6-diethylphenyl) aminocarbonyl-1-methyl-pyrazolo[5,4-b]pyridine-5-carboxylic Acid In 100 ml of tetrahydrofuran was dissolved 8.0 g (39.4 mmol) of 1-methyl-pyrazolo[5,4-b]pyridine-5,6-dicarboxylic acid anhydride. After adding 7.23 g (39.4 mmol) of 3-chloro-2,6-diethylaniline to the solution obtained above, a reaction was carried out at ambient temperature for 12 hours.

After completion of the reaction, the reaction mixture was concentrated under reduced pressure, and the deposited crystal was washed with a small quantity of ether. Thus, 12.0 g (yield 79%) of the objective compound was obtained.

$^1$-H-NMR[TMS/CDCl$_3$, δ (ppm)]; 1.21(3H,t,J=7.5 Hz), 1.26(3H,t,J=7.5 Hz), 2.63(2H,q,J=7.5 Hz), 2.83(2H,q,J=7.5 Hz), 4.27(3H,s), 7.18(1H,d,J=8.4 Hz), 7.41(1H,d,J=8.4 Hz), 8.30(1H,s), 9.43(1H,s), 10.10 (1H,bs).

Referential Example 2

Production of N-(3-Chloro-2,6-diethylphenyl) aminocarbonyl-1-methyl-pyrazolo[5,4-b]pyridine-5,6-carboximide In 30 ml of trifluoroacetic acid was dissolved 9.0 g (23.3 mmol) of 6-(3-chloro-2,6-diethylphenyl)aminocarbonyl-1-methyl-pyrazolo[5,4-b]pyridine-5-carboxylic acid. After adding 4.90 g (23.3 mmol) of trifluoroacetic acid anhydride to the solution obtained above, a reaction was carried out under reflux for 4 hours.

After completion of the reaction, the reaction mixture was concentrated under reduced pressure, and the residue thus obtained was purified by silica gel column chromatography using ethyl acetate/n-hexane as an eluent. Thus, 8.0 g (yield 93%) of the objective compound was obtained.

$^1$H-NMR[(TMS/CDCl$_3$, δ (ppm)]; 1.09(3H,t,J=7.5 Hz), 1.13(3H,t,J=7.5 Hz), 2.43(2H,q,J=7.5 Hz), 2.62(2H,q,J=7.5 Hz), 4.34(3H,s), 7.20(1H,d,J=8.4 Hz), 7.47(1H,d,J=8.4 Hz), 8.35(1H,s), 8.67(1H,s)

Referential Example 3

Production of N-(3-Chloro-2,6-diethylphenyl) aminocarbonyl-1-methyl-pyrazolo[4,5-b]pyridine-5,6-carboximide In 30 ml of trifluoroacetic acid was dissolved 7.5 g (19.4 mmol) of 5-(3-chloro-2,6-diethylphenyl)aminocarbonyl-1-methyl-pyrazolo[4,5-b]pyridine-6-carboxylic acid. After adding 4.08 g (19.4 mmol) of trifluoroacetic acid anhydride to the solution obtained above, a reaction was carried out under reflux for 4 hours.

After completion of the reaction, the reaction mixture was concentrated under reduced pressure, and the residue thus obtained was purified by silica gel column chromatography using ethyl acetate/n-hexane as an eluent. Thus, 6.5 g (yield 91%) of the objective compound was obtained.

$^1$H-NMR[TMS/CDCl$_3$, δ (ppm)]; 1.08(3H,t,J=7.5 Hz), 1.12(3H,t,J=7.5 Hz), 2.43(2H,q,J=7.5 Hz), 2.63(2H,q,J=7.5 Hz), 4.27(3H,s), 7.20(1H,d,J=8.4 Hz), 7.48(1H,d,J=8.4 Hz), 8.37(1H,s), 8.53(1H,s)

Next, typical preparation examples and test examples of the present invention are shown below. The present invention is by no means limited to these examples.

In the preparation examples, the term "part" means part by weight.

Preparation Example 1

| | |
|---|---|
| Each compound listed in Tables 1 to 14 | 50 parts |
| Xylene | 40 parts |
| Mixture of polyoxyethylene nonylphenyl ether and calcium alkylbenzenesulfonate | 10 parts |

An emulsifiable concentrate was prepared by mixing uniformly the above ingredients to effect dissolution.

Preparation Example 2

| | |
|---|---|
| Each compound listed in Tables 1 to 14 | 3 parts |
| Clay powder | 82 parts |
| Diatomaceous earth powder | 15 parts |

A dust was prepared by mixing uniformly and grinding the above ingredients.

Preparation Example 3

| | |
|---|---|
| Each compound listed in Tables 1 to 14 | 5 parts |
| Mixed powder of bentonite and clay | 90 parts |
| Calcium ligninsulfonate | 5 parts |

Granules were prepared by mixing the above ingredients uniformly, and kneading the resulting mixture together with a suitable amount of water, followed by granulation and drying.

Preparation Example 4

| | |
|---|---|
| Each compound listed in Tables 1 to 14 | 20 parts |
| Mixture of kaolin and synthetic high-dispersion silicic acid | 75 parts |
| Mixture of polyoxyethylene nonylphenyl ether and calcium alkylbenzenesulfonate | 5 parts |

A wettable powder was prepared by mixing uniformly and grinding the above ingredients.

Test Example 1

Test for Herbicidal Effect on Paddy Field Weeds Before Emergence

Soil was filled into 1/10000 are pots and brought into a state of paddy field, in which seeds of barnyard grass (*Echinochloa crus-galli Beauv.*) and bulrush (*Scirpus juncoides Roxb.*) were made to be before germination. The soil in the pots were treated with a solution containing a predetermined dosage of a chemical agent comprising a compound of the present invention listed in Tables 1 to 14.

Twenty one days after the treatment, the herbicidal effect was investigated, the result was compared with that in untreated plot to calculate the weed-controlling rate, and the herbicidal effect was judged according to the following criterion:

5—Weed-killing rate is 100%.
4—Weed-killing rate is 90–99%.
3—Weed-killing rate is 70–89%.
2—Weed-killing rate is 40–69%.
1—Weed-killing rate is 1–39%.
0—Weed-killing rate is 0%.

The results are shown in Table 15.

Test Example 2

Test for Herbicidal Effect on Paddy Field Weeds After Emergence.

Soil was filled into 1/10000 are pots and brought into a state of paddy field, in which seeds of barnyard grass (*Echinochloa crus-galli Beauv.*), bulrush (*Scirpus juncoides Roxb.*) and monochoria (*Monochoria vaginalis Presl*) were made to reach one-leaved stage. The soil in the pots were treated with a solution containing a predetermined dosage of a chemical agent comprising a compound of the present invention listed in Tables 1 to 14.

Twenty one days after the treatment, the herbicidal effect was investigated and the result was compared with that in untreated plot to calculate the weed-controlling rate, and the herbicidal effect was judged according to the same criterion as in Test Example 1.

The results are shown in Table 15.

TABLE 15

| No. | Dosage (kg/ha) | Pre-emergence treatment | | Post-emergence treatment | | |
|---|---|---|---|---|---|---|
| | | Barnyard grass | Bulrush | Barnyard grass | Bulrush | Monochoria |
| 1 | 5 | 5 | 5 | 4 | 4 | 5 |
| 2 | 5 | 5 | 5 | 4 | 4 | 5 |
| 3 | 5 | 5 | 5 | 4 | 4 | 5 |
| 28 | 5 | 3 | 3 | 3 | 3 | 4 |
| 29 | 5 | 4 | 3 | 3 | 3 | 4 |
| 30 | 5 | 5 | 4 | 3 | 3 | 5 |
| 43 | 5 | 4 | 2 | 3 | 2 | 4 |
| 44 | 5 | 4 | 3 | 3 | 2 | 4 |
| 53 | 5 | 5 | 2 | 3 | 2 | 4 |
| 58 | 5 | 4 | 3 | 3 | 3 | 4 |
| 71 | 5 | 5 | 5 | 3 | 3 | 5 |
| 97 | 5 | 3 | 1 | 2 | 1 | 3 |
| 99 | 5 | 5 | 5 | 5 | 5 | 5 |
| 100 | 5 | 5 | 5 | 5 | 5 | 5 |
| 101 | 5 | 5 | 5 | 5 | 5 | 5 |
| 126 | 5 | 3 | 2 | 2 | 1 | 3 |
| 127 | 5 | 4 | 3 | 4 | 4 | 5 |
| 128 | 5 | 5 | 5 | 5 | 5 | 5 |
| 129 | 5 | 5 | 5 | 5 | 5 | 5 |
| 130 | 5 | 5 | 5 | 5 | 5 | 5 |
| 157 | 5 | 5 | 5 | 5 | 5 | 5 |
| 158 | 5 | 5 | 5 | 5 | 5 | 5 |
| 189 | 5 | 5 | 4 | 4 | 3 | 5 |
| 200 | 5 | 4 | 2 | 3 | 1 | 3 |
| 201 | 5 | 3 | 2 | 3 | 1 | 3 |
| 219 | 5 | 5 | 5 | 4 | 4 | 5 |
| 224 | 5 | 5 | 3 | 3 | 2 | 3 |
| 228 | 5 | 5 | 4 | 3 | 2 | 4 |
| 234 | 5 | 5 | 2 | 3 | 2 | 4 |
| 243 | 5 | 3 | 1 | 3 | 1 | 3 |
| 246 | 5 | 4 | 1 | 2 | 1 | 3 |
| 275 | 5 | 5 | 5 | 5 | 4 | 5 |
| 276 | 5 | 5 | 5 | 3 | 4 | 5 |
| 289 | 5 | 5 | 5 | 5 | 4 | 5 |
| 290 | 5 | 5 | 5 | 5 | 5 | 5 |
| 291 | 5 | 5 | 4 | 5 | 4 | 5 |
| 305 | 5 | 5 | 4 | 4 | 3 | 5 |
| 310 | 5 | 4 | 3 | 3 | 2 | 5 |
| 334 | 5 | 5 | 4 | 4 | 4 | 5 |
| 339 | 5 | 4 | 3 | 3 | 2 | 4 |
| 343 | 5 | 5 | 3 | 3 | 3 | 5 |

TABLE 15-continued

| No. | Dosage (kg/ha) | Pre-emergence treatment | | Post-emergence treatment | | |
|---|---|---|---|---|---|---|
| | | Barnyard grass | Bulrush | Barnyard grass | Bulrush | Monochoria |
| 359-1 | 5 | 5 | 5 | 5 | 5 | 5 |
| 359-2 | 5 | 5 | 5 | 5 | 5 | 5 |
| 359-3 | 5 | 5 | 5 | 5 | 5 | 5 |
| 359-4 | 5 | 5 | 5 | 5 | 5 | 5 |
| 359-5 | 5 | 5 | 5 | 5 | 5 | 5 |
| 359-6 | 5 | 5 | 5 | 5 | 5 | 5 |
| 360 | 5 | 5 | 5 | 5 | 5 | 5 |
| 361 | 5 | 5 | 5 | 5 | 5 | 5 |
| 375 | 5 | 5 | 5 | 5 | 5 | 5 |
| 388 | 5 | 5 | 5 | 5 | 5 | 5 |
| 414 | 5 | 5 | 5 | 5 | 5 | 5 |
| 423 | 5 | 5 | 5 | 5 | 5 | 5 |
| 431 | 5 | 5 | 5 | 5 | 5 | 5 |
| 438 | 5 | 5 | 5 | 5 | 5 | 5 |
| 447 | 5 | 5 | 5 | 5 | 5 | 5 |
| 450 | 5 | 5 | 5 | 5 | 5 | 5 |
| 462 | 5 | 5 | 5 | 5 | 5 | 5 |
| 474 | 5 | 5 | 5 | 5 | 5 | 5 |
| 486 | 5 | 5 | 5 | 5 | 5 | 5 |
| 498 | 5 | 5 | 5 | 5 | 5 | 5 |
| 510 | 5 | 5 | 5 | 5 | 5 | 5 |
| 519 | 5 | 5 | 5 | 5 | 5 | 5 |
| 527 | 5 | 5 | 5 | 5 | 5 | 5 |
| 534 | 5 | 5 | 5 | 5 | 5 | 5 |
| 558 | 5 | 5 | 5 | 5 | 5 | 5 |
| 570 | 5 | 5 | 5 | 5 | 5 | 5 |
| 582 | 5 | 5 | 5 | 5 | 5 | 5 |
| 606 | 5 | 5 | 5 | 5 | 5 | 5 |
| 630 | 5 | 5 | 5 | 5 | 5 | 5 |
| 654 | 5 | 5 | 5 | 3 | 3 | 1 | 4 |
| 678 | 5 | 5 | 5 | 5 | 5 | 5 |
| 679 | 5 | 5 | 5 | 5 | 5 | 5 |
| 703 | 5 | 5 | 5 | 5 | 5 | 5 |
| 724 | 5 | 5 | 5 | 5 | 5 | 5 |
| 727 | 5 | 5 | 5 | 5 | 5 | 5 |
| 739 | 5 | 5 | 5 | 5 | 5 | 5 |
| 760 | 5 | 5 | 5 | 5 | 5 | 5 |
| 763 | 5 | 5 | 4 | 3 | 4 | 3 | 5 |
| 774 | 5 | 5 | 5 | 5 | 5 | 5 |
| 775 | 5 | 5 | 5 | 5 | 5 | 5 |
| 796 | 5 | 5 | 5 | 5 | 5 | 5 |
| 798 | 5 | 5 | 5 | 5 | 5 | 5 |
| 799 | 5 | 5 | 5 | 5 | 5 | 5 |
| 811 | 5 | 5 | 5 | 5 | 5 | 5 |
| 814 | 5 | 5 | 5 | 5 | 5 | 5 |
| 824 | 5 | 5 | 5 | 5 | 5 | 5 |
| 836 | 5 | 5 | 5 | 5 | 5 | 5 |
| 847 | 5 | 5 | 5 | 5 | 5 | 5 |
| 870 | 5 | 5 | 5 | 5 | 5 | 5 |
| 871 | 5 | 5 | 5 | 5 | 5 | 5 |
| 892 | 5 | 5 | 5 | 5 | 5 | 5 |
| 894 | 5 | 5 | 5 | 5 | 5 | 5 |
| 895 | 5 | 5 | 5 | 5 | 5 | 5 |
| 907 | 5 | 5 | 5 | 5 | 5 | 5 |
| 919 | 5 | 5 | 5 | 5 | 5 | 5 |
| 934 | 5 | 5 | 5 | 5 | 5 | 5 |
| 943 | 5 | 5 | 5 | 5 | 5 | 5 |
| 955 | 5 | 5 | 5 | 5 | 5 | 5 |
| 976 | 5 | 5 | 5 | 5 | 5 | 5 |
| 980 | 5 | 5 | 5 | 5 | 5 | 5 |
| 992 | 5 | 5 | 5 | 5 | 5 | 5 |
| 1016 | 5 | 5 | 5 | 5 | 5 | 5 |
| 1028 | 5 | 5 | 5 | 5 | 5 | 5 |
| 1040 | 5 | 5 | 5 | 5 | 5 | 5 |
| 1052 | 5 | 5 | 5 | 5 | 5 | 5 |
| 1064 | 5 | 5 | 5 | 5 | 5 | 5 |
| 1085 | 5 | 5 | 5 | 5 | 5 | 5 |
| 1087 | 5 | 5 | 5 | 5 | 5 | 5 |
| 1088 | 5 | 5 | 5 | 5 | 5 | 5 |
| 1112 | 5 | 5 | 5 | 5 | 5 | 5 |
| 1124 | 5 | 5 | 5 | 5 | 5 | 5 |
| 1136 | 5 | 5 | 5 | 5 | 5 | 5 |
| 1148 | 5 | 5 | 5 | 5 | 5 | 5 |
| 1160 | 5 | 5 | 5 | 5 | 5 | 5 |
| 1171 | 5 | 5 | 5 | 5 | 5 | 5 |
| 1173 | 5 | 5 | 5 | 5 | 5 | 5 |
| 1197 | 5 | 5 | 5 | 5 | 5 | 5 |
| 1209 | 5 | 5 | 5 | 5 | 5 | 5 |
| 1233 | 5 | 5 | 5 | 5 | 5 | 5 |
| 1245 | 5 | 5 | 5 | 5 | 5 | 5 |
| 1269 | 5 | 5 | 5 | 5 | 5 | 5 |
| 1294 | 5 | 5 | 5 | 5 | 5 | 5 |
| 1305 | 5 | 5 | 5 | 5 | 5 | 5 |
| 1306 | 5 | 5 | 5 | 5 | 5 | 5 |
| 1311 | 5 | 5 | 5 | 5 | 5 | 5 |
| 1314 | 5 | 5 | 5 | 4 | 4 | 5 |
| 1315 | 5 | 5 | 5 | 5 | 5 | 5 |
| 1318 | 5 | 5 | 4 | 4 | 4 | 5 |
| 1327 | 5 | 5 | 4 | 4 | 4 | 5 |

Test Example 3

Herbicidal Effect on Upland Weeds Before Emergence

Polyethylene-made vats having a size of 10 cm (length)× 20 cm (width)×5 cm (height) were filled with soil, sown with seeds of forxtail grass (*Alopecurus aequalis* var. *amurensis Ohwi*); abbreviated to *Am*), barnyard grass (*Echinochloa crus-galli Beauv.*, abbreviated to *Ec*), velvetleaf (*Abutilon theophtasti L.*, abbreviated to *At*), cocklebur (*Xanthium strumarium L.*, abbreviated to *Xs*), cleavers (*Galium aparine L.*, abbreviated to *Ga*) and bird's eye speedwell (*Veronica persica Poir.*, abbreviated to *Vp*) and with seeds of wheat (abbreviated to Wh) and soybean plant (So) as upland crop plants, and then covered with soil. Then, a liquid preparation of an agent comprising a prescribed concentration of a compound of the present invention (the compounds listed in Tables 1–14) as active ingredient was sprayed.

Fourteen days after the treatment, the herbicidal effect was investigated, from which weed-killing rate was calculated in the same manner as in Test Example 1, and the herbicidal effect was judged.

At the same time, phytotoxicity to soybean plant and wheat was investigated and judged according to the criterion mentioned below. Criterion for judgment of phytotoxicity:

5—Crop-killing rate is 100%.

4—Crop-killing rate is 90–99%.

3—Crop-killing rate is 70–89%.

2—Crop-killing rate is 40–69%.

1—Crop-killing rate is 1–39%.

0—Crop-killing rate is 0–20% (No Phytotoxicity).

The results are summarized in Table 16.

TABLE 16

| No | Dosage (kg/ha) | Phytotoxicity | | Herbicidal effect | | | | | |
|---|---|---|---|---|---|---|---|---|---|
| | | Wh | So | Am | Ec | At | Xs | Ga | Vp |
| 1 | 5 | 3 | 1 | 4 | 5 | 5 | 5 | 4 | 5 |
| 2 | 5 | 3 | 1 | 5 | 5 | 5 | 5 | 5 | 5 |
| 3 | 5 | 2 | 1 | 5 | 5 | 5 | 5 | 5 | 5 |

TABLE 16-continued

| No | Dosage (kg/ha) | Phyto-toxicity Wh | So | Herbicidal effect Am | Ec | At | Xs | Ga | Vp |
|---|---|---|---|---|---|---|---|---|---|
| 28 | 5 | 1 | 0 | 4 | 3 | 4 | 3 | 3 | 4 |
| 29 | 5 | 4 | 1 | 4 | 4 | 5 | 4 | 4 | 5 |
| 30 | 5 | 3 | 1 | 5 | 5 | 5 | 4 | 4 | 5 |
| 43 | 5 | 1 | 0 | 4 | 3 | 4 | 3 | 3 | 4 |
| 44 | 5 | 1 | 0 | 4 | 3 | 4 | 2 | 4 | 4 |
| 53 | 5 | 1 | 0 | 4 | 4 | 4 | 2 | 3 | 4 |
| 58 | 5 | 2 | 1 | 4 | 4 | 5 | 4 | 4 | 5 |
| 71 | 5 | 4 | 0 | 4 | 4 | 5 | 3 | 4 | 5 |
| 97 | 5 | 1 | 0 | 3 | 2 | 3 | 1 | 1 | 3 |
| 99 | 5 | 1 | 2 | 4 | 5 | 5 | 5 | 5 | 5 |
| 100 | 5 | 1 | 3 | 4 | 5 | 5 | 5 | 4 | 5 |
| 101 | 5 | 2 | 2 | 4 | 5 | 5 | 4 | 4 | 5 |
| 126 | 5 | 1 | 0 | 3 | 3 | 3 | 2 | 2 | 3 |
| 127 | 5 | 1 | 1 | 3 | 4 | 3 | 2 | 2 | 4 |
| 128 | 5 | 2 | 1 | 4 | 4 | 4 | 3 | 4 | 5 |
| 129 | 5 | 3 | 1 | 5 | 5 | 5 | 5 | 5 | 5 |
| 130 | 5 | 0 | 0 | 4 | 5 | 5 | 4 | 5 | 5 |
| 157 | 5 | 3 | 1 | 4 | 5 | 5 | 4 | 4 | 5 |
| 158 | 5 | 4 | 1 | 4 | 5 | 5 | 4 | 5 | 5 |
| 189 | 5 | 2 | 0 | 3 | 4 | 4 | 3 | 3 | 4 |
| 200 | 5 | 0 | 0 | 3 | 3 | 3 | 2 | 2 | 3 |
| 201 | 5 | 0 | 0 | 3 | 2 | 3 | 2 | 2 | 3 |
| 219 | 5 | 2 | 1 | 4 | 5 | 5 | 3 | 4 | 5 |
| 224 | 5 | 1 | 0 | 3 | 4 | 4 | 3 | 3 | 4 |
| 228 | 5 | 0 | 0 | 3 | 3 | 4 | 2 | 2 | 4 |
| 234 | 5 | 0 | 0 | 3 | 3 | 3 | 2 | 2 | 3 |
| 243 | 5 | 0 | 0 | 2 | 3 | 3 | 2 | 2 | 3 |
| 246 | 5 | 1 | 0 | 3 | 4 | 4 | 3 | 3 | 4 |
| 275 | 5 | 1 | 0 | 3 | 4 | 4 | 3 | 3 | 4 |
| 276 | 5 | 2 | 0 | 4 | 5 | 5 | 4 | 4 | 5 |
| 289 | 5 | 2 | 1 | 4 | 5 | 5 | 3 | 4 | 5 |
| 290 | 5 | 2 | 1 | 5 | 5 | 5 | 4 | 5 | 5 |
| 291 | 5 | 1 | 0 | 4 | 5 | 5 | 4 | 5 | 5 |
| 305 | 5 | 2 | 0 | 4 | 5 | 4 | 3 | 3 | 4 |
| 310 | 5 | 2 | 0 | 4 | 4 | 4 | 3 | 3 | 4 |
| 334 | 5 | 2 | 0 | 4 | 4 | 5 | 3 | 3 | 4 |
| 339 | 5 | 1 | 0 | 4 | 4 | 4 | 2 | 3 | 4 |
| 343 | 5 | 0 | 0 | 3 | 4 | 3 | 2 | 3 | 4 |
| 359-1 | 5 | 0 | 0 | 5 | 5 | 5 | 5 | 5 | 5 |
| 359-2 | 5 | 0 | 1 | 5 | 5 | 5 | 5 | 5 | 5 |
| 359-3 | 5 | 0 | 0 | 5 | 5 | 5 | 5 | 5 | 5 |
| 359-4 | 5 | 0 | 2 | 5 | 5 | 5 | 5 | 5 | 5 |
| 359-5 | 5 | 0 | 0 | 5 | 5 | 5 | 5 | 5 | 5 |
| 359-6 | 5 | 0 | 0 | 5 | 5 | 5 | 5 | 5 | 5 |
| 360 | 5 | 4 | 3 | 5 | 5 | 5 | 5 | 5 | 5 |
| 361 | 5 | 4 | 4 | 5 | 5 | 5 | 5 | 5 | 5 |
| 375 | 5 | 3 | 3 | 5 | 5 | 5 | 5 | 5 | 5 |
| 388 | 5 | 5 | 4 | 5 | 5 | 5 | 5 | 5 | 5 |
| 414 | 5 | 5 | 4 | 5 | 5 | 5 | 5 | 5 | 5 |
| 423 | 5 | 5 | 4 | 5 | 5 | 5 | 5 | 5 | 5 |
| 431 | 5 | 3 | 3 | 4 | 5 | 5 | 4 | 4 | 5 |
| 438 | 5 | 5 | 5 | 5 | 5 | 5 | 5 | 5 | 5 |
| 447 | 5 | 5 | 4 | 5 | 5 | 5 | 5 | 5 | 5 |
| 450 | 5 | 4 | 4 | 5 | 5 | 5 | 4 | 4 | 5 |
| 462 | 5 | 5 | 5 | 5 | 5 | 5 | 5 | 5 | 5 |
| 474 | 5 | 4 | 3 | 5 | 5 | 5 | 4 | 5 | 5 |
| 486 | 5 | 4 | 4 | 5 | 5 | 5 | 5 | 5 | 5 |
| 498 | 5 | 4 | 4 | 5 | 5 | 5 | 4 | 4 | 5 |
| 510 | 5 | 5 | 4 | 5 | 5 | 5 | 5 | 5 | 5 |
| 519 | 5 | 5 | 4 | 5 | 5 | 5 | 5 | 5 | 5 |
| 527 | 5 | 5 | 5 | 5 | 5 | 5 | 4 | 5 | 5 |
| 534 | 5 | 4 | 3 | 5 | 5 | 5 | 5 | 5 | 5 |
| 558 | 5 | 5 | 5 | 5 | 5 | 5 | 5 | 5 | 5 |
| 570 | 5 | 4 | 4 | 5 | 5 | 5 | 5 | 5 | 5 |
| 582 | 5 | 4 | 4 | 5 | 5 | 5 | 5 | 5 | 5 |
| 606 | 5 | 4 | 3 | 5 | 5 | 5 | 4 | 4 | 5 |
| 630 | 5 | 4 | 3 | 5 | 5 | 5 | 4 | 4 | 5 |
| 654 | 5 | 3 | 1 | 4 | 4 | 5 | 3 | 3 | 4 |
| 678 | 5 | 4 | 2 | 4 | 5 | 5 | 3 | 3 | 5 |
| 679 | 5 | 4 | 2 | 5 | 5 | 5 | 4 | 4 | 5 |
| 703 | 5 | 4 | 2 | 4 | 5 | 5 | 4 | 4 | 5 |
| 724 | 5 | 4 | 3 | 4 | 4 | 4 | 3 | 4 | 5 |
| 727 | 5 | 4 | 4 | 5 | 5 | 5 | 4 | 4 | 5 |
| 739 | 5 | 5 | 4 | 5 | 5 | 5 | 5 | 5 | 5 |
| 760 | 5 | 4 | 3 | 5 | 5 | 5 | 4 | 5 | 5 |
| 763 | 5 | 4 | 3 | 4 | 5 | 5 | 4 | 4 | 5 |
| 774 | 5 | 5 | 4 | 5 | 5 | 5 | 5 | 5 | 5 |
| 775 | 5 | 5 | 5 | 5 | 5 | 5 | 5 | 5 | 5 |
| 796 | 5 | 5 | 4 | 5 | 5 | 5 | 4 | 5 | 5 |
| 798 | 5 | 5 | 4 | 5 | 5 | 5 | 5 | 5 | 5 |
| 799 | 5 | 5 | 5 | 5 | 5 | 5 | 5 | 5 | 5 |
| 811 | 5 | 5 | 4 | 5 | 5 | 5 | 5 | 5 | 5 |
| 814 | 5 | 4 | 3 | 5 | 5 | 5 | 4 | 4 | 5 |
| 824 | 5 | 5 | 5 | 5 | 5 | 5 | 5 | 5 | 5 |
| 836 | 5 | 5 | 4 | 5 | 5 | 5 | 5 | 5 | 5 |
| 847 | 5 | 5 | 4 | 5 | 5 | 5 | 5 | 5 | 5 |
| 870 | 5 | 4 | 3 | 5 | 5 | 5 | 5 | 5 | 5 |
| 871 | 5 | 5 | 4 | 5 | 5 | 5 | 5 | 5 | 5 |
| 892 | 5 | 4 | 3 | 5 | 5 | 5 | 4 | 5 | 5 |
| 894 | 5 | 5 | 4 | 5 | 5 | 5 | 5 | 5 | 5 |
| 895 | 5 | 5 | 4 | 5 | 5 | 5 | 5 | 5 | 5 |
| 907 | 5 | 5 | 4 | 5 | 5 | 5 | 5 | 5 | 5 |
| 919 | 5 | 5 | 5 | 5 | 5 | 5 | 5 | 5 | 5 |
| 934 | 5 | 5 | 4 | 5 | 5 | 5 | 4 | 5 | 5 |
| 943 | 5 | 4 | 3 | 5 | 5 | 5 | 5 | 5 | 5 |
| 955 | 5 | 5 | 3 | 5 | 5 | 5 | 5 | 5 | 5 |
| 976 | 5 | 5 | 4 | 5 | 5 | 5 | 5 | 5 | 5 |
| 980 | 5 | 5 | 4 | 5 | 5 | 5 | 5 | 5 | 5 |
| 992 | 5 | 5 | 5 | 5 | 5 | 5 | 5 | 5 | 5 |
| 1016 | 5 | 5 | 5 | 5 | 5 | 5 | 5 | 5 | 5 |
| 1028 | 5 | 5 | 4 | 5 | 5 | 5 | 5 | 5 | 5 |
| 1040 | 5 | 5 | 4 | 5 | 5 | 5 | 5 | 5 | 5 |
| 1052 | 5 | 5 | 3 | 5 | 5 | 5 | 5 | 5 | 5 |
| 1064 | 5 | 5 | 4 | 5 | 5 | 5 | 5 | 5 | 5 |
| 1085 | 5 | 5 | 4 | 5 | 5 | 5 | 5 | 5 | 5 |
| 1087 | 5 | 5 | 5 | 5 | 5 | 5 | 5 | 5 | 5 |
| 1088 | 5 | 5 | 5 | 5 | 5 | 5 | 5 | 5 | 5 |
| 1112 | 5 | 5 | 5 | 5 | 5 | 5 | 5 | 5 | 5 |
| 1124 | 5 | 5 | 5 | 5 | 5 | 5 | 5 | 5 | 5 |
| 1136 | 5 | 5 | 5 | 5 | 5 | 5 | 5 | 5 | 5 |
| 1148 | 5 | 5 | 4 | 5 | 5 | 5 | 5 | 5 | 5 |
| 1160 | 5 | 5 | 4 | 5 | 5 | 5 | 5 | 5 | 5 |
| 1171 | 5 | 5 | 4 | 5 | 5 | 5 | 5 | 4 | 5 |
| 1173 | 5 | 5 | 5 | 5 | 5 | 5 | 5 | 5 | 5 |
| 1197 | 5 | 5 | 5 | 5 | 5 | 5 | 5 | 5 | 5 |
| 1209 | 5 | 5 | 5 | 5 | 5 | 5 | 5 | 5 | 5 |
| 1233 | 5 | 5 | 5 | 5 | 5 | 5 | 5 | 5 | 5 |
| 1245 | 5 | 5 | 5 | 5 | 5 | 5 | 5 | 5 | 5 |
| 1269 | 5 | 5 | 4 | 5 | 5 | 5 | 5 | 5 | 5 |
| 1294 | 5 | 5 | 4 | 5 | 5 | 5 | 5 | 5 | 5 |
| 1305 | 5 | 5 | 5 | 5 | 5 | 5 | 5 | 5 | 5 |
| 1306 | 5 | 5 | 5 | 5 | 5 | 5 | 5 | 5 | 5 |
| 1311 | 5 | 5 | 5 | 5 | 5 | 5 | 5 | 5 | 5 |
| 1314 | 5 | 4 | 3 | 5 | 5 | 5 | 4 | 4 | 5 |
| 1315 | 5 | 5 | 5 | 5 | 5 | 5 | 5 | 5 | 5 |
| 1318 | 5 | 5 | 3 | 5 | 5 | 5 | 4 | 4 | 5 |
| 1327 | 5 | 5 | 3 | 5 | 5 | 5 | 4 | 4 | 5 |

Test Example 4

Herbicidal Effect on Upland Weeds After Emergence

Polyethylene-made vats having a size of 10 cm (length)× 20 cm (width)×5 cm (height) were filled with soil, sown with seeds of the following noxious upland weeds and with seeds of soybean plant and wheat as upland crop plants, and then covered with soil. The plants were made to grow up until they reached the leaf-stages mentioned below, after which an agent comprising a prescribed concentration of a compound of the present invention (listed in Tables 1 to 14) as active ingredient was sprayed.

Fourteen days after the treatment, the herbicidal effect was investigated, from which weed-killing rate was calculated in the same manner as in Test Example 1 and the results were judged. At the same time, phytotoxicity on soybean plant and wheat was investigated and judged in the same manner as in Test Example 3.

Sample weeds, their leaf stages, and leaf stages of soybean plant and wheat were as follows:

| | |
|---|---|
| Foxtail grass (Am) | 1–2 leaved stage |
| Barnyard grass (Ec) | 1–2 leaved stage |
| Velvetleaf (At) | 2-leaved stage |
| Cocklebur (Xs) | 2-leaved stage |
| Cleavers (Ga) | 1-leaved stage |
| Bird's eye speedwell (Vp) | Cotyledon to 1-leaved stage |
| Wheat (Eh) | 2-leaved stage |
| Soybean plant (So) | 1-leaved stage |

The results are summarized in Table 17.

TABLE 17

| No | Dosage (kg/ha) | Phytotoxicity | | Herbicidal effect | | | | | |
|---|---|---|---|---|---|---|---|---|---|
| | | Wh | So | Am | Ec | At | Xs | Ga | Vp |
| 1 | 5 | 2 | 1 | 3 | 4 | 5 | 4 | 3 | 5 |
| 2 | 5 | 2 | 1 | 4 | 5 | 5 | 4 | 5 | 5 |
| 3 | 5 | 3 | 2 | 5 | 5 | 5 | 4 | 5 | 5 |
| 28 | 5 | 1 | 0 | 2 | 3 | 3 | 2 | 2 | 4 |
| 29 | 5 | 1 | 0 | 3 | 3 | 4 | 3 | 3 | 4 |
| 30 | 5 | 2 | 1 | 4 | 4 | 5 | 3 | 3 | 5 |
| 43 | 5 | 1 | 0 | 2 | 3 | 3 | 2 | 1 | 3 |
| 44 | 5 | 1 | 0 | 3 | 3 | 3 | 2 | 3 | 4 |
| 53 | 5 | 1 | 0 | 3 | 3 | 4 | 2 | 2 | 3 |
| 58 | 5 | 3 | 2 | 4 | 4 | 5 | 3 | 3 | 4 |
| 71 | 5 | 4 | 2 | 4 | 4 | 4 | 3 | 3 | 5 |
| 97 | 5 | 0 | 0 | 2 | 2 | 2 | 1 | 1 | 3 |
| 99 | 5 | 4 | 2 | 4 | 5 | 5 | 4 | 4 | 5 |
| 100 | 5 | 2 | 3 | 4 | 5 | 5 | 4 | 5 | 5 |
| 101 | 5 | 3 | 2 | 4 | 5 | 5 | 4 | 4 | 5 |
| 126 | 5 | 0 | 0 | 2 | 2 | 3 | 1 | 1 | 3 |
| 127 | 5 | 2 | 1 | 3 | 3 | 3 | 1 | 2 | 3 |
| 128 | 5 | 2 | 1 | 4 | 4 | 4 | 3 | 3 | 5 |
| 129 | 5 | 4 | 2 | 5 | 5 | 5 | 5 | 5 | 5 |
| 130 | 5 | 3 | 1 | 4 | 5 | 5 | 4 | 4 | 5 |
| 157 | 5 | 3 | 2 | 4 | 5 | 5 | 4 | 4 | 5 |
| 158 | 5 | 4 | 2 | 4 | 5 | 5 | 4 | 5 | 5 |
| 189 | 5 | 2 | 0 | 3 | 3 | 4 | 2 | 3 | 4 |
| 200 | 5 | 0 | 0 | 2 | 3 | 3 | 1 | 1 | 3 |
| 201 | 5 | 0 | 0 | 3 | 2 | 3 | 1 | 1 | 3 |
| 219 | 5 | 2 | 1 | 4 | 5 | 5 | 3 | 3 | 5 |
| 224 | 5 | 2 | 1 | 3 | 4 | 4 | 2 | 2 | 4 |
| 228 | 5 | 1 | 1 | 3 | 3 | 4 | 1 | 2 | 4 |
| 234 | 5 | 0 | 0 | 2 | 3 | 3 | 1 | 1 | 3 |
| 243 | 5 | 0 | 0 | 2 | 3 | 3 | 1 | 1 | 3 |
| 246 | 5 | 1 | 0 | 3 | 3 | 4 | 2 | 2 | 5 |
| 275 | 5 | 2 | 1 | 3 | 4 | 4 | 3 | 3 | 4 |
| 276 | 5 | 3 | 2 | 4 | 5 | 5 | 4 | 4 | 5 |
| 289 | 5 | 2 | 1 | 4 | 5 | 5 | 3 | 4 | 5 |
| 290 | 5 | 3 | 2 | 5 | 5 | 5 | 4 | 5 | 5 |
| 291 | 5 | 2 | 2 | 4 | 5 | 5 | 4 | 4 | 5 |
| 305 | 5 | 2 | 1 | 3 | 4 | 4 | 2 | 2 | 4 |
| 310 | 5 | 2 | 0 | 3 | 4 | 4 | 3 | 2 | 3 |
| 334 | 5 | 2 | 1 | 3 | 4 | 4 | 3 | 3 | 4 |
| 339 | 5 | 2 | 1 | 3 | 4 | 4 | 2 | 2 | 4 |
| 343 | 5 | 0 | 0 | 2 | 4 | 3 | 2 | 2 | 3 |
| 359-1 | 5 | 2 | 3 | 5 | 5 | 5 | 5 | 5 | 5 |
| 359-2 | 5 | 3 | 4 | 5 | 5 | 5 | 5 | 5 | 5 |
| 359-3 | 5 | 2 | 3 | 5 | 5 | 5 | 5 | 5 | 5 |
| 359-4 | 5 | 2 | 4 | 5 | 5 | 5 | 5 | 5 | 5 |
| 359-5 | 5 | 3 | 2 | 5 | 5 | 5 | 5 | 5 | 5 |
| 359-6 | 5 | 2 | 3 | 5 | 5 | 5 | 5 | 5 | 5 |
| 360 | 5 | 4 | 3 | 5 | 5 | 5 | 5 | 4 | 5 |
| 361 | 5 | 5 | 4 | 5 | 5 | 5 | 5 | 5 | 5 |
| 375 | 5 | 4 | 4 | 5 | 5 | 5 | 5 | 5 | 5 |
| 388 | 5 | 5 | 4 | 5 | 5 | 5 | 5 | 5 | 5 |
| 414 | 5 | 5 | 4 | 5 | 5 | 5 | 5 | 5 | 5 |
| 423 | 5 | 5 | 4 | 5 | 5 | 5 | 5 | 5 | 5 |
| 431 | 5 | 4 | 3 | 4 | 4 | 5 | 4 | 4 | 5 |
| 438 | 5 | 5 | 4 | 5 | 5 | 5 | 5 | 5 | 5 |
| 447 | 5 | 5 | 4 | 5 | 5 | 5 | 5 | 5 | 5 |
| 450 | 5 | 4 | 4 | 5 | 5 | 5 | 4 | 4 | 5 |
| 462 | 5 | 5 | 5 | 5 | 5 | 5 | 5 | 5 | 5 |
| 474 | 5 | 3 | 3 | 5 | 5 | 5 | 4 | 4 | 5 |
| 486 | 5 | 4 | 4 | 5 | 5 | 5 | 5 | 5 | 5 |
| 498 | 5 | 4 | 4 | 5 | 5 | 5 | 4 | 4 | 5 |
| 510 | 5 | 5 | 4 | 5 | 5 | 5 | 5 | 5 | 5 |
| 519 | 5 | 5 | 4 | 5 | 5 | 5 | 5 | 5 | 5 |
| 527 | 5 | 5 | 5 | 5 | 5 | 5 | 4 | 5 | 5 |
| 534 | 5 | 4 | 4 | 5 | 5 | 5 | 5 | 5 | 5 |
| 558 | 5 | 5 | 5 | 5 | 5 | 5 | 5 | 5 | 5 |
| 570 | 5 | 4 | 4 | 5 | 5 | 5 | 4 | 4 | 5 |
| 582 | 5 | 4 | 4 | 5 | 5 | 5 | 5 | 5 | 5 |
| 606 | 5 | 4 | 3 | 5 | 5 | 5 | 4 | 4 | 5 |
| 630 | 5 | 4 | 3 | 5 | 5 | 5 | 4 | 4 | 5 |
| 654 | 5 | 3 | 2 | 3 | 3 | 4 | 2 | 2 | 4 |
| 678 | 5 | 4 | 3 | 4 | 5 | 5 | 3 | 3 | 5 |
| 679 | 5 | 3 | 2 | 4 | 5 | 5 | 4 | 4 | 5 |
| 703 | 5 | 3 | 2 | 4 | 5 | 5 | 4 | 4 | 5 |
| 724 | 5 | 3 | 2 | 4 | 4 | 3 | 3 | 4 | 5 |
| 727 | 5 | 4 | 4 | 5 | 5 | 5 | 4 | 4 | 5 |
| 739 | 5 | 5 | 4 | 5 | 5 | 5 | 5 | 5 | 5 |
| 760 | 5 | 4 | 3 | 5 | 5 | 5 | 4 | 5 | 5 |
| 763 | 5 | 4 | 3 | 4 | 5 | 5 | 4 | 4 | 5 |
| 774 | 5 | 5 | 4 | 5 | 5 | 5 | 5 | 5 | 5 |
| 775 | 5 | 5 | 5 | 5 | 5 | 5 | 5 | 5 | 5 |
| 796 | 5 | 4 | 4 | 5 | 5 | 5 | 4 | 4 | 5 |
| 798 | 5 | 5 | 4 | 5 | 5 | 5 | 5 | 5 | 5 |
| 799 | 5 | 5 | 5 | 5 | 5 | 5 | 5 | 5 | 5 |
| 811 | 5 | 5 | 4 | 5 | 5 | 5 | 4 | 4 | 5 |
| 814 | 5 | 4 | 3 | 5 | 5 | 5 | 4 | 4 | 5 |
| 824 | 5 | 5 | 4 | 5 | 5 | 5 | 5 | 5 | 5 |
| 836 | 5 | 5 | 4 | 5 | 5 | 5 | 5 | 5 | 5 |
| 847 | 5 | 5 | 4 | 5 | 5 | 5 | 5 | 5 | 5 |
| 870 | 5 | 4 | 3 | 5 | 5 | 5 | 5 | 5 | 5 |
| 871 | 5 | 5 | 4 | 5 | 5 | 5 | 5 | 5 | 5 |
| 892 | 5 | 4 | 3 | 5 | 5 | 5 | 4 | 4 | 5 |
| 894 | 5 | 5 | 4 | 5 | 5 | 5 | 4 | 5 | 5 |
| 895 | 5 | 5 | 4 | 5 | 5 | 5 | 5 | 5 | 5 |
| 907 | 5 | 5 | 4 | 5 | 5 | 5 | 5 | 5 | 5 |
| 919 | 5 | 5 | 5 | 5 | 5 | 5 | 5 | 5 | 5 |
| 934 | 5 | 5 | 4 | 5 | 5 | 5 | 4 | 5 | 5 |
| 943 | 5 | 4 | 4 | 5 | 5 | 5 | 5 | 5 | 5 |
| 955 | 5 | 5 | 3 | 5 | 5 | 5 | 5 | 5 | 5 |
| 976 | 5 | 5 | 4 | 5 | 5 | 5 | 5 | 5 | 5 |
| 980 | 5 | 5 | 4 | 5 | 5 | 5 | 5 | 5 | 5 |
| 992 | 5 | 5 | 5 | 5 | 5 | 5 | 5 | 5 | 5 |
| 1016 | 5 | 5 | 5 | 5 | 5 | 5 | 5 | 5 | 5 |
| 1028 | 5 | 5 | 4 | 5 | 5 | 5 | 5 | 4 | 5 |
| 1040 | 5 | 5 | 4 | 5 | 5 | 5 | 5 | 5 | 5 |
| 1052 | 5 | 5 | 3 | 5 | 5 | 5 | 5 | 5 | 5 |
| 1064 | 5 | 5 | 4 | 5 | 5 | 5 | 5 | 5 | 5 |
| 1085 | 5 | 5 | 4 | 5 | 5 | 5 | 5 | 4 | 5 |
| 1087 | 5 | 5 | 4 | 5 | 5 | 5 | 5 | 5 | 5 |
| 1088 | 5 | 5 | 5 | 5 | 5 | 5 | 5 | 5 | 5 |
| 1112 | 5 | 5 | 5 | 5 | 5 | 5 | 5 | 5 | 5 |
| 1124 | 5 | 5 | 5 | 5 | 5 | 5 | 5 | 5 | 5 |
| 1136 | 5 | 5 | 5 | 5 | 5 | 5 | 5 | 5 | 5 |
| 1148 | 5 | 5 | 4 | 5 | 5 | 5 | 5 | 5 | 5 |
| 1160 | 5 | 5 | 4 | 5 | 5 | 5 | 5 | 5 | 5 |
| 1171 | 5 | 5 | 4 | 5 | 5 | 5 | 4 | 4 | 5 |
| 1173 | 5 | 5 | 5 | 5 | 5 | 5 | 5 | 5 | 5 |
| 1197 | 5 | 5 | 5 | 5 | 5 | 5 | 5 | 5 | 5 |
| 1209 | 5 | 5 | 5 | 5 | 5 | 5 | 5 | 5 | 5 |
| 1233 | 5 | 5 | 5 | 5 | 5 | 5 | 5 | 5 | 5 |
| 1245 | 5 | 5 | 5 | 5 | 5 | 5 | 5 | 5 | 5 |
| 1269 | 5 | 5 | 4 | 5 | 5 | 5 | 5 | 5 | 5 |
| 1294 | 5 | 5 | 4 | 5 | 5 | 5 | 5 | 5 | 5 |
| 1305 | 5 | 5 | 5 | 5 | 5 | 5 | 5 | 5 | 5 |
| 1306 | 5 | 5 | 5 | 5 | 5 | 5 | 5 | 5 | 5 |
| 1311 | 5 | 5 | 5 | 5 | 5 | 5 | 5 | 5 | 5 |

TABLE 17-continued

| No | Dosage (kg/ha) | Phytotoxicity | | Herbicidal effect | | | | | |
|---|---|---|---|---|---|---|---|---|---|
| | | Wh | So | Am | Ec | At | Xs | Ga | Vp |
| 1314 | 5 | 4 | 4 | 5 | 5 | 5 | 4 | 4 | 5 |
| 1315 | 5 | 5 | 5 | 5 | 5 | 5 | 5 | 5 | 5 |
| 1318 | 5 | 4 | 3 | 5 | 5 | 5 | 4 | 5 | 5 |
| 1327 | 5 | 4 | 3 | 5 | 5 | 5 | 4 | 5 | 5 |

What is claimed is:

1. A fused heterocyclic dicarboxylic acid diamide derivative represented by formula (I) or a salt thereof:

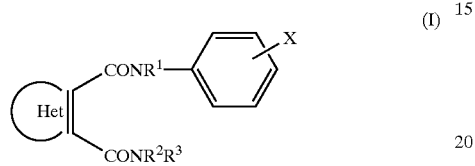

(I)

wherein $R^1$ represents hydrogen atom or $(C_1-C_6)$ alkyl group;

R² and R³ may be same or different and each represents hydrogen atom, $(C_1-C_8)$ alkyl group, halo $(C_1-C_6)$ alkyl group, $(C_3-C_8)$ cycloalkyl group, $(C_3-C_6)$ cycloalkyl $(C_1-C_6)$ alkyl group, $(C_3-C_6)$ cycloalkyl group having, on the ring thereof, at least one, same or different halogen atoms, $(C_1-C_6)$ alkoxy group, $(C_1-C_6)$ alkoxy $(C_1-C_6)$ alkyl group, $(C_1-C_6)$ alkylthio group, alkylthio $(C_1-C_6)$ alkyl group, cyano $(C_1-C_6)$ alkyl group, $(C_1-C_6)$ alkoxycarbonyl $(C_1-C_6)$ alkyl group, amino $(C_1-C_6)$ alkyl group, substituted amino $(C_1-C_6)$ alkyl group substituted with one or two, same or different $(C_1-C_6)$ alkyl groups, phenyl $(C_1-C_6)$ alkyl group, substituted phenyl $(C_1-C_6)$ alkyl group having, on the ring thereof, at least one, same or different substituents selected from the group consisting of halogen atoms and $(C_1-C_6)$ alkyl groups, phenyl $(C_1-C_6)$ alkoxy group or substituted phenyl $(C_1-C_6)$ alkoxy group having, on the ring thereof, at least one, same or different substituents selected from the group consisting of halogen atoms and $(C_1-C_6)$ alkyl groups; or R² and R³, taken conjointly, represent a 5- to 6-membered heterocycle having at least one, same or different heteroatoms selected from the group consisting of oxygen atom, sulfur atom and nitrogen atom, further, the carbon atom or nitrogen atom on said heterocycle may have at least one, same or different substituents selected from the group consisting of halogen atom, $(C_1-C_6)$ alkyl group, halo $(C_1-C_6)$ alkyl group, $(C_1-C_6)$ alkoxy group, halo $(C_1-C_6)$ alkoxy group, $(C_1-C_6)$ alkylthio group and halo $(C_1-C_6)$ alkylthio group;

X represents 0 to 5, same or different substituents selected from the group consisting of halogen atom, nitro group, cyano group, $(C_1-C_6)$ alkyl group, halo $(C_1-C_6)$ alkyl group, $(C_3-C_6)$ cycloalkyl group, $(C_3-C_6)$ cycloalkyl $(C_1-C_6)$ alkyl group, $(C_3-C_6)$ cycloalkyl group having, on the ring thereof, at least one, same or different halogen atoms, $(C_1-C_6)$ alkoxy group, halo $(C_1-C_6)$ alkoxy group, $(C_1-C_6)$ alkylthio group, halo $(C_1-C_6)$ alkylthio group, $(C_1-C_6)$ alkylsulfinyl group, halo $(C_1-C_6)$ alkylsulfinyl group, $(C_1-C_6)$ alkylsulfonyl group, halo $(C_1-C_6)$ alkylsulfonyl group, $(C_1-C_6)$ alkoxy $(C_1-C_6)$ alkylthio $(C_1-C_6)$ alkyl group, $(C_1-C_6)$ alkoxycarbonyl group, amino group, substituted amino group substituted with same or different $(C_1-C_6)$ alkyl groups, cyano $(C_1-C_6)$ alkyl groups, phenyl $(C_1-C_6)$ alkyl groups, $(C_1-C_6)$ alkoxycarbonyl $(C_1-C_6)$ alkyl groups, $(C_1-C_6)$ alkoxycarbonyl groups, $(C_1-C_6)$ acyl groups, $(C_1-C_6)$ alkylsulfonyl groups or halo $(C_1-C_6)$ alkylsulfonyl groups, phenyl group, substituted phenyl group having at least one, same or different substituents selected from the group consisting of halogen atom, $(C_1-C_6)$ alkyl group, halo $(C_1-C_6)$ alkyl group, $(C_1-C_6)$ alkoxy group, halo $(C_1-C_6)$ alkoxy group, $(C_1-C_6)$ alkylthio group, halo $(C_1-C_6)$ alkylthio group, $(C_1-C_6)$ alkylsulfinyl group, halo $(C_1-C_6)$ alkylsulfinyl group, $(C_1-C_6)$ alkylsulfonyl group, halo $(C_1-C_6)$ alkylsulfonyl group and phenyl group, phenoxy group, substituted phenoxy group having at least one, same or different substituents selected from the group consisting of halogen atom, $(C_1-C_6)$ alkyl group, halo $(C_1-C_6)$ alkyl group, $(C_1-C_6)$ alkoxy group, halo $(C-C_6)$ alkoxy group, $(C_1-C_6)$ alkylthio group, halo $(C_1-C_6)$ alkylthio group and phenyl group, phenylthio group, substituted phenylthio group having at least one, same or different substituents selected from the group consisting of halogen atom, $(C_1-C_6)$ alkyl group, halo $(C_1-C_6)$ alkyl group, $(C_1-C_6)$ alkoxy group, halo $(C_1-C_6)$ alkoxy group, $(C_1-C_6)$ alkylthio group, halo $(C_1-C_6)$ alkylthio group and phenyl group, phenyl $(C_1-C_6)$ alkyl group or substituted phenyl $(C_1-C_6)$ alkyl group having, on the ring thereof, at least one, same or different substituents selected from the group consisting of halogen atom, $(C_1-C_6)$ alkyl group, halo $(C_1-C_6)$ alkyl group, $(C_1-C_6)$ alkoxy group, halo $(C_1-C_6)$ alkoxy group, $(C_1-C_6)$ alkylthio group, halo $(C_1-C_6)$ alkylthio group and phenyl group; and

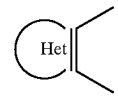

represents $Q^4, Q^5, Q^6, Q^7, Q^8, Q^9, Q^{10}, Q^{11}, Q^{12}$ or $Q^{13}$, wherein:

$Q^4$ is a group of the following formula:

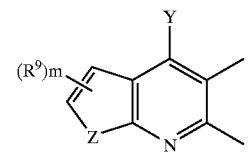

wherein $R^9$ is same or different and represents halogen atom, nitro group, cyano group, $(C_1-C_6)$ alkyl group, halo $(C_1-C_6)$ alkyl group, $(C_3-C_6)$ cycloalkyl group, $(C_3-C_6)$ cycloalkyl $(C_1-C_6)$ alkyl group, $(C_1-C_6)$ alkoxy group, halo $(C_1-C_6)$ alkoxy group, $(C_1-C_6)$ alkoxy $(C_1-C_6)$ alkyl group, $(C_1-C_6)$ alkoxycarbonyl group, $(C_1-C_6)$ alkylthio group, halo $(C_1-C_6)$ alkylthio group, $(C_1-C_6)$ alkylsulfinyl group, $(C_1-C_6)$ alkylsulfonyl group, halo $(C_1-C_6)$ alkylsulfonyl group, $(C_1-C_6)$ alkylthio $(C_1-C_6)$ alkyl group, phenyl group, substituted phenyl group having at least one, same or different substituents selected from the group consisting of halogen atom, $(C_1-C_6)$ alkyl group, halo $(C_1-C_6)$ alkyl group, $(C_1-C_6)$ alkoxy group, halo $(C_1-C_6)$ alkoxy group, $(C_1-C_6)$ alkylthio group, halo $(C_1-C_6)$ alkylthio group, $(C_1-C_6)$ alkylsulfinyl group, halo $(C_1-C_6)$ alkylsulfinyl group, $(C_1-C_6)$ alkylsulfonyl group, halo $(C_1-C_6)$ alkylsulfonyl group and phenyl group, phenoxy group, substituted phenoxy group having at least one, same or different substituents selected from the group consisting of halogen atom, $(C_1-C_6)$ alkyl group, halo $(C_1-C_6)$ alkyl group, $(C_1-C_6)$ alkoxy group, halo $(C_1-C_6)$ alkoxy group, $(C_1-C_6)$ alkylthio group, halo $(C_1-C_6)$ alkylthio group and phenyl group, phenylthio group, substituted phenylthio group having at least one, same or different substituents selected from the group consisting of halogen atom, $(C_1-C_6)$ alkyl group, halo $(C_1-C_6)$ alkyl group, $(C_1-C_6)$ alkoxy group, halo $(C_1-C_6)$ alkoxy group, $(C_1-C_6)$ alkylthio group, halo $(C_1-C_6)$ alkylthio group and phenyl group, amino group, substituted amino group substituted with at least one, same or different substituents selected from the group consisting of $(C_1-C_6)$ alkyl group, cyano $(C_1-C_6)$ alkyl group, $(C_1-C_6)$ alkoxycarbonyl $(C_1-C_6)$ alkyl group, $(C_1-C_6)$ alkoxycarbonyl group, $(C_1-C_6)$ alkoxyaminocarbonyl group, $(C_1-C_6)$ acyl group, $(C_1-C_6)$ alkylsulfonyl group, halo $(C_1-C_6)$ alkylsulfonyl group and phenyl $(C_1-C_6)$ alkyl group, $(C_3-C_5)$ alkyleneimino group, hydrazino group or substituted hydrazino group substituted with same or different $(C_1-C_6)$ alkyl groups; m represents an integer of 0 to 2;

Z represents oxygen atom, sulfur atom or $N-R^{10}$ wherein $R^{10}$ represents hydrogen atom, hydroxyl group, $(C_1-C_6)$ alkyl group, halo $(C_1-C_6)$ alkyl group, $(C_3-C_6)$ cycloalkyl group, $(C_3-C_6)$ cycloalkyl $(C_1-C_6)$ alkyl group, $(C_1-C_6)$ alkoxy group, $(C_1-C_6)$ alkoxy $(C_1-C_6)$ alkyl group, $(C_1-C_6)$ alkoxycarbonyl group, $(C_1-C_6)$ alkylsulfonyl group, halo $(C_1-C_6)$ alkylsulfonyl group or $(C_1-C_6)$ alkylthio $(C_1-C_6)$ alkyl group; and Y represents hydrogen atom, halogen atom, nitro group, cyano group, $(C_1-C_6)$ alkyl group, halo $(C_1-C_6)$ alkyl group, $(C_3-C_6)$ cycloalkyl group, $(C_3-C_6)$ cycloalkyl $(C_1-C_6)$ alkyl group, $(C_1-C_6)$ alkoxy group, halo $(C_1-C_6)$ alkoxy group, $(C_1-C_6)$ alkoxy $(C_1-C_6)$ alkyl group, $(C_1-C_6)$ alkylthio group, halo $(C_1-C_6)$ alkylthio group, $(C_1-C_6)$ alkylsulfinyl group, halo $(C_1-C_6)$ alkylsulfinyl group, $(C_1-C_6)$ alkylsulfonyl group, halo $(C_1-C_6)$ alkylsulfonyl group, $(C_1-C_6)$ alkylthio $(C_1-C_6)$ alkyl group, $(C_1-C_6)$ alkoxycarbonyl group, phenyl group, substituted phenyl group having at least one, same or different substituents selected from the group consisting of halogen atom, $(C_1-C_6)$ alkyl group, halo $(C_1-C_6)$ alkyl group, $(C_1-C_6)$ alkoxy group, halo $(C_1-C_6)$ alkoxy group, $(C_1-C_6)$ alkylthio group, halo $(C_1-C_6)$ alkylthio group, $(C_1-C_6)$ alkylsulfinyl group, halo $(C_1-C_6)$ alkylsulfinyl group, $(C_1-C_6)$ alkylsulfonyl group, halo $(C_1-C_6)$ alkylsulfonyl group and phenyl group, phenoxy group, substituted phenoxy group having at least one, same or different substituents selected from the group consisting of halogen atom, $(C_1-C_6)$ alkyl group, halo $(C_1-C_6)$ alkyl group, $(C_1-C_6)$ alkoxy group, halo $(C_1-C_6)$ alkoxy group, $(C_1-C_6)$ alkylthio group, halo $(C_1-C_6)$ alkylthio group and phenyl group, phenylthio group, substituted phenylthio group having at least one, same or different substituents selected from the group consisting of halogen atom, $(C_1-C_6)$ alkyl group, halo $(C_1-C_6)$ alkyl group, $(C_1-C_6)$ alkoxy group, halo $(C_1-C_6)$ alkoxy group, $(C_1-C_6)$ alkylthio group, halo $(C_1-C_6)$ alkylthio group and phenyl group, amino group, substituted amino group having at least one, same or different substituents selected from the group consisting of $(C_1-C_6)$ alkyl group, cyano $(C_1-C_6)$ alkyl group, $(C_1-C_6)$ alkoxycarbonyl $(C_1-C_6)$ alkyl group, $(C_1-C_6)$ alkoxycarbonyl group, $(C_1-C_6)$ alkoxyaminocarbonyl group, $(C_1-C_6)$ acyl group, $(C_1-C_6)$ alkylsulfonyl group, halo $(C_1-C_6)$ alkylsulfonyl group and phenyl $(C_1-C_6)$ alkyl group, $(C_3-C_5)$ alkyleneimino group, hydrazino group or substituted hydrazino group substituted with same or different $(C_1-C_6)$ alkyl groups;

$Q^5$ is a group of the following formula:

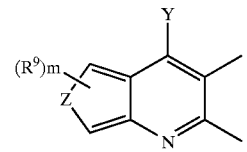

wherein $R^9$, Y, Z and m are as defined above;

$Q^6$ is a group of the following formula:

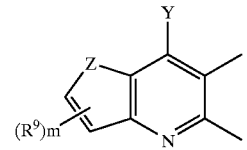

wherein $R^9$, Y, Z and m are as defined above;

$Q^7$ is a group of the following formula:

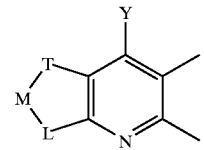

wherein at least one of L, M and T represent oxygen atom, sulfur atom, sulfinyl group, sulfonyl group, carbonyl group or $N-R^{11}$ wherein $R^{11}$ represents hydrogen atom, hydroxyl group, $(C_1-C_6)$ alkyl group, halo $(C_1-C_6)$ alkyl group, $(C_3-C_6)$ cycloalkyl group, $(C_3-C_6)$ cycloalkyl $(C_1-C_6)$ alkyl group, $(C_1-C_6)$ alkoxy group, $(C_1-C_6)$ alkoxy $(C_1-C_6)$ alkyl group, $(C_1-C_6)$ alkoxycarbonyl group, $(C_1-C_6)$ alkylsulfonyl group, halo $(C_1-C_6)$ alkylsulfonyl group or $(C_1-C_6)$ alkylthio $(C_1-C_6)$ alkyl group, and the others of L, M and T each represents $C-(R^{12})R^{13}$ wherein $R^{12}$ and $R^{13}$ may be same or different and each represents hydrogen atom, (C₁–C₆) alkyl group, halo (C₁–C₆) alkyl group, (C₃–C₆) cycloalkyl group, (C₃–C₆) cycloalkyl (C₁–C₆) alkyl group, (C₃–C₆) cycloalkyl group having at least one, same or different halogen atoms on the ring thereof, (C₁–C₆) alkoxy group, (C₁–C₆) alkoxy (C₁–C₆) alkyl group, (C₁–C₆) alkylthio (C₁–C₆) alkyl group, (C₁–C₆) alkoxycarbonyl (C₁–C₆) alkyl group, phenyl (C₁–C₆) alkyl group, substituted phenyl (C₁–C₆) alkyl group having, on the ring thereof, at least one, same or different substituents selected from the group consisting of halogen atoms and (C₁–C₆) alkyl groups, phenyl (C₁–C₆) alkoxy group, substituted phenyl (C₁–C₆) alkoxy group having, on the ring thereof, at least one, same or different substituents selected from the group consisting of halogen atoms and (C₁–C₆) alkyl groups, amino (C₁–C₆) alkyl group or substituted amino (C₁–C₆) alkyl group substituted with at least one, same or different (C₁–C₆) alkyl groups; and Y is defined above;

Q8 is as group of the following formula:

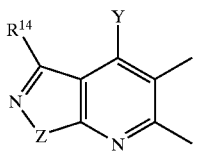

wherein $R^{14}$ represents hydrogen atom or is the same as $R^9$, and Y and Z are as defined above;

Q⁹ is a group of the following formula:

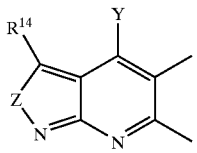

wherein $R^{14}$, Y and Z are as defined above;

Q¹⁰ is a group of the following formula:

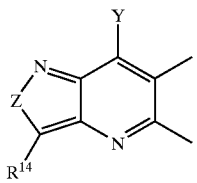

wherein $R^{14}$, Y and Z are as defined above;

Q¹¹ is a group of the following formula:

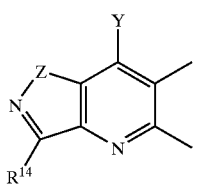

wherein $R^{14}$, Y and Z are as defined above;

Q¹² is a group of the following formula:

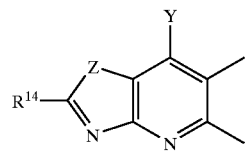

wherein $R^{14}$, Y and Z are as defined above;

and Q¹³ is a group of the following formula:

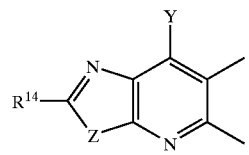

wherein $R^{14}$ and Z are as defined above.

2. A fused heterocyclic dicarboxylic acid diamide derivative or a salt thereof according to claim 1, wherein:

$R^1$ represents hydrogen atom;

$R^2$ and $R^3$ may be same or different and each represents hydrogen atom, (C₁–C₈) alkyl group or (C₃–C₆) cycloalkyl group; and X represents 0 to 5, same or different substituents selected from the group consisting of halogen atom, (C₁–C₆) alkyl group, halo (C₁–C₆) alkyl group, (C₃–C₆) cycloalkyl group, (C₁–C₆) alkoxy group, halo (C₁–C₆) alkyl group, (C₁–C₆) alkylthio group, halo (C₁–C₆) alkylthio group, (C₁–C₆) alkoxy (C₁–C₆) alkyl group, (C₁–C₆) alkylthio (C₁–C₆) alkyl group and (C₁–C₆) alkoxycarbonyl group; and

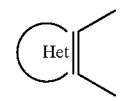

represents Q⁴, Q⁵, Q⁶, Q⁷, Q⁸, Q⁹, Q¹⁰, Q¹¹, Q¹² or Q¹³, wherein

Q⁴ is a group of the following formula:

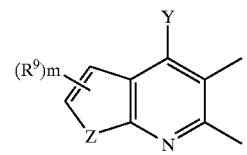

wherein $R^9$ is same or different and represents halogen atom, (C₁–C₆) alkyl group or (C₃–C₆) cycloalkyl group; m represents an integer of 0 to 2; Z represents oxygen atom, sulfur atom or N—$R^{10}$ wherein $R^{10}$ represents hydrogen atom, (C₁–C₆) alkyl group, halo (C₁–C₆) alkyl group or (C₃–C₆) cycloalkyl group; and Y represents hydrogen atom, (C₁–C₆) alkyl group or (C₃–C₆) cycloalkyl group;

$Q^5$ is a group of the following formula:

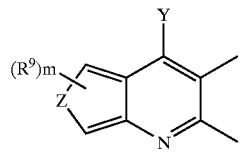

wherein $R^9$ is same or different and represents halogen atom, ($C_1$–$C_6$) alkyl group or ($C_3$–$C_6$) cycloalkyl group; m represents an integer of 0 to 2; Y represents hydrogen atom, ($C_1$–$C_6$) alkyl group or ($C_3$–$C_6$) cycloalkyl group; and Z represents oxygen atom or sulfur atom;

$Q^6$ is a group of the following formula:

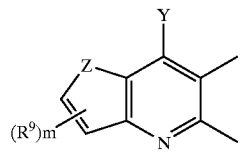

wherein $R^9$ is same or different and represents halogen atom, ($C_1$–$C_6$) alkyl group or ($C_3$–$C_6$) cycloalkyl group; m represents an integer of 0 to 2; Y represents hydrogen atom, ($C_1$–$C_6$) alkyl group or ($C_3$–$C_6$) cycloalkyl group; and Z represents oxygen atom, sulfur atom or N—$R^{10}$ wherein $R^{10}$ is as defined above;

$Q^7$ is a group of the following formula:

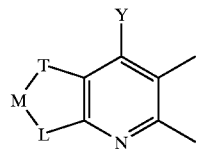

wherein at least one of L, M and T represents oxygen atom, sulfur atom, sulfinyl group, sulfonyl group or N—$R^{11}$ wherein $R^{11}$ represents hydrogen atom, ($C_1$–$C_6$) alkyl group or halo ($C_1$–$C_6$) alkyl group; and the others of L, M and T represent C-($R^{12}$)$R^{13}$ wherein $R^{12}$ and $R^{13}$ may be same or different and represent hydrogen atom, ($C_1$–$C_6$) alkyl group, halo ($C_1$–$C_6$) alkyl group or ($C_1$–$C_6$) alkoxy group; and Y represents hydrogen atom, ($C_1$–$C_6$) alkyl group or ($C_3$–$C_6$) cycloalkyl group;

$Q^8$ is a group of the following formula:

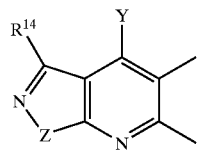

wherein $R^{14}$ represents hydrogen atom, ($C_1$–$C_6$) alkyl group, halo ($C_1$–$C_6$) alkyl group or ($C_3$–$C_6$) cycloalkyl group; Y represents hydrogen atom, ($C_1$–$C_6$) alkyl group or ($C_3$–$C_6$) cycloalkyl group; and Z represents oxygen atom, sulfur atom or N—$R^{10}$ wherein $R^{10}$ is as defined above;

$Q^9$ is a group of the following formula:

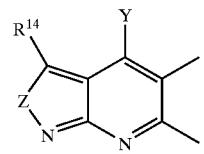

wherein $R^{14}$ represents hydrogen atom, ($C_1$–$C_6$) alkyl group, halo ($C_1$–$C_6$) alkyl group or ($C_3$–$C_6$) cycloalkyl group; Y represents hydrogen atom, ($C_1$–$C_6$) alkyl group or ($C_3$–$C_6$) cycloalkyl group; and Z represents N—$R^{10}$ wherein $R^{10}$ is as defined above;

$Q^{10}$ is a group of the following formula:

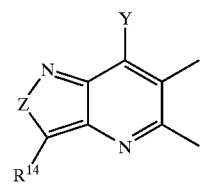

wherein $R^{14}$ represents hydrogen atom, ($C_1$–$C_6$) alkyl group, halo ($C_1$–$C_6$) alkyl group or ($C_3$–$C_6$) cycloalkyl group; Y represents hydrogen atom, ($C_1$–$C_6$) alkyl group or ($C_3$–$C_6$) cycloalkyl group; and Z represents N—$R^{10}$) wherein $R^{10}$ is as defined above;

$Q^{11}$ is a group of the following formula:

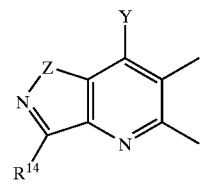

wherein $R^4$ represents hydrogen atom, ($C_1$–$C_6$) alkyl group, halo ($C_1$–$C_6$) alkyl group or ($C_3$–$C_6$) cycloalkyl group; Y represents hydrogen atom, ($C_1$–$C_6$) alkyl group or ($C_3$–$C_6$) cycloalkyl group; and Z represents N—$R^{10}$ wherein $R^{10}$ is as defined above;

$Q^{12}$ is a group of the following formula:

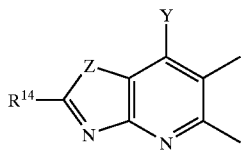

wherein $R^{14}$ represents hydrogen atom, ($C_1$–$C_6$) alkyl group, halo ($C_1$–$C_6$) alkyl group or ($C_3$–$C_6$) cycloalkyl group; Y represents hydrogen atom, ($C_1$–$C_6$) alkyl group or ($C_3$–$C_6$) cycloalkyl group; and Z represents N—$R^{10}$ wherein $R^{10}$ is as defined above;

and $Q^{13}$ is a group of the following formula:

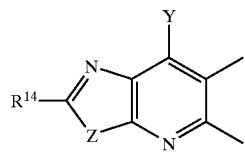

wherein $R^{14}$ represents hydrogen atom, $(C_1-C_6)$ alkyl group, halo $(C_1-C_6)$ alkyl group or $(C_3-C_6)$ cycloalkyl group; Y represents hydrogen atom, $(C_1-C_6)$ alkyl group or $(C_3-C_6)$ cycloalkyl group; and Z represents N—$R^{10}$ wherein $R^1$ is as defined above.

3. A fused heterocyclic dicarboxylic acid diamide derivative or a salt thereof according to claim 2, wherein $R^1$ represents hydrogen atom; $R^2$ represents hydrogen atom; $R^3$ represents hydrogen atom, $(C_1-C_8)$ alkyl group or $(C_3-C_8)$ cycloalkyl group; X represents 0 to 5, same or different substituents selected from the group consisting of halogen atom, $(C_1-C_6)$ alkyl group, halo $(C_1-C_6)$ alkyl group, $(C_1-C_6)$ alkoxy group and halo $(C_1-C_6)$ alkoxy group; and

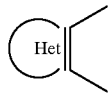

represents $Q^4$, $Q^5$, $Q^7$, $Q^8$, or $Q^{11}$, wherein:

$Q^4$ is a group of the following formula:

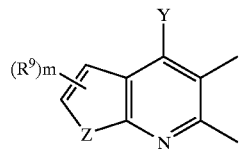

wherein $R^9$ is same or different and represents halogen atom, $(C_1-C_6)$ alkyl group or $(C_3-C_6)$ cycloalkyl group; m represents an integer of 0 to 2; Z represents oxygen atom, sulfur atom or N—$R^{10}$ wherein $R^{10}$ represents hydrogen atom, $(C_1-C_6)$ alkyl group, halo $(C_1-C_6)$ alkyl group or $(C_3-C_6)$ cycloalkyl group; and Y represents hydrogen atom, $(C_1-C_6)$ alkyl group or $(C_3-C_6)$ cycloalkyl group;

$Q^5$ is a group of the following formula:

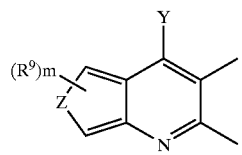

wherein $R^9$ is same or different and represents halogen atom, $(C_1-C_6)$ alkyl group or $(C_3-C_6)$ cycloalkyl group; m represents an integer of 0 to 2; Y represents hydrogen atom, $(C_1-C_6)$ alkyl group or $(C_3-C_6)$ cycloalkyl group; and Z represents oxygen atom, sulfur atom or N—$R^{10}$ wherein $R^{10}$ is as defined above;

$Q^7$ is a group of the following formula:

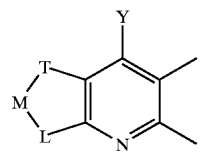

wherein at least one of L, M and T represent oxygen atom, sulfur atom, sulfinyl group, sulfonyl group or N—$R^{11}$ wherein $R^{11}$ represents hydrogen atom, $(C_1-C_6)$ alkyl group or halo $(C_1-C_6)$ alkyl group, and the others of L, M and T represent C-$(R^{12})R^{13}$ wherein $R^{12}$ and $R^{13}$ may be same or different and each represents hydrogen atom, $(C_1-C_6)$ alkyl group, halo $(C_1-C_6)$ alkyl group or $(C_1-C_6)$ alkoxy group; and Y represents hydrogen atom, $(C_1-C_6)$ alkyl group or $(C_3-C_6)$ cycloalkyl group;

$Q^8$ is a group of the following formula:

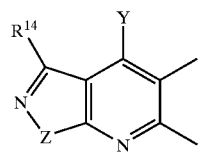

wherein $R^{14}$ represents hydrogen atom, $(C_1-C_6)$ alkyl group, halo $(C_1-C_6)$ alkyl group or $(C_3-C_6)$ cycloalkyl group; Y represents hydrogen atom, $(C_1-C_6)$ alkyl group or $(C_3-C_6)$ cycloalkyl group; and Z represents oxygen atom, sulfur atom or N—$R^{10}$ wherein $R^{10}$ is as defined above; and $Q^{11}$ is a group of the following formula:

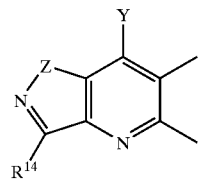

wherein $R^{14}$ represents hydrogen atom, $(C_1-C_6)$ alkyl group, halo $(C_1-C_6)$ alkyl group or $(C_3-C_6)$ cycloalkyl group; Y represents hydrogen atom, $(C_1-C_6)$ alkyl group or $(C_3-C_6)$ cycloalkyl group; and Z represents N—$R^{10}$ wherein $R^{10}$ is as defined above.

4. A herbicide characterized by containing a fused heterocyclic dicarboxylic acid diamide derivative or a salt thereof according to any of claims 1 to 3 as an active ingredient.

5. A method for using a herbicide characterized by applying an effective amount of a herbicide according to claim 4 to a weed or a soil for the purpose of controlling a weed undesirable for the growth of useful plants.

* * * * *